(12) United States Patent
Batuman et al.

(10) Patent No.: US 9,353,171 B2
(45) Date of Patent: May 31, 2016

(54) USE OF PITUITARY ADENYLATE CYCLASE-ACTIVATING POLYPEPTIDE (PACAP) AND PACAP ANALOGS FOR TREATING CONTRAST-INDUCED NEPHROPATHY

(71) Applicant: The Administrators of the Tulane Educational Fund, New Orleans, LA (US)

(72) Inventors: Vecihi Batuman, New Orleans, LA (US); Jerome L. Maderdrut, New Orleans, LA (US); Min Li, New Orleans, LA (US); David H. Coy, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 14/357,393

(22) PCT Filed: Nov. 16, 2012

(86) PCT No.: PCT/US2012/065586
§ 371 (c)(1),
(2) Date: May 9, 2014

(87) PCT Pub. No.: WO2013/074966
PCT Pub. Date: May 23, 2013

(65) Prior Publication Data
US 2014/0314838 A1    Oct. 23, 2014

Related U.S. Application Data

(60) Provisional application No. 61/596,917, filed on Feb. 9, 2012, provisional application No. 61/561,070, filed on Nov. 17, 2011.

(51) Int. Cl.
*A61K 38/22* (2006.01)
*A61P 13/02* (2006.01)
*C07K 14/575* (2006.01)
*A61K 45/06* (2006.01)

(52) U.S. Cl.
CPC ....... *C07K 14/57563* (2013.01); *A61K 38/2242* (2013.01); *A61K 38/2278* (2013.01); *A61K 45/06* (2013.01)

(58) Field of Classification Search
None
See application file for complete search history.

(56) References Cited

U.S. PATENT DOCUMENTS

2009/0221514 A1    9/2009   Szeto et al.
2011/0268789 A1   11/2011   Li et al.

FOREIGN PATENT DOCUMENTS

WO    WO 2010036936 A2 *   4/2010

OTHER PUBLICATIONS

Li et al (2010. 32:522-532, published on-line Oct. 28, 2010).*
Khan et al, 2013. Physiol Rep. 1(6); 14 pages.*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Bourgault et al., "Novel stable PACAP analogs with potent activity towards the PAC1 receptor," Peptides. 29(6):919-32 (2008).
International Search Report for International Application No. PCT/US12/65586 mailed Feb. 5, 2013 (5 pages).
Written Opinion of the International Searching Authority for International Application No. PCT/US12/65586 mailed Feb. 5, 2013 (5 pages).
Carden and Granger, "Pathophysiology of ischemia-reperfusion injury," J Pathol. 190:255-266 (2000).
Khan et al., "Pituitary adenylate cyclase-activating polypeptide prevents contrast-induced nephropathy in a novel mouse model," Physiological Rep. 1(6):1-14 (2013).
Naughton, "Drug-induced nephrotoxicity," Am Fam Physician. 78(6):743-750 (2008).
O'Donnell et al., "Iodinated contrast media alter immune response in pro-inflammatory states," Acta Radiol. 51:635-640 (2010).
Sicari, "Anti-ischemic therapy and stress testing: pathophysiologic, diagnostic and prognostic implications," Cardiovasc Ultrasound. 2(14):1-7 (2004).

* cited by examiner

*Primary Examiner* — Zachary Howard
(74) *Attorney, Agent, or Firm* — Clark & Elbing LLP

(57) ABSTRACT

Featured are methods and compositions for treating, managing, preventing, or reducing injury to the kidney of a mammal (e.g., a human) caused by one or more iodinated radiocontrast media. The methods include administering an effective amount of one or more pituitary adenylate cyclase-activating polypeptide (PACAP)-like compounds, which includes native human PACAP38, native human PACAP27, native human vasoactive intestinal peptide (VIP), their agonists, analogs, fragments, and derivatives, with activities toward one or more of the PACAP/VIP receptors, including all of their various isoforms. Also provided are pharmaceutical compositions of one or more PACAP-like compounds, either alone or in combination with one or more other prophylactic/therapeutic agents useful for treating, managing, or preventing injury to the kidney of a mammal (e.g., a human) undergoing treatment with one or more iodinated radiocontrast media. Also featured is an in vivo mouse model for testing the efficacy of cytoprotective agents against contrast-induced nephropathy.

16 Claims, 19 Drawing Sheets

His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys-NH$_2$ (SEQ ID NO:1)

His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-NH$_2$ (SEQ ID NO:2)

His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn-NH$_2$ (SEQ ID NO:3)

His-D-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys-NH$_2$ (SEQ ID NO:4)

His-Aib-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys-NH$_2$ (SEQ ID NO:5)

His-D-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys-NH$_2$ (SEQ ID NO:6)
   |
  CO(CH$_2$)$_{14}$CH$_3$

His-Ser-Asp-Gly-Ile-Phe-Thr-Asp-Ser-Tyr-Ser-Arg-Tyr-Arg-Lys-Gln-Met-Ala-Val-Lys-Lys-Ala-Leu-Ala-Ala-Val-Leu-Gly-Lys-Arg-Tyr-Lys-Gln-Arg-Val-Lys-Asn-Lys-NH$_2$ (SEQ ID NO:8)

His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Lys-Val-Lys-Asn-Lys-NH$_2$ (SEQ ID NO:10)

N-acetyl-His-Ser-Pip-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys-NH$_2$ (SEQ ID NO:38)

His-Ser-Pip-Gly-Ile-Phe-Thr-Asp-Ser-Tyr-Ser-Arg-Tyr-Ala-Lys-Aib-Ala-Ala-Val-Lys-Lys-Tyr-Leu-Ala-Ala-Val-Leu-Aib-Lys-Arg-Tyr-Lys-Gln-Lys-Val-Lys-Asn-D-Lys-NH$_2$ (SEQ ID NO:39)

His-Ser-Pip-Gly-Ile-Phe-Thr-Asp-Ser-Tyr-Ser-Arg-Tyr-Arg-Ala-Aib-Ala-Ala-Val-Lys-Lys-Tyr-Leu-Ala-Ala-Val-Leu-Aib-Lys-Arg-Tyr-Lys-Gln-Lys-Val-Lys-Asn-D-Lys-NH$_2$ (SEQ ID NO:40)

Figure 1

SEQUENCE LISTING

```
<160> NUMBER OF SEQ ID NOS: 76

<210> SEQ ID NO 1
<211> LENGTH: 38
<212> TYPE: PRT
<213> ORGANISM: Homo sapiens
<220> FEATURE:
<221> NAME/KEY: MOD_RES
<222> LOCATION: (38)..(38)
```

-continued

```
<223> OTHER INFORMATION: AMIDATION

<400> SEQUENCE: 1

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 2
<211> LENGTH: 27
<212> TYPE: PRT
<213> ORGANISM: Homo sapiens
<220> FEATURE:
<221> NAME/KEY: MOD_RES
<222> LOCATION: (27)..(27)
<223> OTHER INFORMATION: AMIDATION

<400> SEQUENCE: 2

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 3
<211> LENGTH: 28
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: AMIDATION

<400> SEQUENCE: 3

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 4
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (38)..(38)
<223> OTHER INFORMATION: AMIDATION

<400> SEQUENCE: 4

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 5
<211> LENGTH: 38
```

```
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MOD_RES
<222> LOCATION: (38)..(38)
<223> OTHER INFORMATION: AMIDATION

<400> SEQUENCE: 5

His Xaa Asp Gly Ile Phe Thr Asp Ser Tyr Ser Arg Tyr Arg Lys Gln
 1               5                  10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 6
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (38)..(38)
<223> OTHER INFORMATION: AMIDATION
<220> FEATURE:
<221> NAME/KEY: LIPID
<222> LOCATION: (38)..(38)
<223> OTHER INFORMATION: N-epsilon-palmitoyl-Lys

<400> SEQUENCE: 6

His Ser Asp Gly Ile Phe Thr Asp Ser Tyr Ser Arg Tyr Arg Lys Gln
 1               5                  10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 7
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MOD_RES
<222> LOCATION: (38)..(38)
<223> OTHER INFORMATION: AMIDATION
<220> FEATURE:
<221> NAME/KEY: LIPID
<222> LOCATION: (38)..(38)
<223> OTHER INFORMATION: N-epsilon-palmitoyl-Lys

<400> SEQUENCE: 7

His Xaa Asp Gly Ile Phe Thr Asp Ser Tyr Ser Arg Tyr Arg Lys Gln
 1               5                  10                  15

Met Ala Val Lys Lys Tyr Leu Ala Ala Val Leu Gly Lys Arg Tyr Lys
            20                  25                  30
```

Gln Arg Val Lys Asn Lys
        35

<210> SEQ ID NO 8
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (38)..(38)
<223> OTHER INFORMATION: AMIDATION

<400> SEQUENCE: 8

His Ser Asp Gly Ile Phe Thr Asp Ser Tyr Ser Arg Tyr Arg Lys Gln
1               5                   10                  15

Met Ala Val Lys Lys Ala Leu Ala Ala Val Leu Gly Lys Arg Tyr Lys
            20                  25                  30

Gln Arg Val Lys Asn Lys
        35

<210> SEQ ID NO 9
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (38)..(38)
<223> OTHER INFORMATION: AMIDATION
<220> FEATURE:
<221> NAME/KEY: MOD_RES
<222> LOCATION: (38)..(38)
<223> OTHER INFORMATION: D-Lys

<400> SEQUENCE: 9

His Ser Asp Gly Ile Phe Thr Asp Ser Tyr Ser Arg Tyr Arg Lys Ala
1               5                   10                  15

Ala Ala Val Lys Lys Tyr Leu Ala Ala Val Leu Gly Lys Arg Tyr Lys
            20                  25                  30

Gln Arg Val Lys Asn Lys
        35

<210> SEQ ID NO 10
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (38)..(38)
<223> OTHER INFORMATION: AMIDATION

<400> SEQUENCE: 10

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Lys Val Lys Asn Lys
        35

<210> SEQ ID NO 11
<211> LENGTH: 38

-continued

```
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (38)..(38)
<223> OTHER INFORMATION: AMIDATION
<220> FEATURE:
<221> NAME/KEY: LIPID
<222> LOCATION: (38)..(38)
<223> OTHER INFORMATION: N-epsilon-palmitoyl-Lys

<400> SEQUENCE: 11

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 12
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (38)..(38)
<223> OTHER INFORMATION: AMIDATION
<220> FEATURE:
<221> NAME/KEY: MOD_RES
<222> LOCATION: (38)..(38)
<223> OTHER INFORMATION: D-Lys

<400> SEQUENCE: 12

His Ser Asp Gly Ile Phe Thr Asp Ser Tyr Ser Arg Tyr Arg Lys Ala
1               5                   10                  15

Ala Ala Val Lys Lys Tyr Leu Ala Ala Val Leu Gly Lys Arg Tyr Lys
            20                  25                  30

Gln Arg Val Lys Asn Lys
        35

<210> SEQ ID NO 13
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MOD_RES
<222> LOCATION: (38)..(38)
<223> OTHER INFORMATION: AMIDATION
<220> FEATURE:
<221> NAME/KEY: MOD_RES
<222> LOCATION: (38)..(38)
<223> OTHER INFORMATION: D-Lys

<400> SEQUENCE: 13

His Xaa Asp Gly Ile Phe Thr Asp Ser Tyr Ser Arg Tyr Arg Lys Ala
1               5                   10                  15
```

```
Ala Ala Val Lys Lys Tyr Leu Ala Ala Val Leu Gly Lys Arg Tyr Lys
        20                  25                  30

Gln Arg Val Lys Asn Lys
        35

<210> SEQ ID NO 14
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (38)..(38)
<223> OTHER INFORMATION: AMIDATION

<400> SEQUENCE: 14

His Ala Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
        20                  25                  30

Gln Arg Val Lys Asn Lys
        35

<210> SEQ ID NO 15
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: MISC_FEATURE
<222> LOCATION: (17)..(17)
<223> OTHER INFORMATION: Xaa is norleucine
<220> FEATURE:
<221> NAME/KEY: MOD_RES
<222> LOCATION: (38)..(38)
<223> OTHER INFORMATION: AMIDATION

<400> SEQUENCE: 15

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
        20                  25                  30

Gln Arg Val Lys Asn Lys
        35

<210> SEQ ID NO 16
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (17)..(17)
```

```
<223> OTHER INFORMATION: Xaa is norleucine
<220> FEATURE:
<221> NAME/KEY: MOD_RES
<222> LOCATION: (38)..(38)
<223> OTHER INFORMATION: AMIDATION

<400> SEQUENCE: 16

His Xaa Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln Arg Val Lys Asn Lys
        35

<210> SEQ ID NO 17
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (17)..(17)
<223> OTHER INFORMATION: Xaa is norleucine
<220> FEATURE:
<221> NAME/KEY: MOD_RES
<222> LOCATION: (38)..(38)
<223> OTHER INFORMATION: AMIDATION

<400> SEQUENCE: 17

His Ala Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln Arg Val Lys Asn Lys
        35

<210> SEQ ID NO 18
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (38)..(38)
<223> OTHER INFORMATION: AMIDATION

<400> SEQUENCE: 18

His Ser Asp Gly Ile Phe Thr Asp Ser Tyr Ser Arg Tyr Arg Lys Gln
1               5                   10                  15

Ala Ala Val Lys Lys Tyr Leu Ala Ala Val Leu Gly Lys Arg Tyr Lys
            20                  25                  30

Gln Arg Val Lys Asn Lys
        35

<210> SEQ ID NO 19
<211> LENGTH: 38
<212> TYPE: PRT
```

```
<213> ORGANISM: Artificial Sequence
<220> FEATURE:
<223> OTHER INFORMATION: Modification of Homo Sapien sequences
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MOD_RES
<222> LOCATION: (38)..(38)
<223> OTHER INFORMATION: AMIDATION

<400> SEQUENCE: 19

His Xaa Asp Gly Ile Phe Thr Asp Ser Tyr Ser Arg Tyr Arg Lys Gln
1               5                   10                  15

Ala Ala Val Lys Lys Tyr Leu Ala Ala Val Leu Gly Lys Arg Tyr Lys
            20                  25                  30

Gln Arg Val Lys Asn Lys
        35

<210> SEQ ID NO 20
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (38)..(38)
<223> OTHER INFORMATION: AMIDATION

<400> SEQUENCE: 20

His Ala Asp Gly Ile Phe Thr Asp Ser Tyr Ser Arg Tyr Arg Lys Gln
1               5                   10                  15

Ala Ala Val Lys Lys Tyr Leu Ala Ala Val Leu Gly Lys Arg Tyr Lys
            20                  25                  30

Gln Arg Val Lys Asn Lys
        35

<210> SEQ ID NO 21
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: LIPID
<222> LOCATION: (36)..(36)
<223> OTHER INFORMATION: N-epsilon-palmitoyl-Lys
<220> FEATURE:
<221> NAME/KEY: MOD_RES
<222> LOCATION: (38)..(38)
<223> OTHER INFORMATION: AMIDATION

<400> SEQUENCE: 21

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 22
```

```
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: LIPID
<222> LOCATION: (32)..(32)
<223> OTHER INFORMATION: N-epsilon-palmitoyl-Lys
<220> FEATURE:
<221> NAME/KEY: MOD_RES
<222> LOCATION: (38)..(38)
<223> OTHER INFORMATION: AMIDATION

<400> SEQUENCE: 22

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 23
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: LIPID
<222> LOCATION: (29)..(29)
<223> OTHER INFORMATION: N-epsilon-palmitoyl-Lys
<220> FEATURE:
<221> NAME/KEY: MOD_RES
<222> LOCATION: (38)..(38)
<223> OTHER INFORMATION: AMIDATION

<400> SEQUENCE: 23

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 24
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: LIPID
<222> LOCATION: (36)..(36)
<223> OTHER INFORMATION: N-epsilon-palmitoyl-Lys
<220> FEATURE:
<221> NAME/KEY: MOD_RES
<222> LOCATION: (38)..(38)
<223> OTHER INFORMATION: AMIDATION

<400> SEQUENCE: 24

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30
```

-continued

Gln Arg Val Lys Asn Lys
        35

<210> SEQ ID NO 25
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: LIPID
<222> LOCATION: (32)..(32)
<223> OTHER INFORMATION: N-epsilon-palmitoyl-Lys
<220> FEATURE:
<221> NAME/KEY: MOD_RES
<222> LOCATION: (38)..(38)
<223> OTHER INFORMATION: AMIDATION

<400> SEQUENCE: 25

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 26
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: LIPID
<222> LOCATION: (29)..(29)
<223> OTHER INFORMATION: N-epsilon-palmitoyl-Lys
<220> FEATURE:
<221> NAME/KEY: MOD_RES
<222> LOCATION: (38)..(38)
<223> OTHER INFORMATION: AMIDATION

<400> SEQUENCE: 26

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 27
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: LIPID

```
<222> LOCATION: (36)..(36)
<223> OTHER INFORMATION: N-epsilon-palmitoyl-Lys
<220> FEATURE:
<221> NAME/KEY: MOD_RES
<222> LOCATION: (38)..(38)
<223> OTHER INFORMATION: AMIDATION

<400> SEQUENCE: 27

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 28
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: LIPID
<222> LOCATION: (32)..(32)
<223> OTHER INFORMATION: N-epsilon-palmitoyl-Lys
<220> FEATURE:
<221> NAME/KEY: MOD_RES
<222> LOCATION: (38)..(38)
<223> OTHER INFORMATION: AMIDATION

<400> SEQUENCE: 28

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 29
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: LIPID
<222> LOCATION: (29)..(29)
<223> OTHER INFORMATION: CO(CH2)14CH3
<220> FEATURE:
<221> NAME/KEY: MOD_RES
<222> LOCATION: (38)..(38)
<223> OTHER INFORMATION: AMIDATION

<400> SEQUENCE: 29

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35
```

```
<210> SEQ ID NO 30
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (38)..(38)
<223> OTHER INFORMATION: AMIDATION

<400> SEQUENCE: 30
```

His Ser Asp Gly Ile Phe Thr Asp Ser Tyr Ser Arg Tyr Ala Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

```
<210> SEQ ID NO 31
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (38)..(38)
<223> OTHER INFORMATION: AMIDATION

<400> SEQUENCE: 31
```

His Ser Asp Gly Ile Phe Thr Asp Ser Tyr Ser Arg Tyr Arg Lys Gln
1               5                   10                  15

Met Ala Val Ala Lys Tyr Leu Ala Ala Val Leu Gly Lys Arg Tyr Lys
            20                  25                  30

Gln Arg Val Lys Asn Lys
        35

```
<210> SEQ ID NO 32
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (38)..(38)
<223> OTHER INFORMATION: AMIDATION

<400> SEQUENCE: 32
```

His Ser Asp Gly Ile Phe Thr Asp Ser Tyr Ser Arg Tyr Arg Lys Gln
1               5                   10                  15

Met Ala Val Lys Ala Tyr Leu Ala Ala Val Leu Gly Lys Arg Tyr Lys
            20                  25                  30

Gln Arg Val Lys Asn Lys
        35

```
<210> SEQ ID NO 33
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
```

```
<222> LOCATION: (2)..(2)
<223> OTHER INFORMATION: D-Ser
<220> FEATURE:
<221> NAME/KEY: MOD_RES
<222> LOCATION: (38)..(38)
<223> OTHER INFORMATION: AMIDATION

<400> SEQUENCE: 33

His Ser Asp Gly Ile Phe Thr Asp Ser Tyr Ser Arg Tyr Ala Lys Gln
1               5                   10                  15
Met Ala Val Lys Lys Tyr Leu Ala Ala Val Leu Gly Lys Arg Tyr Lys
            20                  25                  30
Gln Arg Val Lys Asn Lys
        35

<210> SEQ ID NO 34
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (38)..(38)
<223> OTHER INFORMATION: AMIDATION

<400> SEQUENCE: 34

His Ser Asp Gly Ile Phe Thr Asp Ser Tyr Ser Arg Tyr Arg Lys Gln
1               5                   10                  15
Met Ala Val Ala Lys Tyr Leu Ala Ala Val Leu Gly Lys Arg Tyr Lys
            20                  25                  30
Gln Arg Val Lys Asn Lys
        35

<210> SEQ ID NO 35
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (38)..(38)
<223> OTHER INFORMATION: AMIDATION

<400> SEQUENCE: 35

His Ser Asp Gly Ile Phe Thr Asp Ser Tyr Ser Arg Tyr Arg Lys Gln
1               5                   10                  15
Met Ala Val Lys Ala Tyr Leu Ala Ala Val Leu Gly Lys Arg Tyr Lys
            20                  25                  30
Gln Arg Val Lys Asn Lys
        35

<210> SEQ ID NO 36
<211> LENGTH: 38
<212> TYPE: PRT
<213> ORGANISM: Artificial Sequence
<220> FEATURE:
<223> OTHER INFORMATION: Modification of Homo Sapien sequences
```

```
<220> FEATURE:
<221> NAME/KEY: MOD_RES
<222> LOCATION: (38)..(38)
<223> OTHER INFORMATION: AMIDATION

<400> SEQUENCE: 36

His Ser Asp Gly Ile Phe Thr Asp Ser Tyr Ser Arg Tyr Ala Lys Gln
1               5                   10                  15

Met Ala Val Ala Lys Tyr Leu Ala Ala Val Leu Gly Lys Arg Tyr Lys
            20                  25                  30

Gln Arg Val Lys Asn Lys
        35

<210> SEQ ID NO 37
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MISC_FEATURE
<222> LOCATION: (3)..(3)
<223> OTHER INFORMATION: Xaa is pipecolic acid (piperidine-2-carboxylic
      acid).
<220> FEATURE:
<221> NAME/KEY: MOD_RES
<222> LOCATION: (38)..(38)
<223> OTHER INFORMATION: AMIDATION

<400> SEQUENCE: 37

His Ser Xaa Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 38
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is pipecolic acid (piperidine-2-carboxylic
      acid)
<220> FEATURE:
<221> NAME/KEY: MOD_RES
<222> LOCATION: (38)..(38)
<223> OTHER INFORMATION: AMIDATION

<400> SEQUENCE: 38

His Ser Xaa Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 39
<211> LENGTH: 38
```

```
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MISC_FEATURE
<222> LOCATION: (3)..(3)
<223> OTHER INFORMATION: Xaa is pipecolic acid (piperidine-2-carboxylic
      acid)
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (28)..(28)
<223> OTHER INFORMATION: Xaa is alpha-aminoisobutyric acid
<220> FEATURE:
<221> NAME/KEY: MOD_RES
<222> LOCATION: (38)..(38)
<223> OTHER INFORMATION: AMIDATION
<220> FEATURE:
<221> NAME/KEY: MOD_RES
<222> LOCATION: (38)..(38)
<223> OTHER INFORMATION: D-Lys

<400> SEQUENCE: 39

His Ser Xaa Gly Ile Phe Thr Asp Ser Tyr Ser Arg Tyr Ala Lys Xaa
1               5                   10                  15

Ala Ala Val Lys Lys Tyr Leu Ala Ala Val Leu Xaa Lys Arg Tyr Lys
            20                  25                  30

Gln Lys Val Lys Asn Lys
        35

<210> SEQ ID NO 40
<211> LENGTH: 38
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MISC_FEATURE
<222> LOCATION: (3)..(3)
<223> OTHER INFORMATION: Xaa is pipecolic acid (piperidine-2-carboxylic
      acid)
<220> FEATURE:
<221> NAME/KEY: MISC_FEATURE
<222> LOCATION: (16)..(16)
<223> OTHER INFORMATION: Xaa is alpha-aminoisobutyric acid
<220> FEATURE:
<221> NAME/KEY: MISC_FEATURE
<222> LOCATION: (28)..(28)
<223> OTHER INFORMATION: Xaa is alpha-aminoisobutyric acid
<220> FEATURE:
<221> NAME/KEY: MOD_RES
<222> LOCATION: (38)..(38)
<223> OTHER INFORMATION: AMIDATION

<400> SEQUENCE: 40

His Ser Xaa Gly Ile Phe Thr Asp Ser Tyr Ser Arg Tyr Arg Ala Xaa
1               5                   10                  15

Ala Ala Val Lys Lys Tyr Leu Ala Ala Val Leu Xaa Lys Arg Tyr Lys
            20                  25                  30

Gln Lys Val Lys Asn Lys
        35

<210> SEQ ID NO 41
<211> LENGTH: 27
<212> TYPE: PRT
<213> ORGANISM: Artificial Sequence
<220> FEATURE:
```

```
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (27)..(27)
<223> OTHER INFORMATION: AMIDATION

<400> SEQUENCE: 41

His Ser Asp Gly Ile Phe Thr Asp Ser Tyr Ser Arg Tyr Arg Lys Gln
 1               5                  10                  15

Met Ala Val Lys Lys Tyr Leu Ala Ala Val Leu
            20                  25

<210> SEQ ID NO 42
<211> LENGTH: 27
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MOD_RES
<222> LOCATION: (27)..(27)
<223> OTHER INFORMATION: AMIDATION

<400> SEQUENCE: 42

His Xaa Asp Gly Ile Phe Thr Asp Ser Tyr Ser Arg Tyr Arg Lys Gln
 1               5                  10                  15

Met Ala Val Lys Lys Tyr Leu Ala Ala Val Leu
            20                  25

<210> SEQ ID NO 43
<211> LENGTH: 27
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (27)..(27)
<223> OTHER INFORMATION: AMIDATION

<400> SEQUENCE: 43

His Ser Asp Gly Ile Phe Thr Asp Ser Tyr Ser Arg Tyr Arg Lys Gln
 1               5                  10                  15

Met Ala Val Lys Lys Ala Leu Ala Ala Val Leu
            20                  25

<210> SEQ ID NO 44
<211> LENGTH: 27
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (27)..(27)
<223> OTHER INFORMATION: AMIDATION

<400> SEQUENCE: 44
```

```
His Ala Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 45
<211> LENGTH: 27
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: MISC_FEATURE
<222> LOCATION: (17)..(17)
<223> OTHER INFORMATION: Xaa is norleucine
<220> FEATURE:
<221> NAME/KEY: MOD_RES
<222> LOCATION: (27)..(27)
<223> OTHER INFORMATION: AMIDATION

<400> SEQUENCE: 45

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu
            20                  25

<210> SEQ ID NO 46
<211> LENGTH: 27
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE
<222> LOCATION: (17)..(17)
<223> OTHER INFORMATION: Xaa is norleucine
<220> FEATURE:
<221> NAME/KEY: MOD_RES
<222> LOCATION: (27)..(27)
<223> OTHER INFORMATION: AMIDATION

<400> SEQUENCE: 46

His Xaa Asp Gly Ile Phe Thr Asp Ser Tyr Ser Arg Tyr Arg Lys Gln
1               5                   10                  15

Xaa Ala Val Lys Lys Tyr Leu Ala Ala Val Leu
            20                  25

<210> SEQ ID NO 47
<211> LENGTH: 27
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (17)..(17)
<223> OTHER INFORMATION: Xaa is norleucine
<220> FEATURE:
```

```
<221> NAME/KEY: MOD_RES
<222> LOCATION: (27)..(27)
<223> OTHER INFORMATION: AMIDATION

<400> SEQUENCE: 47

His Ala Asp Gly Ile Phe Thr Asp Ser Tyr Ser Arg Tyr Arg Lys Gln
1               5                   10                  15

Xaa Ala Val Lys Lys Tyr Leu Ala Ala Val Leu
            20                  25

<210> SEQ ID NO 48
<211> LENGTH: 27
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (27)..(27)
<223> OTHER INFORMATION: AMIDATION

<400> SEQUENCE: 48

His Ser Asp Gly Ile Phe Thr Asp Ser Tyr Ser Arg Tyr Arg Lys Gln
1               5                   10                  15

Ala Ala Val Lys Lys Tyr Leu Ala Ala Val Leu
            20                  25

<210> SEQ ID NO 49
<211> LENGTH: 27
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MOD_RES
<222> LOCATION: (27)..(27)
<223> OTHER INFORMATION: AMIDATION

<400> SEQUENCE: 49

His Xaa Asp Gly Ile Phe Thr Asp Ser Tyr Ser Arg Tyr Arg Lys Gln
1               5                   10                  15

Ala Ala Val Lys Lys Tyr Leu Ala Ala Val Leu
            20                  25

<210> SEQ ID NO 50
<211> LENGTH: 27
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (27)..(27)
<223> OTHER INFORMATION: AMIDATION

<400> SEQUENCE: 50

His Ala Asp Gly Ile Phe Thr Asp Ser Tyr Ser Arg Tyr Arg Lys Gln
```

```
                1               5                  10                 15
Ala Ala Val Lys Lys Tyr Leu Ala Ala Val Leu
            20                 25

<210> SEQ ID NO 51
<211> LENGTH: 27
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (27)..(27)
<223> OTHER INFORMATION: AMIDATION
<220> FEATURE:
<221> NAME/KEY: MOD_RES
<222> LOCATION: (27)..(27)
<223> OTHER INFORMATION: D-Leu

<400> SEQUENCE: 51

His Ser Asp Gly Ile Phe Thr Asp Ser Tyr Ser Arg Tyr Arg Lys Gln
1               5                  10                 15

Met Ala Val Lys Lys Tyr Leu Ala Ala Val Leu
            20                 25

<210> SEQ ID NO 52
<211> LENGTH: 27
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MOD_RES
<222> LOCATION: (27)..(27)
<223> OTHER INFORMATION: AMIDATION
<220> FEATURE:
<221> NAME/KEY: MOD_RES
<222> LOCATION: (27)..(27)
<223> OTHER INFORMATION: D-Leu

<400> SEQUENCE: 52

His Xaa Asp Gly Ile Phe Thr Asp Ser Tyr Ser Arg Tyr Arg Lys Gln
1               5                  10                 15

Met Ala Val Lys Lys Tyr Leu Ala Ala Val Leu
            20                 25

<210> SEQ ID NO 53
<211> LENGTH: 27
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (27)..(27)
<223> OTHER INFORMATION: AMIDATION
<220> FEATURE:
<221> NAME/KEY: MOD_RES
<222> LOCATION: (27)..(27)
<223> OTHER INFORMATION: D-Leu

<400> SEQUENCE: 53
```

His Ser Asp Gly Ile Phe Thr Asp Ser Tyr Ser Arg Tyr Arg Lys Gln
1               5                   10                  15

Met Ala Val Lys Lys Ala Leu Ala Ala Val Leu
            20                  25

<210> SEQ ID NO 54
<211> LENGTH: 27
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (27)..(27)
<223> OTHER INFORMATION: AMIDATION
<220> FEATURE:
<221> NAME/KEY: MOD_RES
<222> LOCATION: (27)..(27)
<223> OTHER INFORMATION: D-Leu

<400> SEQUENCE: 54

His Ala Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 55
<211> LENGTH: 27
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: MISC_FEATURE
<222> LOCATION: (17)..(17)
<223> OTHER INFORMATION: Xaa is norleucine
<220> FEATURE:
<221> NAME/KEY: MOD_RES
<222> LOCATION: (27)..(27)
<223> OTHER INFORMATION: AMIDATION
<220> FEATURE:
<221> NAME/KEY: MOD_RES
<222> LOCATION: (27)..(27)
<223> OTHER INFORMATION: D-Leu

<400> SEQUENCE: 55

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu
            20                  25

<210> SEQ ID NO 56
<211> LENGTH: 27
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MISC_FEATURE -continued

```
<222> LOCATION: (17)..(17)
<223> OTHER INFORMATION: Xaa is norleucine
<220> FEATURE:
<221> NAME/KEY: MOD_RES
<222> LOCATION: (27)..(27)
<223> OTHER INFORMATION: AMIDATION
<220> FEATURE:
<221> NAME/KEY: MOD_RES
<222> LOCATION: (27)..(27)
<223> OTHER INFORMATION: D-Leu

<400> SEQUENCE: 56

His Xaa Asp Gly Ile Phe Thr Asp Ser Tyr Ser Arg Tyr Arg Lys Gln
1               5                   10                  15

Xaa Ala Val Lys Lys Tyr Leu Ala Ala Val Leu
            20                  25

<210> SEQ ID NO 57
<211> LENGTH: 27
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (17)..(17)
<223> OTHER INFORMATION: Xaa is norleucine
<220> FEATURE:
<221> NAME/KEY: MOD_RES
<222> LOCATION: (27)..(27)
<223> OTHER INFORMATION: AMIDATION
<220> FEATURE:
<221> NAME/KEY: MOD_RES
<222> LOCATION: (27)..(27)
<223> OTHER INFORMATION: D-Leu

<400> SEQUENCE: 57

His Ala Asp Gly Ile Phe Thr Asp Ser Tyr Ser Arg Tyr Arg Lys Gln
1               5                   10                  15

Xaa Ala Val Lys Lys Tyr Leu Ala Ala Val Leu
            20                  25

<210> SEQ ID NO 58
<211> LENGTH: 27
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (27)..(27)
<223> OTHER INFORMATION: AMIDATION
<220> FEATURE:
<221> NAME/KEY: MOD_RES
<222> LOCATION: (27)..(27)
<223> OTHER INFORMATION: D-Leu

<400> SEQUENCE: 58

His Ser Asp Gly Ile Phe Thr Asp Ser Tyr Ser Arg Tyr Arg Lys Gln
1               5                   10                  15

Ala Ala Val Lys Lys Tyr Leu Ala Ala Val Leu
            20                  25
```

<210> SEQ ID NO 59
<211> LENGTH: 27
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MOD_RES
<222> LOCATION: (27)..(27)
<223> OTHER INFORMATION: AMIDATION
<220> FEATURE:
<221> NAME/KEY: MOD_RES
<222> LOCATION: (27)..(27)
<223> OTHER INFORMATION: D-Leu

<400> SEQUENCE: 59

His Xaa Asp Gly Ile Phe Thr Asp Ser Tyr Ser Arg Tyr Arg Lys Gln
1               5                   10                  15

Ala Ala Val Lys Lys Tyr Leu Ala Ala Val Leu
            20                  25

<210> SEQ ID NO 60
<211> LENGTH: 27
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (27)..(27)
<223> OTHER INFORMATION: AMIDATION
<220> FEATURE:
<221> NAME/KEY: MOD_RES
<222> LOCATION: (27)..(27)
<223> OTHER INFORMATION: D-Leu

<400> SEQUENCE: 60

His Ala Asp Gly Ile Phe Thr Asp Ser Tyr Ser Arg Tyr Arg Lys Gln
1               5                   10                  15

Ala Ala Val Lys Lys Tyr Leu Ala Ala Val Leu
            20                  25

<210> SEQ ID NO 61
<211> LENGTH: 28
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (28)..(28)
<223> OTHER INFORMATION: AMIDATION

<400> SEQUENCE: 61

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

```
<210> SEQ ID NO 62
<211> LENGTH: 28
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MOD_RES
<222> LOCATION: (28)..(28)
<223> OTHER INFORMATION: AMIDATION

<400> SEQUENCE: 62

His Xaa Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 63
<211> LENGTH: 28
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (28)..(28)
<223> OTHER INFORMATION: AMIDATION

<400> SEQUENCE: 63

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 64
<211> LENGTH: 28
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (28)..(28)
<223> OTHER INFORMATION: AMIDATION

<400> SEQUENCE: 64

His Ala Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 65
<211> LENGTH: 28
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
```

```
<223> OTHER INFORMATION: D-Ser
<220> FEATURE:
<221> NAME/KEY: MISC_FEATURE
<222> LOCATION: (17)..(17)
<223> OTHER INFORMATION: Xaa is norleucine
<220> FEATURE:
<221> NAME/KEY: MOD_RES
<222> LOCATION: (28)..(28)
<223> OTHER INFORMATION: AMIDATION

<400> SEQUENCE: 65

His Ser Asp Ala Val Phe Thr Asp Asn Tyr Thr Arg Leu Arg Lys Gln
1               5                   10                  15

Xaa Ala Val Lys Lys Tyr Leu Asn Ser Ile Leu Asn
            20                  25

<210> SEQ ID NO 66
<211> LENGTH: 28
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MISC_FEATURE
<222> LOCATION: (2)..(2)
<223> OTHER INFORMATION: Xaa is alpha-aminoisobtyric acid
<220> FEATURE:
<221> NAME/KEY: MISC_FEATURE
<222> LOCATION: (17)..(17)
<223> OTHER INFORMATION: Xaa is norleucine
<220> FEATURE:
<221> NAME/KEY: MOD_RES
<222> LOCATION: (28)..(28)
<223> OTHER INFORMATION: AMIDATION

<400> SEQUENCE: 66

His Xaa Asp Ala Val Phe Thr Asp Asn Tyr Thr Arg Leu Arg Lys Gln
1               5                   10                  15

Xaa Ala Val Lys Lys Tyr Leu Asn Ser Ile Leu Asn
            20                  25

<210> SEQ ID NO 67
<211> LENGTH: 28
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (17)..(17)
<223> OTHER INFORMATION: Xaa is norleucine
<220> FEATURE:
<221> NAME/KEY: MOD_RES
<222> LOCATION: (28)..(28)
<223> OTHER INFORMATION: AMIDATION

<400> SEQUENCE: 67

His Ala Asp Ala Val Phe Thr Asp Asn Tyr Thr Arg Leu Arg Lys Gln
1               5                   10                  15

Xaa Ala Val Lys Lys Tyr Leu Asn Ser Ile Leu Asn
            20                  25

<210> SEQ ID NO 68
<211> LENGTH: 28
<212> TYPE: PRT
<213> ORGANISM: Artificial Sequence
```

```
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (28)..(28)
<223> OTHER INFORMATION: AMIDATION

<400> SEQUENCE: 68

His Ser Asp Ala Val Phe Thr Asp Asn Tyr Thr Arg Leu Arg Lys Gln
1               5                   10                  15

Ala Ala Val Lys Lys Tyr Leu Asn Ser Ile Leu Asn
            20                  25

<210> SEQ ID NO 69
<211> LENGTH: 28
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MISC_FEATURE
<222> LOCATION: (2)..(2)
<223> OTHER INFORMATION: Xaa is alpha-aminoisobutyric acid
<220> FEATURE:
<221> NAME/KEY: MOD_RES
<222> LOCATION: (28)..(28)
<223> OTHER INFORMATION: AMIDATION

<400> SEQUENCE: 69

His Xaa Asp Ala Val Phe Thr Asp Asn Tyr Thr Arg Leu Arg Lys Gln
1               5                   10                  15

Ala Ala Val Lys Lys Tyr Leu Asn Ser Ile Leu Asn
            20                  25

<210> SEQ ID NO 70
<211> LENGTH: 28
<212> TYPE: PRT
<213> ORGANISM: Artificial Sequence
<220> FEATURE:
<223> OTHER INFORMATION: Modification of Homo Sapien sequences
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (28)..(28)
<223> OTHER INFORMATION: AMIDATION

<400> SEQUENCE: 70

His Ala Asp Ala Val Phe Thr Asp Asn Tyr Thr Arg Leu Arg Lys Gln
1               5                   10                  15

Ala Ala Val Lys Lys Tyr Leu Asn Ser Ile Leu Asn
            20                  25

<210> SEQ ID NO 71
<211> LENGTH: 38
<212> TYPE: PRT
<213> ORGANISM: Podarcis sicula
<220> FEATURE:
<221> NAME/KEY: MOD_RES
<222> LOCATION: (38)..(38)
<223> OTHER INFORMATION: AMIDATION

<400> SEQUENCE: 71
```

```
His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Arg Tyr Lys
            20                  25                  30

Gln Arg Val Arg Asn Lys
        35
```

<210> SEQ ID NO 72
<211> LENGTH: 38
<212> TYPE: PRT
<213> ORGANISM: Gallus domesticus
<220> FEATURE:
<221> NAME/KEY: MOD_RES
<222> LOCATION: (38)..(38)
<223> OTHER INFORMATION: AMIDATION

<400> SEQUENCE: 72

```
His Ile Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Leu Arg Tyr Lys
            20                  25                  30

Gln Arg Val Lys Asn Lys
        35
```

<210> SEQ ID NO 73
<211> LENGTH: 38
<212> TYPE: PRT
<213> ORGANISM: Rana ridibunda and Xenopus laevis
<220> FEATURE:
<221> NAME/KEY: MOD_RES
<222> LOCATION: (38)..(38)
<223> OTHER INFORMATION: AMIDATION

<400> SEQUENCE: 73

```
His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Ile Lys Asn Lys
        35
```

<210> SEQ ID NO 74
<211> LENGTH: 38
<212> TYPE: PRT
<213> ORGANISM: Oncorhynchus nerka
<220> FEATURE:
<221> NAME/KEY: MOD_RES
<222> LOCATION: (38)..(38)
<223> OTHER INFORMATION: AMIDATION

<400> SEQUENCE: 74

```
His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Arg
            20                  25                  30

Gln Arg Tyr Arg Asn Lys
        35
```

<210> SEQ ID NO 75
<211> LENGTH: 38
<212> TYPE: PRT
<213> ORGANISM: Ictalurus punctatus
<220> FEATURE:
<221> NAME/KEY: MOD_RES

```
<222> LOCATION: (38)..(38)
<223> OTHER INFORMATION: AMIDATION

<400> SEQUENCE: 75

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Arg Arg Tyr Arg
            20                  25                  30

Gln Arg Phe Arg Asn Lys
        35

<210> SEQ ID NO 76
<211> LENGTH: 61
<212> TYPE: PRT
<213> ORGANISM: Lutzomyia longipalpis
<220> FEATURE:
<221> NAME/KEY: MISC_FEATURE
<222> LOCATION: (1)..(5)
<223> OTHER INFORMATION: cyclo
<220> FEATURE:
<221> NAME/KEY: MISC_FEATURE
<222> LOCATION: (14)..(51)
<223> OTHER INFORMATION: cyclo
<220> FEATURE:
<221> NAME/KEY: MOD_RES
<222> LOCATION: (38)..(38)
<223> OTHER INFORMATION: AMIDATION

<400> SEQUENCE: 76

Cys Asp Ala Thr Cys Gln Phe Arg Lys Ala Ile Glu Asp Cys Arg Lys
1               5                   10                  15

Lys Ala His His Ser Asp Val Leu Gln Thr Ser Val Gln Thr Thr Ala
            20                  25                  30

Thr Phe Thr Ser Met Asp Thr Ser Gln Leu Pro Gly Ser Gly Val Phe
        35                  40                  45

Lys Glu Cys Met Lys Gln Lys Ala Lys Glu Phe Lys Ala
    50                  55                  60
```

USE OF PITUITARY ADENYLATE CYCLASE-ACTIVATING POLYPEPTIDE (PACAP) AND PACAP ANALOGS FOR TREATING CONTRAST-INDUCED NEPHROPATHY

CROSS REFERENCE TO RELATED APPLICATIONS

This application claims benefit of U.S. Provisional Application No. 61/596,917 filed on Feb. 9, 2012, and U.S. Provisional Application No. 61/561,070 filed on Nov. 17, 2011.

FIELD OF THE INVENTION

This invention relates to methods and compositions for the treatment, management or prevention of injury to an organ (e.g., the kidney) of a human or other mammal caused by, or resulting from administration of, one or more iodinated radiocontrast media. The methods of this invention include the administration of an effective amount of one or more pituitary adenylate cyclase-activating polypeptide (PACAP)-like compounds, which includes native human PACAP38, native human PACAP27, native human vasoactive intestinal peptide (VIP), their agonists, analogs, fragments, and derivatives, with activities toward one or more of the PACAP/VIP receptors, including all of their various isoforms. This invention also provides pharmaceutical compositions of one or more PACAP-like compounds of the invention either alone or in combination with one or more other prophylactic/therapeutic agents useful for the treatment, management or prevention of injury to an organ, such as the kidney, of a human or other mammal undergoing a procedure that involves administration of one or more iodinated radiocontrast media. This invention also describes a novel in vivo mouse model for testing the efficacy of cytoprotective agents against contrast-induced nephropathy.

BACKGROUND OF THE INVENTION

Iodinated radiocontrast media are used to enhance the visualization of blood vessels and internal organs for a wide range of diagnostic and/or interventional procedures, including (but not limited to) angiography, urography, pyelography, arthrography, cholangiography, diskography, myelography, contrast-enhanced computer tomography, and cerebral ventriculography. Iodinated radiocontrast media are usually classified as ionic or nonionic. The nonionic radiocontrast media are organic compounds containing covalently bound iodine and are either monomeric or dimeric molecules with three or six atoms of iodine, respectively. Ionic iodinated radiocontrast media were developed before nonionic iodinated radiocontrast media. Both types of iodine-based contrast media are water soluble. Iodinated radiocontrast media are relatively safe drugs, but can cause serious anaphylactic reactions or contrast-induced nephropathy in some patients. The incidence of contrast-induced nephropathy in the general hospital population is low (1-2%), but can be above 50% in some hospital subpopulations, such as elderly diabetic patients with chronic kidney disease. Nonionic iodinated radiocontrast media are less nephrotoxic than ionic iodinated radiocontrast media. Contrast-induced nephropathy is the third leading cause of iatrogenic kidney failure (Thomsen et al., *Acta Radiol* 49:646-657, 2008). The risk factors for development of contrast-induced nephropathy include pre-existing kidney diseases, diabetes mellitus, hypertension, cardiovascular diseases, sickle cell anemia, gout flares, multiple myeloma, hypoalbuminemia, hypovolemia, and dehydration. Intravenous administration of iodinated radiocontrast media is less nephrotoxic than administration of the media into either the renal artery or the aorta proximal to the origin of the renal artery (Katzberg & Barrett, *Radiology* 243:622-628, 2007).

The iodinated radiocontrast media iodixanol (Visipaque), iohexol (Omnipaque), iopamidol (Isovue), iopentol (Imagopaque), iopromide (Ultravist), ioversol (Optiray), ioxilan (Oxilan), iothalamate (Conray), ioxaglate (Hexabrix), metrizamide (Amipaque), metrizoate (Isopaque), and sodium diatrizoate and meglumine diatrizoate (Urografin) have been approved by the U.S. Food and Drug Administration (FDA) for numerous diagnostic and/or interventional procedures. The iodinated radiocontrast media iobitridol (Xenetix), iodipamide (Bilignost), iomeprol (Iomeron), iotrolan (Isovist), and ioxithalamate (Telebrix) are used in the European Union.

The development of therapeutics for the treatment, management or prevention of injury to the kidney of humans or other mammals caused by one or more iodinated radiocontrast media has been hampered by the lack of a sensitive noninvasive method for detecting the earliest signs of kidney injury. Acute kidney injury in the clinic is usually diagnosed by determining the concentration of creatinine in serum. Contrast-induced nephropathy is usually defined as an increase in serum creatinine of more than 25% or an increase of more than 0.5 mg/dl within three days after the intravascular administration of contrast media that cannot be explain by other known causes. However, serum creatinine is an insensitive and nonspecific indicator of impaired kidney function. A large reduction in the glomerular filtration rate can occur before there is a detectable increase in serum creatinine. Urinary levels of kidney injury molecule 1 (KIM-1) and netrin-1 have been claimed to be more sensitive biomarkers for the earliest signs of kidney injury than serum levels of creatinine (Waanders et al., *J Pathol* 220:7-16, 2010; Ramesh et al., *Transplant Proc* 42:1519-1522, 2010). Nogo-B (reticulon 4B) is up-regulated in the proximal tubules of the mouse kidney following unilateral ureteral obstruction and ischemia/reperfusion, and Nogo-B mRNA levels have been suggested to be a sensitive indicator for diverse forms of renal proximal tubule injury (Marin et al., *Am J Pathol* 177:2765-2773, 2010).

The antioxidants N-acetylcysteine, vitamin E ($\alpha$-tocopherol) and ascorbic acid have been used as adjunctive cytoprotective agents with iodinated radiocontrast media in small clinical trials without any consistent clear cut evidence of benefit. None of these antioxidants acts via G-protein-coupled receptors and classical signal transduction pathways, and any of these antioxidants could easily be used in combination with PACAP-based therapeutics. Vasodilators and vasoconstrictor antagonists, including fenoldopam, SB 209670, atrial natriuretic peptide, theophylline, and aminophylline, have also been used as adjunctive cytoprotective agents with iodinated radiocontrast media in small clinical trials without any consistent clear cut evidence of benefit. The intravenous administration of isotonic fluids is the only generally accepted strategy to reduce the incidence of contrast-induced nephropathy. There are currently no drugs that are approved by the U.S. FDA specifically for use as cytoprotective adjunctive agents with iodinated radiocontrast media.

Pituitary adenylate cyclase-activating polypeptide (PACAP) was isolated from ovine (sheep) hypothalami based on its ability to stimulate adenylate cyclase activity in rat anterior pituitary cell cultures (Miyata et al., *Biochem Biophys Res Commun* 164:567-574, 1989). PACAP exists as two $\alpha$-amidated peptides with 38 (PACAP38; SEQ ID NO:1) or 27 (PACAP27; SEQ ID NO:2) amino acids. Both peptides have the same N-terminal 27 amino acids and are synthesized from the same prohormone. The sequence of PACAP38 is identical in all mammals and differs from the reptilian, avian and amphibian orthologs by only one amino acid (Vaudry et al., *Pharmacol Rev* 52:269-324, 2000; Valiante et al., *Brain Res* 1127:66-75, 2007; Vaudry et al., *Pharmacol Rev* 61:283-357, 2009). PACAP is a member of the secretin/vasoactive intestinal peptide (VIP)/growth hormone-releasing hormone (GHRH) family, and PACAP27 has 68% sequence identity with VIP (SEQ ID NO:3). PACAP is most abundant in the brain and testis, but there are significant levels in other organs, including the adrenals, thymus, spleen, lymph nodes, and duodenal mucosa (Vaudry et al., *Pharmacol Rev* 52:269-324, 2000; Vaudry et al., *Pharmacol Rev* 61:283-357, 2009). The amount of PACAP in the kidney is relatively low (Arimura et al., *Endocrinology* 129:2787-2789, 1991). PACAP is synthesized as a preprohormone and is processed mainly by prohormone convertase 1, prohormone convertase 2 and prohormone convertase 4 (Li et al., *Neuroendocrinology* 69:217-226, 1999; Li et al., *Endocrinology* 141:3723-3730, 2000). The half-life of [$^{125}$I]-PACAP38 in the bloodstream of rats following intravenous injection is 5-6 minutes (Banks et al., *J Pharmacol Exp Ther* 267:690-696, 1993). Members of the secretin/VIP/GHRH family are degraded in plasma mainly by aminodipeptidases, especially dipeptidyl peptidase IV (Zhu et al., *J Biol Chem* 278:22418-2223, 2003).

A PACAP-specific receptor, designated as the $PAC_1$ receptor, has been cloned from several vertebrate species (Arimura, *Jpn J Physiol* 48:301-331, 1998; Vaudry et al., *Pharmacol Rev* 52:269-324, 2000; Vaudry et al., *Pharmacol Rev* 61:283-357, 2009). It is a G-protein-coupled receptor with seven putative membrane-spanning domains and belongs to a family of glycoprotein receptors that are coupled to multiple signal transduction pathways (Segre & Goldring, *Trends Endocrinol Metab* 4:309-314, 1993). PACAP binds not only to the $PAC_1$ receptor with a high affinity, but it also binds to the VIP1 ($VPAC_1$) and VIP2 ($VPAC_2$) receptors with an affinity comparable to or greater than VIP. On the other hand, VIP binds to the $PAC_1$ receptor with an affinity 100-1,000 times less than PACAP (Arimura, *Jpn J Physiol* 48:301-331, 1998). At least 10 splice variants of the rat $PAC_1$ receptor have been cloned and each variant is coupled to distinct combinations of signal transduction pathways (Vaudry et al., *Pharmacol Rev* 52:269-324, 2000; Vaudry et al., *Pharmacol Rev* 61:283-357, 2009). The "second" messengers include adenylate cyclase, phospholipase C, mitogen-activated protein (MAP) kinases, and calcium. PACAP/VIP receptor can be coupled to Gαs and/or Gαi/o in different types of cells. PACAP/VIP receptors are expressed in many different types of normal cells, including the catecholamine-containing cells in the adrenal medulla and the sympathetic ganglia; microglia, astrocytes and some types of neurons in the central nervous system; and T- and B-lymphocytes, macrophages and dendritic cells in the immune system (Vaudry et al., *Pharmacol Rev* 52:269-324, 2000; Vaudry et al., *Pharmacol Rev* 61:283-357, 2009). PACAP is a potent stimulator of catecholamine secretion from the adrenal medulla (Watanabe et al., *Am J Physiol* 269:E903-E909, 1995), but a potent inhibitor of the secretion of tumor necrosis factor-α (TNF-α), interleukin (IL)-6 and IL-12 from activated macrophages (Ganea & Delgado, *Crit Rev Oral Biol Med* 13:229-237, 2002). More pertinent to the present invention, PACAP has been reported to increase blood flow in the kidney (Nilsson, *Eur J Pharmacol* 253:17-25, 1994).

Although PACAP was isolated during a screen for novel hypophysiotropic factors, it soon became apparent that it is a pleiotropic peptide (Arimura, *Jpn J Physiol* 48:301-331, 1998; Vaudry et al., *Pharmacol Rev* 52:269-324, 2000). The extraordinarily potent neuroprotective/neurotrophic properties of PACAP were investigated by several laboratories shortly after its isolation. The cytoprotective effects of PACAP and VIP have been studied much more extensively in the nervous system than in any other major organ of the body. For example, PACAP prevented the neuronal death induced by gp120, the envelope glycoprotein of the human immunodeficiency virus (HIV), in rat hippocampal neuron/glia co-cultures. The dose-response curve was bimodal, with peaks at $10^{-13}$ M and $10^{-10}$ M (Arimura et al., *Ann NY Acad Sci* 739:228-243, 1994). The critical findings in this study have been confirmed by Kong et al. (*Neuroscience* 91:493-500, 1999), who used lipopolysaccharide as the neurotoxin in primary murine cortical neuron/glia co-cultures. The neuroprotective effect at $10^{-12}$ M was correlated with a significant reduction in the accumulation of nitrite in the culture medium. The neuroprotective effect of "low" (femtomolar) doses of PACAP in neuron/glia co-cultures was abolished by PD98059, a MAP kinase inhibitor, but the neuroprotective effect of "high" (nanomolar) doses of PACAP was not affected by PD98059 (Li et al., *J Mol Neurosci* 27:91-106, 2005). However, the neuroprotective effect of nanomolar doses of PACAP was abolished by Rp-cAMP, a protein kinase A inhibitor.

The drawbacks of using peptides for neuroprotection in the brain include their poor transport across the blood-brain barrier and their short half-life in the circulation after systemic administration. However, PACAP38 is transported from the blood to the brain via a saturable mechanism (Banks et al., *J Pharmacol Exp Ther* 267:690-696, 1993). Delayed systemic administration of PACAP has been shown to be neuroprotective in common in vivo preclinical models for both heart attack (Uchida et al., *Brain Res* 736:280-286, 1996) and stroke (Reglodi et al., *Stroke* 31:1411-1417, 2000). PACAP has also been shown by other laboratories to be neuroprotective in common in vivo preclinical models for other neurological diseases, including spinal cord injury (Chen & Tzeng, *Neurosci Lett* 384:117-121, 2005), Alzheimer's disease (Rat et al., *FASEB J* 25:3208-3218, 2011) and Parkinson's disease (Reglödi et al., *Behav Brain Res* 151:303-312, 2004).

The neuroprotective effects of low concentrations of PACAP in the nervous system are indirect and are probably mediated by at least four distinct mechanisms. (1) PACAP is a potent anti-inflammatory peptide. It has been shown to inhibit the induction of inducible nitric oxide synthase (iNOS) in activated macrophages, to inhibit the production of the pro-inflammatory cytokines TNF-α, IL-6 and IL-12 in activated macrophages, and to stimulate the production of the anti-inflammatory cytokine IL-10 in activated macrophages (Ganea & Delgado, *Crit Rev Oral Biol Med* 13:229-237, 2002). PACAP is also an extraordinarily potent "deactivator" of activated microglial cells (Kong et al., *Neuroscience* 91:493-500, 1999; Delgado et al., *Glia* 39:148-161, 2002), which are the resident macrophage-like cells in the nervous system. (2) Femtomolar ($10^{-15}$ M) concentrations of PACAP increase the levels of the mRNA for activity-dependent neurotrophic factor in murine neuron/glia co-cultures (David et al., *Society for Neuroscience* [33rd Annual Meeting], New Orleans, La., #38.1 [Abstract], 2003). (3) Yang et al. (*J Pharmacol Exp Ther* 319:595-603, 2006) have shown that femtomolar concentrations of PACAP inhibit microglial NADPH oxidase activity and extracellular superoxide levels in mesencephalic neuron/glia co-cultures. (4) Figiel & Engele (*J Neurosci* 20:3596-3605, 2000) have reported that PACAP increased the expression of the glutamate transporters GLT-1 and GLAST and increased the activity of the glutamate metabolizing enzyme glutamine synthetase in astrocytes. These effects of PACAP would be expected to decrease glutamatergic neurotransmission.

The cytoprotective properties of PACAP and VIP have been studied far less extensively in the kidney than in the nervous system. PACAP has been shown to protect the kidney against injuries caused by ischemia/reperfusion (Riera et al., *Transplantation* 72:1217-1223, 2001; Szakaly et al., *J Mol Neurosci* 36:89-96, 2008; Li et al., *Am J Nephrol* 32:522-532, 2010), the commonly used aminoglycoside antibiotic gentamicin (Li et al., *Regul Pept* 145:24-32, 2008), light-chain immunoglobulin overload (Li et al., *Regul Pept* 145:24-32, 2008), and acute administration of cisplatin (Li et al., 2009, Li et al., *J Mol Neurosci* 43:58-66, 2011) and cyclosporine A (Khan et al., *J Invest Med* 59:793-802, 2011). Nephrotoxicity is usually the "dose-limiting" toxicity for gentamicin, cisplatin and cyclosporine A. The renoprotective effects of PACAP, like the neuroprotective effects of PACAP, are associated with suppression of innate immune responses (e.g., Li et al., *J Mol Neurosci* 43:58-66, 2011). PACAP has also been shown to inhibit the production of transforming growth factor (TGF)-β1 by macrophages (Sun et al., *J Neuroimmunol* 107:88-99, 2000).

PACAP-like peptides have been shown to inhibit the proliferation of most normal hematopoietic cells (e.g., Ottaway & Greenberg, *J Immunol* 132:417-423, 1984; Boudard & Bastide, *J Neurosci Res* 29:29-41, 1991; Tatsuno et al., *Endocrinology* 128:728-734, 1991; Trejter et al., *Histol Histopathol* 16:155-158, 2001).

Native PACAP has already been administered to healthy human volunteers by investigators in at least five different laboratories (Hammond et al., *J Endocrinol* 137:529-532, 1993; Chiodera et al., *Neuroendocrinology* 64:242-246, 1996; Filipsson et al., *J Clin Endocrinol Metab* 82:3093-3098, 1997; Doberer et al., *Eur J Clin Invest* 37:665-672, 2007; Murck et al., *Am J Physiol* 292:E853-E857, 2007) and to a patient with multiple myeloma under a U.S. FDA-approved single-patient protocol (Li et al., *Peptides* 28:1891-1895, 2007). The only untoward effect reported was a transient flushing.

The published literature indicates that PACAP-like peptides can protect neurons (neuroepithelial cells) against a very broad range of injuries, including ischemia/reperfusion injury. The published literature also indicates that PACAP-like peptides can protect renal epithelial cells against injury due to ischemia/reperfusion.

Whether PACAP-like peptides can protect renal epithelial cells against iodinated radiocontrast agents has not been previously investigated.

Citation or discussion of a reference herein shall not be construed as an admission that such reference is prior art to the present invention.

SUMMARY OF THE INVENTION

The inventors have found that native human PACAP38 and PACAP analogs are extremely effective in protecting organs of the body (e.g., the kidney) against injury caused by a contrast agent, such as an iodinated radiocontrast media or a gadolinium-based magnetic resonance agent.

Accordingly, the present invention relates to methods and compositions for the treatment, management, prevention, and/or reduction of injury to one or more organs of the body (e.g., nervous system, brain, heart, lung, kidney, liver, pancreas, gall bladder, gastrointestinal tract, adrenal gland, thymus, spleen, lymph nodes, breast, ovary, testes, and/or prostate; preferably the kidney) of a human or other mammal caused by, or as a result of, administration of one or more contrast agents (e.g., iodinated radiocontrast media or gadolinium-based magnetic resonance agents) to the human or other mammal. The method involves the administration of an effective amount of one or more PACAP-like compounds which includes native human PACAP38, native human PACAP27, VIP, their agonists, analogs, fragments, or derivatives, having activities at one or more PACAP/VIP receptors (e.g., a PACAP-like compound having at least 60% (more preferably 70%, 75%, 80%, or 85%, and most preferably 90%, 95%, 97%, 99%, or 100%) sequence identity to one or more of SEQ ID NOs: 1-76), for the inhibition of a pathology-causing cell phenotype in the organ(s) (e.g., the kidney) caused by, or resulting from, one or more of the contrast agents.

The PACAP-like compounds of this invention can be purified from normal cells or extracellular fluids, synthesized by the methods of recombinant molecular biology, or (in the most common embodiment) synthesized by the methods of peptide chemistry.

PACAP-like compounds are extremely effective in protecting and/or rescuing kidney epithelial cells in a concentration-dependent manner. Thus, the present invention also relates to a method of treatment of these cells at a concentration of about $10^{-13}$ M to $10^{-6}$ M of the PACAP-like compound. When these cells are in culture, the concentration of the PACAP-like compound is preferably between $10^{-13}$ M and $10^{-6}$ M in the culture medium. When these cells are in the organs of a subject, the concentration of the PACAP-like compound is preferably between about $10^{-13}$ M to $10^{-6}$ M in the interstitial space or blood. The inventors have discovered that within the generally effective concentration range of the composition of this invention, there is a peak effectiveness, below which the effectiveness of the composition falls off to a significant degree. A concentration of the PACAP composition of the present invention between about $10^{-13}$ M and about $10^{-6}$ M permits treatment of the subject with minimal risk of adverse side effects from the treatment. In a preferred embodiment, the concentration of the PACAP-like compound is about $10^{-9}$ M.

The present discovery makes possible the use of the compositions of this invention in low concentrations to provide substantial protection and rescue of cells and tissues in organs of the body (e.g., kidney epithelial cells). In a specific embodiment, the composition of the present invention protects these cells and tissues from injury or death. The injury or death of these cells or tissues may be due to treatment with one or more commonly used iodinated contrast agents, including (but not limited to), iobitridol, iodipamide, iodixanol, iohexol, iomeprol, iopamidol, iopentol, iopromide, iotrolan, ioversol, ioxilan, iothalamate, ioxithalamate, ioxaglate, metrizamide, acetrizoate, metrizoate, and diatrizoate.

The compositions of the present invention may be administered intravenously, intraperitoneally, subcutaneously, intramuscularly, or otherwise into the bloodstream in order to achieve the optimal concentration for the treatment, management or prevention of injury to an organ of the body (e.g., the kidney) of a human or other mammal caused by a contrast agent, such as an iodinated radiocontrast media or a gadolinium-based magnetic resonance agent. The intravenous administration of the compositions of the present invention may be as a bolus injection, as a constant infusion (e.g., over a period of 1 to 24 hours, more preferably over a period of 1 to 12 hours) or as a bolus injection followed immediately by a constant infusion. In a preferred embodiment, the subject is being treated with one or more contrast agents (e.g., one or more iodinated contrast agents) for a cardiac angiography and the PACAP-like compound is administered as a bolus injection (in order to saturate any serum binding proteins) followed immediately by a constant infusion. In a preferred embodiment, parenteral administration is used. In several embodiments, the PACAP-like compound is administered to a mammal in need thereof, (e.g., a human) at a dose in the range of 1 µg to 1 gram (e.g., 100 to 5000 µg, such as about 500 µg).

The compositions of the present invention may be administered into the renal artery in order to have preferential access to the kidney.

The compositions of the present invention may also be administered in a controlled-release or a sustained-release formulation. In a preferred embodiment, the subjects are treated with one or more nonionic iodinated radiocontrast media for cardiac angiography.

The compositions of the present invention may be administered after encapsulation in liposomes or microparticles. The compositions of the present invention may also be administered transcutaneously after encapsulation in dendrimers. In a preferred embodiment, the subjects are treated with one or more iodinated radiocontrast media for a diagnostic or interventional cardiovascular procedure.

The compositions of the present invention may be administered in combination with other cytoprotective agents that have different mechanisms of action, including (but not limited to) ascorbic acid, vitamin E, mesna, palifermin (human keratinocyte growth factor), erythropoietin, apocynin, diphenylene iodonium, pentoxifylline, etanercept, simvastatin, amifostine, dexrazoxane, and N-acetylcysteine in order to have an additive or a synergistic effect.

The compositions of the present invention may be administered in combination with vasodilators or vasoconstrictor antagonists, including (but not limited to) fenoldopam, SB 209670, atrial natriuretic peptide, theophylline, and aminophylline, in order to have an additive or a synergistic effect.

In an embodiment of the invention, injury to one or more organs of the body, e.g., the kidney, caused by a contrast agent, such as an iodinated radiocontrast media or a gadolinium-based magnetic resonance agent, can be assessed by determining the present of one or more of the following risk factors: pre-existing kidney disease(s), diabetes mellitus, hypertension, cardiovascular diseases, sickle cell anemia, gout flares, multiple myeloma, hypoalbuminemia, hypovolemia, and dehydration.

In another embodiment of the invention, injury to one or more organs of the body, e.g., the kidney, caused by a contrast agent, such as an iodinated radiocontrast media or a gadolinium-based magnetic resonance agent, can be assessed by determining the level of one or more biomarkers, either at the protein level or at the mRNA level. These biomarkers include one or more of the following creatinine, kidney injury molecule 1 (KIM-1), netrin-1, Nogo-B (reticulon 4B), NADPH oxidase (Nox)-4, Nox-2, tumor necrosis factor-alpha (TNF-α), transforming growth factor-beta (TGF-β), interferon-gamma (IFN-γ), and monocyte chemotactic protein-1 (MCP-1). For example, organ injury, such as kidney injury, may be assessed by determining the concentration of creatinine in serum or urine. Contrast-induced nephropathy is usually defined as an increase in serum creatinine of more than 25% or an increase of more than 0.5 mg/dl within three days after the intravascular administration of contrast media that cannot be explain by other known causes. In another embodiment, urinary levels of kidney injury molecule 1 (KIM-1) and/or netrin-1 may be assessed as a biomarkers of kidney injury instead of, or in combination with, a determination of serum or urinary levels of creatinine. In still another embodiment, the level of Nogo-B (reticulon 4B), which is up-regulated in the proximal tubules of the mouse kidney following unilateral ureteral obstruction and ischemia/reperfusion, and/or Nogo-B mRNA, may be assessed as an indicator of diverse forms of renal proximal tubule injury. Also, an increase in the level of Nox-4 and/or Nox-2 mRNA may be assessed as an indicator of organ injury, e.g., kidney injury.

Therapy, according to the present invention, may also be assessed by determining a decrease in the level of one or more of the following biomarkers, either at the protein level or at the mRNA level: creatinine, kidney injury molecule 1 (KIM-1), netrin-1, Nogo-B (reticulon 4B), Nox-4, Nox-2, tumor necrosis factor-alpha (TNF-α), transforming growth factor-beta (TGF-β), interferon-gamma (IFN-γ), and monocyte chemotactic protein-1 (MCP-1). The decrease in biomarker expression may be determined by assessing the level of the biomarker in a sample, such as a bodily fluid (e.g., blood (e.g., serum), urine, saliva, and/or lymph) or tissue (e.g., one or more cells) of the mammal. The decrease in the expression level of the biomarker in the sample (e.g., the biomarker protein and/or mRNA) may be at least 5% (e.g., 10%, 15%, 20%, 30%, 35%, 40%, 45%, or 50% or more), relative to a control sample from a similarly situated mammal that is not treated according to the method(s) of the present invention.

Therapy, according to the present invention, may also be assessed by determining a decrease in cell death in a mammal following administration of one or more PACAP-like compounds (alone or in combination with one or more cytoprotective agents). The decrease in cell death may be, e.g., at least 5% (e.g., 10%, 15%, 20%, 30%, 35%, 40%, 45%, 50%, 55%, 60%, 65%, 70%, 75%, 80%, or 85%, or more), relative to a similarly situated control mammal that is not treated according to the method(s) of the present invention.

BRIEF DESCRIPTION OF THE DRAWINGS

FIG. 1 shows the primary amino acid sequences of PACAP38 (SEQ ID NO:1), PACAP27 (SEQ ID NO:2), VIP (SEQ ID NO:3), [D-Ser$^2$]PACAP38 (SEQ ID NO:4), [Aib$^2$]PACAP38 (SEQ ID NO:5), [D-Ser$^2$,Lys$^{38}$-palmitoyl]PACAP38 (SEQ ID NO:6), [Ala$^{22}$]PACAP38 (SEQ ID NO:8), [Lys$^{34}$]PACAP38 (SEQ ID NO:10), N-acetyl[Pip$^3$]PACAP38 (SEQ ID NO:38), [Pip$^3$,Ala$^{14,17}$,Aib$^{16,28}$,Lys$^{34}$, D-Lys$^{38}$]PACAP38 (SEQ ID NO:39), and [Pip$^3$,Ala$^{15,17}$, Aib$^{16,28}$,Lys$^{34}$,D-Lys$^{38}$]PACAP38 (SEQ ID NO:40). All of these compounds have been used in the experiments described in one or more of the figures listed below.

SEQUENCES

Figure 2:
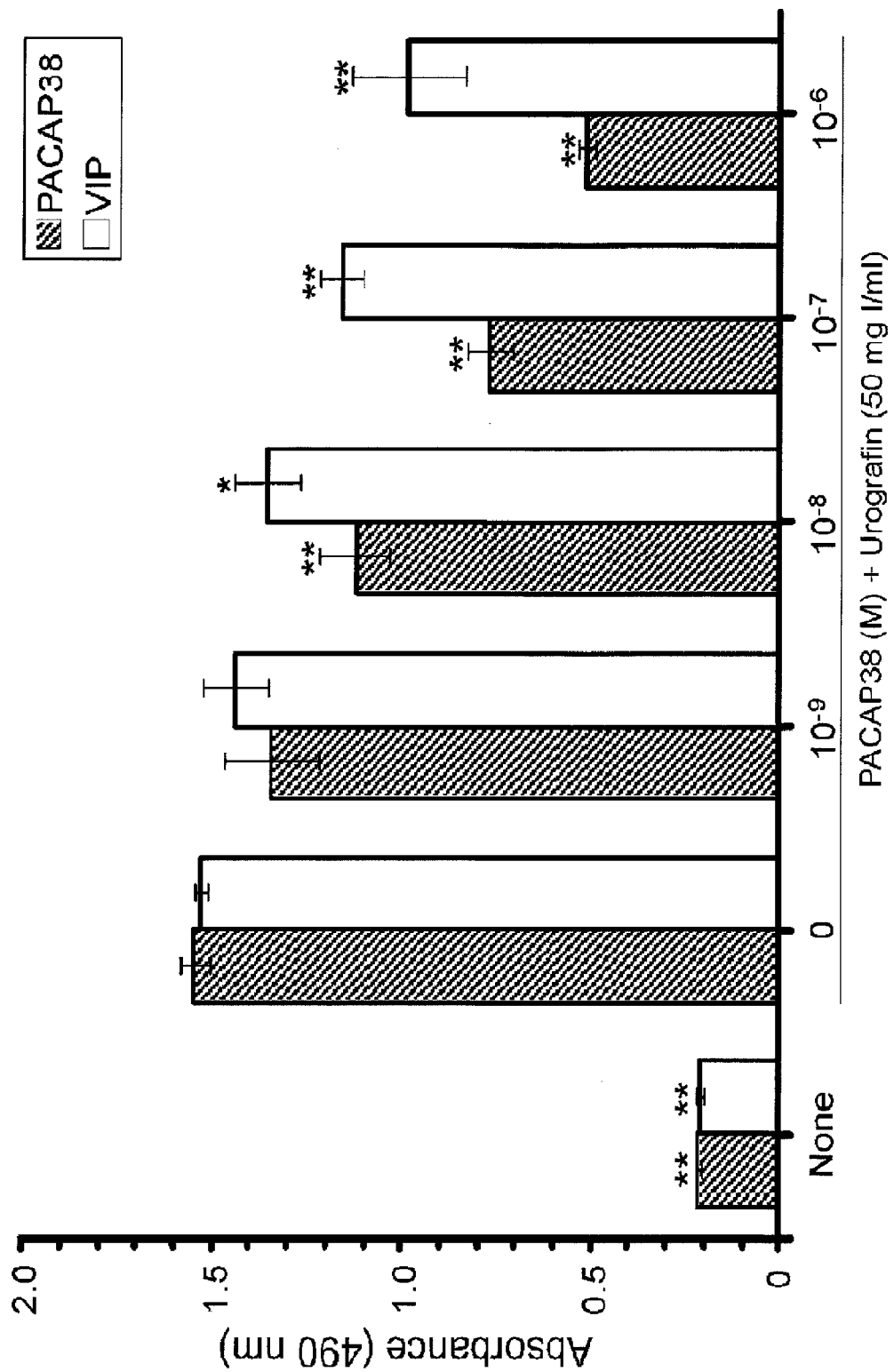
FIG. 2 shows the reduction by PACAP38 or VIP of the injury (cytotoxicity) to human renal proximal tubule epithelial cells caused by treatment with Urografin. The HK-2 human kidney cells were cultured in Keratinocyte-Serum Free Medium supplemented with recombinant epidermal growth factor and bovine pituitary extract. The effects of various concentrations of PACAP38 or VIP on cell injury were assessed by determining the activity of the cytoplasmic enzyme lactate dehydrogenase in the culture medium. Each value represents the mean plus/minus the standard error of four determinations. **p<0.01 and *p<0.05 compared to the cells treated only with Urografin. PACAP38 was significantly more potent than VIP at $10^{-8}$ M (p<0.05), $10^{-7}$ M (p<0.01) and $10^{-6}$ M (p<0.01).

SEQ ID NOs:1-3 are human sequences. SEQ ID NOs:4-70 are modifications of the corresponding human sequences. Below is a brief summary of the sequences presented in the accompanying sequence listing, which is incorporated by reference herein in its entirety:

SEQ ID NO:1 is the amino-acid sequence of PACAP38, which can be used according to the present invention.

SEQ ID NO:2 is the amino-acid sequence of PACAP27, which can be used according to the present invention.

SEQ ID NO:3 is the amino-acid sequence of VIP, which can be used according to the present invention.

SEQ ID NO:4 is the amino-acid sequence of [D-Ser$^2$]PACAP38, which can be used according to the present invention.

SEQ ID NO:5 is the amino-acid sequence of [Aib$^2$]PACAP38, which can be used according to the present invention.

SEQ ID NO:6 is the amino-acid sequence of [D-Ser$^2$, Lys$^{38}$-palmitoyl]PACAP38, which can be used according to the present invention.

SEQ ID NO:7 is the amino-acid sequence of [Aib$^2$,Lys$^{38}$-palmitoyl]PACAP38, which can be used according to the present invention.

SEQ ID NO:8 is the amino-acid sequence of [Ala$^{22}$]PACAP38, which can be used according to the present invention.

SEQ ID NO:9 is the amino-acid sequence of [Ala$^{16}$,Ala$^{17}$,D-Lys$^{38}$]PACAP38, which can be used according to the present invention.

SEQ ID NO:10 is the amino-acid sequence of [Lys$^{34}$]PACAP38, which can be used according to the present invention.

SEQ ID NO:11 is the amino-acid sequence of [Lys$^{38}$-palmitoyl]PACAP38, which can be used according to the present invention.

SEQ ID NO:12 is the amino-acid sequence of [D-Ser$^2$, Ala$^{16}$,Ala$^{17}$,D-Lys$^{38}$]PACAP38, which can be used according to the present invention.

SEQ ID NO:13 is the amino-acid sequence of [Aib$^2$,Ala$^{16}$, Ala$^{17}$,D-Lys$^{38}$]PACAP38, which can be used according to the present invention.

SEQ ID NO:14 is the amino-acid sequence of [D-Ala$^2$]PACAP38, which can be used according to the present invention.

SEQ ID NO:15 is the amino-acid sequence of [D-Ser$^2$, Nle$^{17}$]PACAP38, which can be used according to the present invention.

SEQ ID NO:16 is the amino-acid sequence of [Aib$^2$,Nle$^{17}$]PACAP38, which can be used according to the present invention.

SEQ ID NO:17 is the amino-acid sequence of [D-Ala$^2$, Nle$^{17}$]PACAP38, which can be used according to the present invention.

SEQ ID NO:18 is the amino-acid sequence of [D-Ser$^2$, Ala$^{17}$]PACAP38, which can be used according to the present invention.

SEQ ID NO:19 is the amino-acid sequence of [Aib$^2$,Ala$^{17}$]PACAP38, which can be used according to the present invention.

SEQ ID NO:20 is the amino-acid sequence of [D-Ala$^2$, Ala$^{17}$]PACAP38, which can be used according to the present invention.

SEQ ID NO:21 is the amino-acid sequence of [Lys$^{36}$-palmitoyl]PACAP38, which can be used according to the present invention.

SEQ ID NO:22 is the amino-acid sequence of [Lys$^{32}$-palmitoyl]PACAP38, which can be used according to the present invention.

SEQ ID NO:23 is the amino-acid sequence of [Lys$^{29}$-palmitoyl]PACAP38, which can be used according to the present invention.

SEQ ID NO:24 is the amino-acid sequence of [D-Ser$^2$, Lys$^{36}$-palmitoyl]PACAP38, which can be used according to the present invention.

SEQ ID NO:25 is the amino-acid sequence of [D-Ser$^2$, Lys$^{32}$-palmitoyl]PACAP38, which can be used according to the present invention.

SEQ ID NO:26 is the amino-acid sequence of [D-Ser$^2$, Lys$^{29}$-palmitoyl]PACAP38, which can be used according to the present invention.

SEQ ID NO:27 is the amino-acid sequence of [Aib$^2$,Lys$^{36}$-palmitoyl]PACAP38, which can be used according to the present invention.

SEQ ID NO:28 is the amino-acid sequence of [Aib$^2$,Lys$^{32}$-palmitoyl]PACAP38, which can be used according to the present invention.

SEQ ID NO:29 is the amino-acid sequence of [Aib$^2$,Lys$^{29}$-palmitoyl]PACAP38, which can be used according to the present invention.

SEQ ID NO:30 is the amino-acid sequence of [Ala$^{14}$]PACAP38, which can be used according to the present invention.

SEQ ID NO:31 is the amino-acid sequence of [Ala$^{20}$]PACAP38, which can be used according to the present invention.

SEQ ID NO:32 is the amino-acid sequence of [Ala$^{21}$]PACAP38, which can be used according to the present invention.

SEQ ID NO:33 is the amino-acid sequence of [D-Ser$^2$, Ala$^{14}$]PACAP38, which can be used according to the present invention.

SEQ ID NO:34 is the amino-acid sequence of [D-Ser$^2$, Ala$^{20}$]PACAP38, which can be used according to the present invention.

SEQ ID NO:35 is the amino-acid sequence of [D-Ser$^2$, Ala$^{21}$]PACAP38, which can be used according to the present invention.

SEQ ID NO:36 is the amino-acid sequence of [Ala$^{14}$, Ala$^{20}$]PACAP38, which can be used according to the present invention.

SEQ ID NO:37 is the amino-acid sequence of [Pip$^3$]PACAP38, which can be used according to the present invention.

SEQ ID NO:38 is the amino-acid sequence of N-acetyl [Pip$^3$]PACAP38, which can be used according to the present invention.

SEQ ID NO:39 is the amino-acid sequence of [Pip$^3$, Ala$^{14,17}$,Aib$^{16,28}$,Lys$^{34}$,D-Lys$^{38}$]PACAP38, which can be used according to the present invention.

SEQ ID NO:40 is the amino-acid sequence of [Pip$^3$, Ala$^{15,17}$,Aib$^{16,28}$,Lys$^{34}$,D-Lys$^{38}$]PACAP38, which can be used according to the present invention.

SEQ ID NO:41 is the amino-acid sequence of [D-Ser$^2$] PACAP27, which can be used according to the present invention.

SEQ ID NO:42 is the amino-acid sequence of [Aib$^2$] PACAP27, which can be used according to the present invention.

SEQ ID NO:43 is the amino-acid sequence of [Ala$^2$] PACAP27, which can be used according to the present invention.

SEQ ID NO:44 is the amino-acid sequence of [D-Ala$^2$] PACAP27, which can be used according to the present invention.

SEQ ID NO:45 is the amino-acid sequence of [D-Ser$^2$, Nle$^{17}$]PACAP27, which can be used according to the present invention.

SEQ ID NO:46 is the amino-acid sequence of [Aib$^2$,Nle$^{17}$] PACAP27, which can be used according to the present invention.

SEQ ID NO:47 is the amino-acid sequence of [D-Ala$^2$, Nle$^{17}$]PACAP27, which can be used according to the present invention.

SEQ ID NO:48 is the amino-acid sequence of [D-Ser$^2$, Ala$^{17}$]PACAP27, which can be used according to the present invention.

SEQ ID NO:49 is the amino-acid sequence of [Aib$^2$,Ala$^{17}$] PACAP27, which can be used according to the present invention.

SEQ ID NO:50 is the amino-acid sequence of [D-Ala$^2$, Ala$^{17}$]PACAP27, which can be used according to the present invention.

SEQ ID NO:51 is the amino-acid sequence of [D-Ser$^2$,D-Leu$^{27}$]PACAP27, which can be used according to the present invention.

SEQ ID NO:52 is the amino-acid sequence of [Aib$^2$,D-Leu$^{27}$]PACAP27, which can be used according to the present invention.

SEQ ID NO:53 is the amino-acid sequence of [Ala$^{22}$,D-Leu$^{27}$]PACAP27, which can be used according to the present invention.

SEQ ID NO:54 is the amino-acid sequence of [D-Ala$^2$,D-Leu$^{27}$]PACAP27, which can be used according to the present invention.

SEQ ID NO:55 is the amino-acid sequence of [D-Ser$^2$, Nle$^{17}$,D-Leu$^{27}$]PACAP27, which can be used according to the present invention.

SEQ ID NO:56 is the amino-acid sequence of [Aib$^2$,Nle$^{17}$, D-Leu$^{27}$]PACAP27, which can be used according to the present invention.

SEQ ID NO:57 is the amino-acid sequence of [D-Ala$^2$, Nle$^{17}$,D-Leu$^{27}$]PACAP27, which can be used according to the present invention.

SEQ ID NO:58 is the amino-acid sequence of [D-Ser$^2$, Ala$^{17}$,D-Leu$^{27}$]PACAP27, which can be used according to the present invention.

SEQ ID NO:59 is the amino-acid sequence of [Aib$^2$,Ala$^{17}$, D-Leu$^{27}$]PACAP27, which can be used according to the present invention.

SEQ ID NO:60 is the amino-acid sequence of [D-Ala$^2$, Ala$^{17}$,D-Leu$^{27}$]PACAP27, which can be used according to the present invention.

SEQ ID NO:61 is the amino-acid sequence of [D-Ser$^2$]VIP, which can be used according to the present invention.

SEQ ID NO:62 is the amino-acid sequence of [Aib$^2$]VIP, which can be used according to the present invention.

SEQ ID NO:63 is the amino-acid sequence of [Ala$^{22}$]VIP, which can be used according to the present invention.

SEQ ID NO:64 is the amino-acid sequence of [D-Ala$^2$] VIP, which can be used according to the present invention.

SEQ ID NO:65 is the amino-acid sequence of [D-Ser$^2$, Nle$^{17}$]VIP, which can be used according to the present invention.

SEQ ID NO:66 is the amino-acid sequence of [Aib$^2$,Nle$^{17}$] VIP, which can be used according to the present invention.

SEQ ID NO:67 is the amino-acid sequence of [D-Ala$^2$, Nle$^{17}$]VIP, which can be used according to the present invention.

SEQ ID NO:68 is the amino-acid sequence of [D-Ser$^2$, Ala$^{17}$]VIP, which can be used according to the present invention.

SEQ ID NO:69 is the amino-acid sequence of [Aib$^2$,Ala$^{17}$] VIP, which can be used according to the present invention.

SEQ ID NO:70 is the amino-acid sequence of [D-Ala$^2$, Ala$^{17}$]VIP, which can be used according to the present invention.

SEQ ID NO:71 is the amino-acid sequence of lizard (*Podarcis sicula*) PACAP38, which can be used according to the present invention.

SEQ ID NO:72 is the amino-acid sequence of chicken (*Galus domesticus*) PACAP38, which can be used according to the present invention.

SEQ ID NO:73 is the amino-acid sequence of frog (*Rana ridibunda* and *Xenopus laevis*) PACAP38, which can be used according to the present invention.

SEQ ID NO:74 is the amino-acid sequence of salmon (*Oncorhynchus nerka*) PACAP38, which can be used according to the present invention.

SEQ ID NO:75 is the amino-acid sequence of channel catfish (*Ictalurus punctatus*) PACAP38, which can be used according to the present invention.

SEQ ID NO:76 is the amino-acid sequence of one naturally occurring variant of sand fly (*Lutzomyia longipalpis*) maxadilan, which can be used according to the present invention.

DEFINITIONS

The following standard three-letter abbreviations are used herein to identify amino acid residues.
Aib, α-aminoisobutyric acid
Ala, alanine
Arg, arginine
Asn, asparagine
Asp, aspartic acid
Cys, cysteine
Gln, glutamine
Glu, glutamic acid
Gly, glycine
His, histidine
Ile, isoleucine
Leu, leucine
Lys, lysine
Met, methionine
Nle, norleucine
Phe, phenylalanine
Pip, pipecolic acid (piperidine-2-carboxylic acid)
Pro, proline
Ser, serine
Thr, threonine Trp, tryptophan
Tyr, tyrosine
Val, valine As used herein, the term "about" refers to a value that is ±10% of the recited value.

By "administration" or "administering" is meant a method of providing a dosage of an agent or composition of the invention to a mammal (e.g., a human), where the route is, e.g., topical, oral, parenteral (e.g., intravenous, intraperitoneal, intraarterial, intradermal, intramuscular, or subcutaneous injection, inhalation, optical drops, or implant), nasal, vaginal, rectal, or sublingual application in admixture with a pharmaceutically acceptable carrier adapted for such use. The preferred method of administration can vary depending on various factors, e.g., the components of the pharmaceutical composition, site of the potential or actual injury (e.g., the location of injured organ), and the severity of injury.

As used herein, the term "analog" refers to both conformational and linear sequence analogs. Maxadilan, a 61-amino-acid peptide with two disulfide bridges that is synthesized naturally in the salivary glands of the hematophagous sand fly *Lutzomyia longipalpis*, is one example of a conformational analog of PACAP. It has no obvious linear amino-acid sequence identities with PACAP but binds preferentially to the $PAC_1$ receptors with high affinity (Tatsuno et al., *Brain Res* 889:138-148, 2001; Lerner et al., *Peptides* 28:1651-1654, 2007). The amino-acid sequences of maxadilan made by sand flies from different regions of Central and South America can differ by more than 20%. However, the relative positions of the cysteine residues in these bioactive orthologs are invariant and all of these bioactive orthologs have a similar predicted secondary structure. The amino-acid sequences of some naturally occurring maxadilans are described by Lanzaro et al. (*Insect Mol Biol* 8:267-275, 1999). The amino-acid sequence of one naturally occurring maxadilan is shown as SEQ ID NO:76. Therefore, linear analogs of conformational analogs of PACAP, such as linear analogs of maxadilan (Reddy et al., *J Biol Chem* 281:16197-16201, 2006), would be expected to bind to and stimulate PACAP/VIP receptors. Those skilled in the art will recognize that additional conformational analogs of PACAP could be created by synthetic combinatorial chemistry or phage display technologies. A peptide analog may contain one or more amino acids that occur naturally in mammalian cells but do not occur naturally in mammalian peptides. For example (but not by way of limitation), a peptide analog may contain γ-amino-N-butyric acid (GABA), β-alanine, ornithine, and citrulline. An analog of a peptide may also contain one or more nonnatural amino acids that do not occur naturally in mammalian cells. For example (but not by way of limitation), an analog of a peptide may also contain D-alanine, naphthylalanine, pyridylalanine, and norleucine. An analog may have an extension of one or more naturally occurring and/or nonnatural amino acids at its amino terminus and/or its carboxyl terminus. The extension at the amino terminus and/or the carboxyl terminus may include one or more additional copies of the same peptide and/or other bioactive peptides. The extension at the amino terminus and/or the carboxyl terminus may include one or more sites for proteolytic processing in order to make the extended peptide function as a precursor (prodrug) for the bioactive peptide. For example, the PACAP-like compounds may include cleavage sites at the amino terminus and/or the carboxyl terminus for one or more of the following proteolytic enzymes: trypsin, chymotrypsin, a prohormone convertase (e.g., prohormone convertase 1, 2, 4, or 7), furin, chymase, thrombin, calpain, a cathepsin (e.g., cathepsin A, B, D, G, H, or L), papain, Factor Xa, Factor IXa, Factor XIa, renin, chymosin (rennin), thermolysin, a kallikrein, an elastase, and a matrix metalloproteinase.

As used herein, the term "derivative" refers to a peptide that has been modified by the covalent attachment of another molecule and/or a functional group to the peptide chain. For example (but not by way of limitation), a derivative of a peptide may be produced by glycosylation, acetylation, pegylation, acylation, alkylation, oxidation, phosphorylation, sulfation, formylation, methylation, demethylation, amidation, gamma-carboxylation, cyclization, lactamization, prenylation, myristoylation, iodination, selenoylation, ribosylation, ubiquitination, or hydroxylation. The derivatized peptide can be a peptide analog. A derivative of a peptide can easily be made by standard techniques known to those of skilled in the art. A derivative of a peptide may possess an identical function(s) to the parent peptide. A derivative of a peptide may also have one or more other functions in addition to the function(s) of the parent peptide. For example (but not by way of limitation), a derivative of a peptide may have a longer half-life than the parent peptide and/or have cytoprotective or cytotoxic properties that are not possessed by the parent peptide.

As used herein, the term "fragment" in the context of PACAP-like or VIP-like peptides refers to a peptide that has fewer amino acids than the full-length PACAP-like or VIP-like peptide and has at least five contiguous amino acids (e.g., at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 contiguous amino acids) with sequence similarity (e.g., at least 60%, 65%, 70%, 75%, 80%, 85%, 90%, 95%, 97%, 99%, or 100% sequence similarity/identity) to the PACAP-like or VIP-like peptide, respectively.

As used herein, the adjective "hematopoietic" refers to cells (including cancer cells) that are derived from hematopoietic stem cells. The normal cells of the body that are derived from hematopoietic stem cells include (but are not limited to) erythrocytes, granulocytes (basophils, eosinophils and neutrophils), lymphocytes, monocytes (macrophages, microglia, splenocytes, and dendritic cells), and thrombocytes.

As used herein, the term "in combination with" refers to the use of more than one therapeutic or cytoprotective agent (e.g., in addition to the use of a PACAP-like compound). The use of the term "in combination with" does not restrict the order in which the therapeutic or cytoprotective agent is administered to a subject or mammal. One therapeutic or cytoprotective agent can be administered prior to, concomitantly with, or subsequent to the administration of the other therapeutic or cytoprotective agent. The therapies are administered to a subject or mammal in a sequence and within a time interval such that the PACAP-like compound(s) of the present invention can act together with the other agent to provide a different response from the subject or mammal, preferably a greater therapeutic or cytoprotective benefit, than if they were administered otherwise.

As used herein, the term "nervous system" refers to the central nervous system (the brain and spinal cord), the sympathetic nervous system, the parasympathetic nervous system, and the enteric nervous system.

As used herein, the term "PACAP" refers to human PACAP27 (SEQ ID NO:2) and/or human PACAP38 (SEQ ID NO:1).

As used herein, the term "PACAP/VIP receptor agonist" refers to any molecule, including a protein, naturally post-translationally or synthetically modified protein, polypeptide, naturally or synthetically modified polypeptide, peptide, naturally or synthetically modified peptide, and large or small nonpeptide molecules, that binds to and stimulates one or more of the PACAP/VIP receptors. As used herein, the term "PACAP-like compound" refers to human PACAP27 (SEQ ID NO:2), human PACAP38 (SEQ ID NO:1), human VIP (SEQ ID NO:3), sand fly maxadilan (SEQ ID NO:70), and peptides or peptidomimetics compounds that are orthologs, paralogs, analogs, fragments, or derivatives of these naturally occurring peptides and that have agonist activity at one or more PACAP/VIP receptors.

As used herein, the term "peptidomimetic" refers to both hybrid peptide/organic molecules and nonpeptide organic molecules that have critical functional groups in a three-dimensional orientation that is functionally equivalent to the corresponding peptide (Marshall, *Tetrahedron* 49:3547-3558, 1993). Peptidomimetic compounds that are functionally equivalents to the PACAP-like compounds of the present invention can be rationally designed by those skilled in the art based on published structure-activity studies (e.g., Igarashi et al., *J Pharmacol Exp Ther* 301:37-50, 2002; Igarashi et al., *J Pharmacol Exp Ther* 303:445-460, 2002; Bourgault et al., *Peptides* 29:919-932, 2008; Bourgault et al., *J Med Chem* 52:3308-3316, 2009).

The terms "percent identity" and "percent similarity" can be used to compare the amino-acid sequences of two peptides. To determine the percent identity of two amino acid sequences, the sequences are aligned for optimal comparison purposes (e.g., gaps can be introduced in the sequence of a first amino-acid sequence for optimal alignment with a second amino-acid sequence). The amino-acid residues at the corresponding amino-acid positions are then compared. When a position in the first sequence is occupied by the same amino-acid residue at the corresponding position in the second sequence, then the molecules are identical at that position. The percent identity between the two sequences is a function of the number of identical positions shared by the sequences (i.e., % identity=the number of identical overlapping positions/total number of positions×100%). In the most common embodiment, the two amino-acid sequences are the same length. To determine the percent similarity of two amino acid sequences, the sequences are also aligned for optimal comparison purposes. When a position in the first sequence is occupied by either the same amino-acid residue or a "conserved" amino acid at the corresponding position in the second sequence, then the molecules are similar at that position. The percent similarity between the two sequences is a function of the number of corresponding positions in the amino acid sequences at which the amino acids are either identical or the different amino acids are conserved substituents (i.e., % similarity=the number of identical or conserved overlapping positions/total number of positions×100%). A conservative substitution is a substitution of one amino acid by another amino acid with a similar side-chain. A conservative substitution frequently results in an analog with similar physical and biological properties. The following is a list of commonly defined classes of "similar" amino acids that occur naturally in mammalian peptides.

Aromatic side-chain: phenylalanine≈tyrosine≈tryptophan≈histidine

Acidic side-chain: aspartic acid≈glutamic acid

Basic side-chain: arginine≈lysine≈histidine

β-Branched side-chain: threonine≈valine≈isoleucine

Nonpolar side-chain: alanine≈valine≈leucine≈proline≈methionine≈phenylalanine≈tryptophan Uncharged polar side-chain: glycine≈asparagine≈glutamine≈serine≈threonine≈cysteine≈tyrosine Those skilled in the art will recognize that many amino acids that occur naturally in mammalian cells but do not occur naturally in mammalian peptides and many nonnatural amino acids that do not occur naturally in mammalian cells can be substituted conservatively for one or more of the amino acids that occur naturally in mammalian peptides. For example (but not by way of limitation), hydroxyproline, dehydroproline and pipecolic acid could be substituted conservatively for proline, sarcosine, dialkylglycine and α-aminocycloalkane carboxylic acid could be substituted conservatively for glycine, and α-aminoisobutyric acid, naphthylalanine and pyridylalanine could be substituted conservatively for alanine. "Percent identity" and "percent similarity" are determined after optimal alignment of the two sequences without or without the introduction of one or more gaps in one or both amino-acid sequences. There are many algorithms that are well known to those skilled in the art that can be used to determine the optimal alignment. In the most common embodiment, the two amino-acid sequences are the same length.

As used herein, the term "subject" or "mammal" refers to either a non-primate (e.g., a cow, pig, horse, cat, dog, rat, etc.) or a primate (e.g., a monkey or a human being), most preferably a human being. In a specific embodiment, the subject or mammal is a farm animal (e.g., a horse, pig, lamb or cow) or a pet (e.g., a dog, cat, rabbit, or monkey). In another embodiment, the subject or mammal is an animal other than a farm animal or a pet (e.g., a mouse, rat or guinea pig). In a preferred embodiment, the subject or mammal is a normal human being (e.g., a human having no known diseases or disorders (e.g., no known diseases or disorders other than those associated with normal development and/or aging)). In another preferred embodiment, the subject or mammal is a human that has an untreated or treated cancer (e.g., myeloma, such as multiple myeloma).

By "treating," "managing," "reducing," "inhibiting," or "preventing" an injury to an organ of the body of a mammal, such as a human (e.g., the nervous system, the brain, the heart, the lung, the kidney, the liver, the kidneys, the pancreas, the gall bladder, the gastrointestinal tract (e.g., the pharynx, esophagus, stomach, small intestine (e.g., the duodenal mucosa), large intestine, appendix, and colon), the breast, the ovary, the testes, the prostate, the adrenal gland, the thymus, the spleen, or the lymph nodes) that results as an effect of treatment of the mammal with an iodinated radiocontrast media is meant administering a PACAP-like compound of the invention to the mammal to ameliorate, alleviate, or hinder injury to one or more organs of the body of a mammal associated with, that results from, or that is likely to result from, administration of the iodinated radiocontrast media. By way of example only, administration of a PACAP-like compound provides treatment to a mammal by allowing an increase in the amount of the iodinated radiocontrast media that can be administered to a mammal of at least about 1%, 2%, 5%, 8%, 10%, 15%, or 20% or more above the maximum tolerable dose normally administered to the mammal without an increase in, or with a diminishment of, organ injury (e.g., thereby providing a reduction or inhibition, or the prevention of, injury to an organ of the mammal). Desirably, at least 20, 40, 60, 80, 90, or 95% of the treated mammals exhibit no or a substantially reduced injury to an organ of the body and/or greater tolerance to the iodinated radiocontrast media.

DETAILED DESCRIPTION OF THE INVENTION

The inventors of the present patent application have discovered that damage to cultured human renal tubule epithelial cells caused by iodinated radiocontrast media can be dramatically reduced by native human PACAP38 and analogs, fragments and derivatives of PACAP38. The inventors of the present patent application have also discovered that the nephrotoxicity caused by iodinated radiocontrast media in mice in vivo can be dramatically reduced by native human PACAP38 and analogs, fragments and derivatives of PACAP38. The inventors of the present patent application have further discovered that the nephrotoxicity caused by both ionic and nonionic iodinated radiocontrast media can be dramatically reduced by native human PACAP38 and analogs, fragments and derivatives of PACAP38. Furthermore, the severity of the anaphylactic reaction caused by iodinated radiocontrast media in some subjects and the severity of the nephrogenic systemic fibrosis caused by gadolinium-based contrast agents in some subjects can also be reduced by native human PACAP38 and analogs, fragments and derivatives of PACAP38. The present inventors have also discovered that the severity of an injury to one or more organs of the body of a subject (e.g., kidney injury) caused by iodinated radiocontrast media can be reliably monitored noninvasively by determining the levels of one or more of the following biomarkers in a sample from a subject, either at the protein level or at the mRNA level: creatinine, kidney injury molecule 1 (KIM-1), netrin-1, Nogo-B (reticulon 4B), Nox-4, Nox-2, tumor necrosis factor-alpha (TNF-α), transforming growth factor-beta (TGF-β), interferon-gamma (IFN-γ), and monocyte chemotactic protein-1 (MCP-1). In particular, kidney injury may be reliably monitored by determining, e.g., KIM-1 levels in urine.

In addition, the inventors have discovered that the homozygous eNOS-deficient mouse can be used to produce a simple and reproducible model of contrast-induced nephropathy.

Identification of PACAP-Like Compounds

The present invention provides methods for assaying and screening for PACAP-like compounds, such as PACAP38, PACAP27, VIP, their agonists, analogs, fragments, or derivatives, suitable for use in the method of the present invention by incubating the compounds with epithelial cells containing one or more PACAP/VIP receptors, e.g., kidney epithelial cells and hematopoietic cells, and then assaying for a reduction in a pathology-causing cell phenotype or an inhibition of cell proliferation (see, e.g., Li et al., Regul Pept 145:24-32, 2008). For example, a PACAP-like compound that would be useful for the method of the present invention should increase the viability of iodinated radiocontrast agent-treated kidney epithelial cells and decrease the rate of proliferation of hematopoietic cells. Alternatively, one may assay and screen for PACAP-like compounds, such as PACAP38, PACAP27, VIP, their agonists, analogs, fragments, or derivatives, suitable for use in the method of the present invention by assaying for a decrease in the level of one or more of the following biomarkers, either at the protein level or at the mRNA level: creatinine, kidney injury molecule 1 (KIM-1), netrin-1, Nogo-B (reticulon 4B), Nox-4, Nox-2, tumor necrosis factor-alpha (TNF-α), transforming growth factor-beta (TGF-β), interferon-gamma (IFN-γ), and monocyte chemotactic protein-1 (MCP-1). In addition, the intrinsic activity of any PACAP-like compound at each of the three PACAP/VIP receptors can be determined in stably transfected cell lines that express only one of these receptors by measuring the intracellular accumulation of cyclic AMP (Tatsuno et al., Brain Res 889:138-148, 2001). Radioligand receptor binding assays can be used to determine the affinity of a compound for each of the PACAP/VIP receptors. However, radioligand receptor binding assays do not differentiate between receptor agonists and receptor antagonists. Therefore, other types of assays well known to those skilled in the art must be used to discriminate between PACAP/VIP receptor agonists and PACAP/VIP receptor antagonists.

The viability of renal epithelial cells can be determined by a variety of techniques well known to those skilled in the art, including (but not limited to) quantification of the fragmentation of nuclear DNA or of caspase 3 activity, counting of apoptotic (pyknotic) cells, counting of Trypan blue-positive cells, and quantification of extracellular or intracellular lactate dehydrogenase activity. In the preferred embodiment, the fragmentation of nuclear DNA or caspase 3 activity is determined.

The proliferation of cells can be determined by a variety of techniques well known to those skilled in the art, including (but not limited to) quantification of the incorporation of bromodeoxyuridine or [$^3$H]thymidine into nuclear DNA, counting of the number of cells expressing proliferating cell nuclear antigen and counting of mitotic figures. In a preferred embodiment, the incorporation of bromodeoxyuridine or [$^3$H]thymidine into nuclear DNA is determined.

The intracellular accumulation of cyclic AMP in stably transfected cell lines that express only one of these receptors can be determined following stimulation with PACAP-like compounds by a variety of techniques well known to those skilled in the art, including (but not limited to) a radioimmunoassay or an enzyme-linked immunosorbent assay. The stimulation is stopped by the addition of ice-cold 20% trifluoroacetic acid. The cAMP is extracted from the cells, the extracts are centrifuged, the supernatants are placed into small plastic vials, and the supernatants are lyophilized for assay of the levels of cAMP. In the preferred embodiment, the intracellular levels of cAMP are quantified with an enzyme-linked immunosorbent assay.

Patient Population

Those skilled in the art will recognize, or be able to ascertain using standard medical references such as Harrison's Principles of Internal Medicine (18th Edition, 2011), Cecil Medicine (24th Edition, 2010) and/or The Merck Veterinary Manual ($10^{th}$ Edition, 2010), the commonly accepted routine laboratory techniques and physical examinations used to diagnose and monitor the common risk factors for contrast-induced nephropathy. For example, the definitive diagnosis of multiple myeloma can be made in about 95% of the patients after a bone marrow aspiration or bone marrow biopsy. In the other patients, the bone marrow involvement is probably focal rather than diffuse. In a preferred embodiment, serum and urinary levels of the monoclonal free light-chain immunoglobulin (Bence-Jones protein) are monitored with a highly sensitive nephelometric assay.

The present invention provides methods for treating, managing, preventing, and/or reducing damage caused by one or more iodinated radiocontrast agents to the kidney of humans or other mammals by the therapeutic or prophylactic administration of effective amounts of one or more compositions of the present invention. In another embodiment, the composition of the present invention can be administered in combination with one or more other cytoprotective agents.

The methods and compositions of the present invention comprise the administration of one or more compositions of the invention to subjects with one or more risk factors who have suffered from, are suffering from, or are expected to suffer from the side-effects of one or more iodinated radiocontrast agents. In a preferred embodiment, the subject has been, is being, or is expected to be administered one or more iodinated radiocontrast agents. In the most preferred embodiment, the subject is expected to be treated for the first and only time with an iodinated radiocontrast media.

The subjects may or may not have previously been treated on one or more occasions with one or more iodinated radiocontrast agents. The methods and compositions of the present invention may be used as an adjuvant for a first line, second line or nonstandard iodinated radiocontrast agent. The methods and compositions of the present invention can be used before any side-effects of one or more iodinated radiocontrast agents have been observed or after the first or later observations of any side-effects of one or more iodinated radiocontrast agents.

Other Therapeutic/Prophylactic Agents

The present invention provides methods for treating, managing, preventing, and/or reducing injuries to one or more organs, such as the kidney, of a human or other mammal caused by one or more iodinated radiocontrast media by administering one or more compositions of the present invention that include a PACAP-like compound. The methods may also include administering one or more other cytoprotective agents in combination with the PACAP-like compound. These other cytoprotective agents include (but are not limited to) ascorbic acid, vitamin E, mesna, palifermin (human keratinocyte growth factor), erythropoietin, apocynin, diphenylene iodonium, pentoxifylline, etanercept, simvastatin, amifostine, dexrazoxane, and N-acetylcysteine. All of these cytoprotective agents have mechanisms of action that are distinct from the presumed cytoprotective mechanisms of action of PACAP-like peptides. One or more of these cytoprotective agents can have additive or even synergistic effects when administered in combination with PACAP-like peptides.

In another embodiment, the present invention provides methods for treating, managing, preventing, and/or reducing injuries to one or more organs, such as the kidney, of a human or other mammal caused by one or more iodinated radiocontrast media by administering one or more compositions of the present invention in combination with one or more vasodilators and/or vasoconstrictor antagonists. These vasodilators and vasoconstrictor antagonists include (but are not limited to) fenoldopam, SB 209670, atrial natriuretic peptide, theophylline, and aminophylline. One or more of these vasodilators and/or vasoconstrictor antagonists can have additive or even synergistic effects when administered in combination with PACAP-like peptides.

Synthesis of PACAP38, PACAP27, VIP, and Related Analogs

Except for a few unusual instances where incompatible chemistries are encountered, all analogs may be prepared by modified Merrifield solid-phase procedures using Boc chemistries and hydrogen fluoride (HF) resin cleavage. Briefly, a Me-benzhydrylamine resin is used to yield amides directly after HF cleavage. Forty percent trifluoroacetic acid (TFA)/methylene chloride is used for Boc removal and couplings are achieved by diisopropylcarbodiimide (DIC) or TBTU/DIPEA activation or DIC/HOBt preactivation and active ester coupling. We estimate that approximately 20% of the couplings, which are monitored at each stage by the Kaiser ninhydrin test, fail to reach completion in 1 hour. Almost all of these resistant couplings can be driven to completion in 15-30 minutes by repeated coupling of the corresponding HOBt activated ester in dimethylformamide to which a catalytic amount of dimethylaminopyridine can be added for additional coupling power. CS Bio automated peptide synthesizers allow all of these pre-activations, double couplings, etc. to be fully automated with a concomitant increase in the speed of synthesis. Side-chain protection groups commonly used are: Asp and Glu, cHex; Ser and Thr, Bzl; Arg and His, tosyl (or Bom for His); Lys, 2-Cl-Z; and Tyr, 2-Br-Z.

Peptides are simultaneously deprotected and cleaved from the resin support by treatment at 0° C. for 45 minutes with anhydrous HF containing 15% anisole. Excess HF is removed rapidly (~10 minutes) under a rapid flow of dry nitrogen. With linear peptides, the resin is extracted with 2 M acetic acid and applied directly to preparative chromatography systems (either 1.5 or 2.5×25 cm columns) containing Vydac C-18 or phenyl-silica of 300-angstrom pore size (particle size 10 µm). Two fully volatile solvent elution systems have been used successfully for all of these peptides: linear gradient of acetonitrile in 0.1% TFA and acetonitrile in 20% acetic acid (excellent for insoluble peptides) at flow rates of about 8-20 ml/min. Gradients are generated with Rainin programmable high-performance liquid chromatography (HPLC) pumps and a typical separation run would normally be completed within 1 hour.

A long-chain saturated fatty acid is covalently linked to the free epsilon-amino group of one of the four Lys residues near the C-terminus of PACAP38 or one of the PACAP38 analogs (e.g., SEQ ID NO:5 and SEQ ID NO:6). PACAP27 and PACAP38 have similar affinities for the $PAC_1$, $VPAC_1$ and $VPAC_2$ receptors suggesting that the additional 11 amino acids are not essential for high-affinity receptor binding. The fatty acid attachment will promote high-affinity binding to serum albumin (Kurtzhals et al., *J Pharm Sci* 85:304-308, 1996), which is by far the most abundant protein in the serum. This strategy has been used to make long-acting analogs of GLP-1 (Knudsen et al., *J Med Chem* 43:1664-1669, 2000), which is a member of the secretin/VIP/PACAP family.

The purity of each purified compound was confirmed by analytical HPLC, and structure by amino acid analysis (post-hydrolysis, pre-HPLC column labeling with fluorescamine) and matrix-assisted laser desorption/ionization (MALDI) mass spectroscopy.

Mouse Model of Contrast-Induced Nephropathy

The development of therapeutics for the treatment, management, prevention, and/or reduction of injury to one or more organs, such as the kidney, of a human or other mammal caused by one or more iodinated radiocontrast media has been hampered by the lack of a simple and reproducible mouse model of contrast-induced nephropathy. Wild-type mice, like healthy humans, are resistant to contrast-induced nephropathy. The inhibition of nitric oxide synthases and cyclooxygenases with $N^G$-nitro-L-arginine methyl ester (L-NAME) and indomethacin, respectively, has been used to make mice more sensitive to iodinated radiocontrast media (e.g., Billings et al., *Am J Physiol Renal Physiol* 295:F741-F748, 2008). However, these two nonspecific inhibitors interfere with the mechanisms that normally mediate contrast-induced nephropathy and add multiple sources of variance to the experiments.

We have, therefore, used homozygous endothelial nitric oxide synthase (eNOS)-deficient mice, which have increased blood pressure and decreased heart rate compared to wild-type mice (Shesely et al., *Proc Natl Acad Sci USA* 93:13176-13181, 1996), to produce a simple and reproducible mouse model of contrast-induced nephropathy. Mice with homozygous deficiency of both eNOS and either leptin or the leptin receptor provide a clinically relevant model for the patient population that is at the highest risk for developing contrast-induced nephropathy.

Therapeutic Testing and Monitoring

The protocols and compositions of the present invention may be tested in vitro, and then in preclinical models in vivo, for the desired therapeutic or prophylactic activity, prior to use in humans. For example, in vitro assays that can be used to determine whether administration of a specific therapeutic protocol is indicated include in vitro cell culture assays in which an appropriate cell line or a biopsy of a patient's tissue is grown in culture and exposed to or otherwise administered a protocol and the effect of such protocol upon the cells or tissue is observed. For example (but not by way of limitation), rescuing of renal epithelial cells, hepatocytes or cardiomyocytes; decreased activation of NFκB or NFAT; decreased survival or proliferation of B- or T-lymphocytes; or decreased production of TNF-α, monocyte chemotactic protein-1 (MCP-1, CCL2) or KIM-1. A demonstration of one or more of the aforementioned properties of the exposed cells or tissue indicates that the therapeutic agent is effective for treating the condition in the patient. Many assays standard in the art can be used to assess such survival and/or growth of renal epithelial cells, hepatocytes and/or B- or T-lymphocytes. Furthermore, any of the assays known to those skilled in the art can be used to evaluate the prophylactic and/or therapeutic utility of the combination therapies disclosed herein for treatment, management, prevention, and/or reduction of injuries to one or more organs of the body of humans or other mammals caused by one or more iodinated radiocontrast media.

The injuries to one or more organs of the body of humans or other mammals caused by one or more iodinated radiocontrast media can be monitored in the subjects with commonly used biomarkers. For example (but not by way of limitation), injury to the kidney can be monitored by determining the concentration of KIM-1, netrin-1 or protein in the urine, or the concentration of creatinine, cystatin C or urea nitrogen in the bloodstream. Injury to the liver can be monitored by determining the enzyme activity or concentration of alanine aminotransferase in the bloodstream, or the concentration of conjugated bilirubin in the urine. Injury to the heart can be monitored by determining the concentration of troponin I or the MB isoenzyme of creatinine kinase in the bloodstream. Injury to the β-cells of the pancreas can be monitored by determining the activity or concentration of glutamic acid decarboxylase in the bloodstream.

The injuries to one or more organs of the body of humans or other mammals caused by one or more iodinated radiocontrast media can also be monitored in the subjects with commonly used imaging techniques. For example (but not by way of limitation), injury to the heart can be monitored by electrocardiography or serial echocardiography.

The injuries to one or more organs of the body of humans or other mammals caused by one or more iodinated radiocontrast media can also be monitored in the subjects with commonly used functional tests. For example (but not by way of limitation), injury to the kidney can be monitored by determining the glomerular filtration rate with sodium $^{125}$I-iothalamate clearance. Injury to the heart can be monitored with a variety of exercise tests.

Pharmaceutical Composition

The compositions of the present invention include bulk drug compositions useful in the manufacture of pharmaceutical compositions (e.g., impure or non-sterile compositions) and parenteral pharmaceutical compositions (i.e., compositions that are suitable for administration to a subject or patient) which can be used in the preparation of unit dosage forms. Such compositions include a prophylactically or therapeutically effective amount of a prophylactic and/or therapeutic agent disclosed herein or a combination of those agents and a pharmaceutically acceptable carrier. Preferably, compositions of the present invention include a prophylactically or therapeutically effective amount of one or more PACAP-like compounds useful in the method of the invention and a pharmaceutically acceptable carrier. In a further embodiment, the composition of the present invention further includes an additional therapeutic agent, as is discussed above.

In a specific embodiment, the term "pharmaceutically acceptable" means approved by a regulatory agency of the Federal government or listed in the U.S. Pharmacopeia or other generally recognized pharmacopeia for use in animals, and particularly for use in humans. The term "carrier" refers to a diluent, adjuvant (e.g., Freund's adjuvant or, more preferably, MF59C.I adjuvant), excipient, or vehicle with which the therapeutic is administered. The pharmaceutical carriers can be sterile liquids, such as water and oils, including those of petroleum, animal, vegetable or synthetic origin, such as peanut oil, soybean oil, mineral oil, sesame oil. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include (but are not limited to) starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. The composition, if desired, can also contain minor amounts of wetting or emulsifying agents, or pH buffering agents. These compositions can take many forms, including (but not limited to) suspensions, emulsions, tablets, pills, capsules, powders, and sustained-release formulations.

Generally, the ingredients of the compositions of the present invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the present invention can be formulated as neutral or salt forms. Pharmaceutically acceptable salts include (but are not limited to) those formed with anions such as those derived from hydrochloric acid, phosphoric acid, acetic acid, oxalic acid, and tartaric acid, and those formed with cations such as those derived from sodium, potassium, ammonium, calcium, ferric hydroxides, isopropylamine, triethylamine, 2-ethylamino ethanol, histidine, and procaine.

As desired, additives such as a dissolution aid (e.g., sodium salicylate or sodium acetate), a buffer (e.g., sodium citrate or glycerin), an isotonizing agent (e.g., glucose or invert sugar), a stabilizer (e.g., human serum albumin or polyethylene glycol), a preservative (e.g., benzyl alcohol or phenol), or an analgesic (e.g., benzalkonium chloride or procaine hydrochloride) may be added.

There are many delivery methods known to those skilled in the art that can be used to administer the PACAP-like compound(s), or the PACAP-like compound(s) in combination with other cytoprotective agents, in order to treat, manage, prevent, or reduce injuries to one or more of the organs of the body of humans or other mammals caused by one or more iodinated radiocontrast media. For example (but not by way of limitation), encapsulation in liposomes (see, e.g., Sethi et al., *Methods Enzymol* 391:377-395, 2005), microparticles or microcapsules (see, e.g., Almeida & Souto, *Adv Drug Deliv Rev* 59:478-490, 2007), secretion from mammalian cells genetically engineered to synthesize one or more PACAP-like peptides, or synthesis by various recombinant viral vectors. The routes of administration of the PACAP-like compounds of the present invention include (but are not limited to), parenteral (e.g., intradermal, intramuscular, intraperitoneal, intravenous, and subcutaneous), vaginal, rectal, epidural, and mucosal (e.g., intranasal, inhaled, and oral routes). In a specific embodiment, prophylactic or therapeutic agents of the present invention are administered intramuscularly, intravenously, intraosseously, or subcutaneously. The prophylactic or therapeutic agents may be administered by any convenient route or regimen, for example by infusion or a bolus injection, by absorption through epithelial or mucocutaneous linings (e.g., oral mucosa, rectal, topical, including buccal and sublingual, and intestinal mucosa, etc.) and may be administered in combination with other biologically active agents. Administration can be systemic or local.

In a specific embodiment, it may be desirable to administer the prophylactic or therapeutic agents of the present invention locally to the area in need of treatment; this maybe achieved by, for example, but not by way of limitation, local infusion, by injection, or by means of an implant, said implant being of a porous, non-porous, or gelatinous material, including membranes, such as Silastic membranes, or fibers.

In another embodiment, the compositions of the invention can be delivered in a controlled release (see, e.g., Kost & Langer, *Adv Drug Deliv Rev* 46:125-148, 2001) or a sustained-release (see, e.g., Hutchinson & Furr, *J Control Release* 13:279-294, 1990) manner. In one embodiment, a pump can be used to achieve controlled or sustained release. In another embodiment, polymeric materials can be used to achieve controlled release or sustained release. Suitable polymers for controlled release or sustained release formulations include (but are not limited to) poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a controlled release or a sustained release formulation is inert, free of leachable impurities, stable on storage, sterile, and biodegradable. In a specific embodiment, a controlled release, or a sustained release device or formulation can be placed in proximity of the prophylactic or therapeutic target, thus reducing the required amount of the PACAP-like compound to only a fraction of the systemic dose. Many other techniques known to one skilled in the art can be used to produce controlled release or sustained release formulations comprising one or more therapeutic agents of the present invention.

The compositions for administration of the PACAP-like compounds include (but are not limited to) those suitable for oral, rectal, nasal, topical (including buccal and sublingual), vaginal, or parenteral (including subcutaneous, transcutaneous (e.g., the PACAP-like compounds may be encapsulated in dendrimers (see, e.g., Grayson & Fréchet, *Chem Rev* 101: 3819-3868, 2001)), intramuscular, intravenous, and intradermal) administration. The formulations may conveniently be presented in unit dosage forms and may be prepared by any method well known in the art of pharmacy. Thus, the PACAP-like compounds of the present invention and their physiologically acceptable salts and solvates may be formulated for administration by inhalation or insufflation (either through the mouth or the nose), or by oral, parenteral or mucosal (such as buccal, vaginal, rectal, and sublingual) routes. In a preferred embodiment, parenteral administration is used. In several embodiments, the PACAP-like compound is administered to a mammal in need thereof, (e.g., a human) at a dose in the range of 1 µg to 1 gram (e.g., 100 to 5000 µg, such as about 500 µg).

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium dodecyl sulfate). The tablets may be coated by methods well known in the art. Liquid preparations for oral administration may take the form of, for example, solutions, syrups or suspensions, or they may be presented as a dry product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated to give controlled release or sustained release of the active compound.

For buccal administration, the compositions of the present invention may be conventionally formulated as tablets or lozenges.

For administration by inhalation, the prophylactic or therapeutic agents for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The prophylactic or therapeutic agents may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in a powder form for reconstitution before use with a suitable vehicle, e.g., sterile pyrogen-free water.

In addition to the formulations described previously, the prophylactic or therapeutic agents may also be formulated as a depot preparation. Such long-acting formulations may be administered by implantation (e.g., subcutaneously or intramuscularly) or by intramuscular injection. Thus, for example, the prophylactic or therapeutic agents may be formulated with suitable polymeric or hydrophobic materials (e.g., as an emulsion in an acceptable oil) or ion-exchange resins, or as sparingly soluble derivatives, for example, as a sparingly soluble salt.

Compositions suitable for topical administration to the skin may be presented as ointments, creams, gels, and pastes comprising the compound and a pharmaceutically acceptable carrier. For example (but not by way of limitation), a suitable topical delivery system is a transdermal patch containing the PACAP-like compound to be administered.

Sublingual tablets can be prepared by using binders (e.g., hydroxypropylcellulose, hydroxypropylmethylcellulose, or polyethylene glycol), disintegrating agents (e.g., starch or carboxymethylcellulose calcium), and/or lubricants (e.g., magnesium stearate or talc). Suitable formulations for nasal administration wherein the carrier is a solid include a coarse powder having a particle size, for example, in the range 20 to 500 microns (μm). Suitable formulations for nasal administration wherein the carrier is a liquid (e.g., a nasal spray or nasal drops) include aqueous or oily solutions of the active ingredient.

Compositions suitable for parenteral administration include aqueous and non-aqueous sterile injection solutions which may contain anti-oxidants, buffers, bacteriostatic agents, and solutes that make the formulation isotonic with the blood of the intended recipient; and aqueous and non-aqueous sterile suspensions that may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described. It should be understood that in addition to the ingredients specifically mentioned above, the formulations of this invention may include other agents commonly used in the art for the type of formulation in question. For example (but not by way of limitation), those suitable for oral administration may include flavoring agents.

EXAMPLES

In order to make the uses of the present invention clearer, the following examples are presented. These examples are only for illustrative purposes and should not be interpreted in any way as limitations in the uses of this invention.

Example 1

Reduction of Urografin-Induced Renal Epithelial Cell Toxicity by PACAP38, VIP and PACAP Analogs Iodinated radiocontrast media are used to enhance the visualization of blood vessels and internal organs for a wide range of diagnostic and/or interventional procedures. Nephrotoxicity is usually the "dose-limiting" toxicity for the use of iodinated radiocontrast media as therapeutics. The toxic effects of short-term treatment with iodinated radiocontrast media on the kidney are characterized by a decrease in the glomerular filtration rate, which is usually assessed as an increase in creatinine or cystatin C in serum, and injury to the proximal tubule epithelial cells, which is assessed as an increase in KIM-1 or netrin-1 in the urine.

Figure 3:
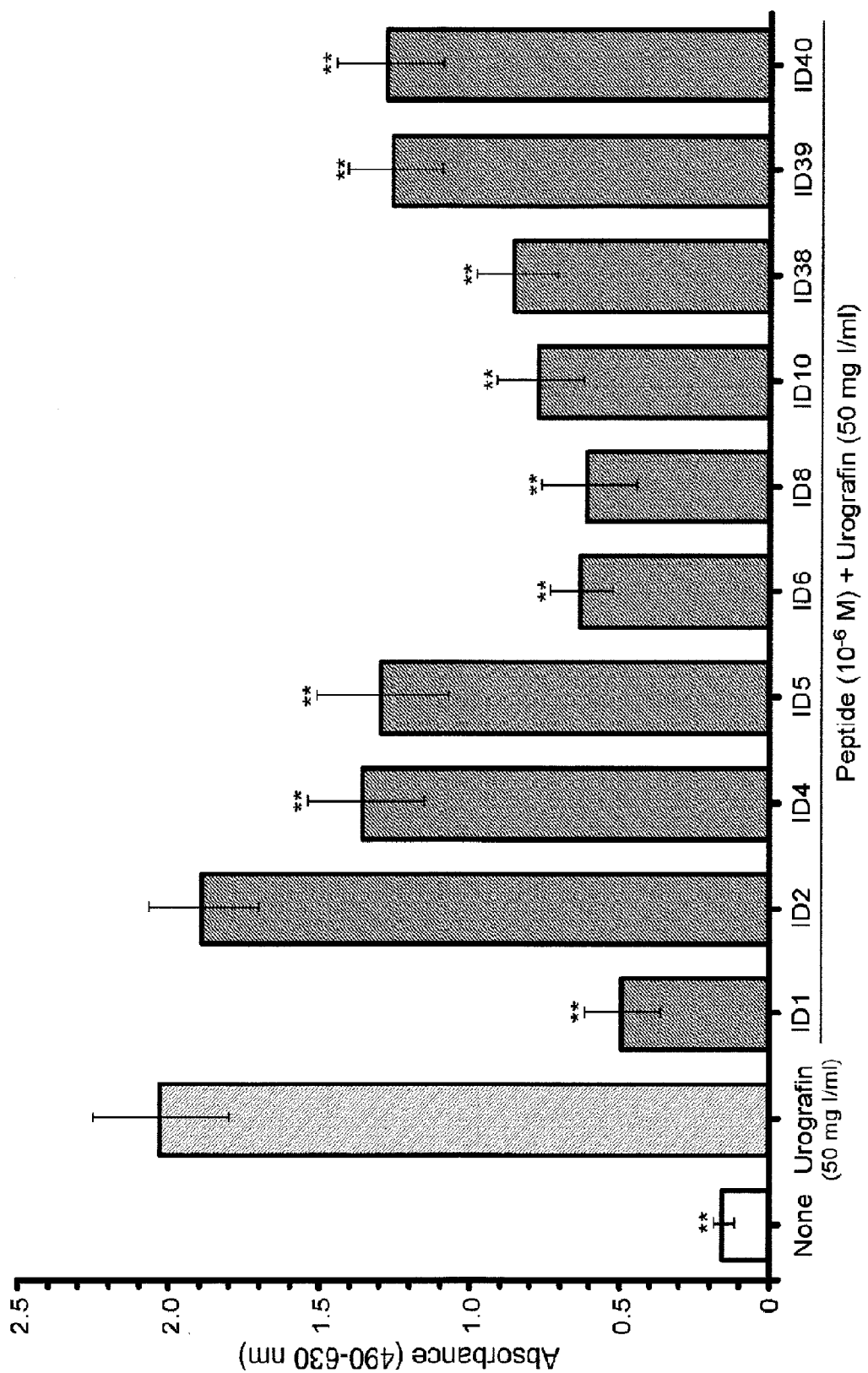
FIG. 3 shows the reduction by PACAP38 and PACAP analogs of the injury (cytotoxicity) to human renal proximal tubule epithelial cells caused by treatment with Urografin. The HK-2 human kidney cells were cultured in Keratinocyte-Serum Free Medium supplemented with recombinant epidermal growth factor and bovine pituitary extract. The effects of PACAP38 or PACAP analogs on cell injury were assessed by determining the activity of the cytoplasmic enzyme lactate dehydrogenase in the culture medium. Each value represents the mean plus/minus the standard error of eight determinations. $**p<0.01$ and $*p<0.05$ compared to the cells treated only with Urografin. The ID numbers in the figure correspond to the SEQ ID NO numbers in the Sequence Listing. ID1=PACAP38, ID2=PACAP27, ID4=[D-Ser$^2$]PACAP38, ID5=[Aib$^2$]PACAP38, ID6=[D-Ser$^2$,Lys$^{38}$-palmitoyl]PACAP38, ID8=[Ala$^{22}$]PACAP38, ID10=[Lys$^{34}$]PACAP38, ID38=N-acetyl[Pip$^3$]PACAP38, ID39=[Pip$^3$,Ala$^{14,17}$,Aib$^{16,28}$,Lys$^{34}$, D-Lys$^{38}$]PACAP38, and ID40=[Pip$^3$,Ala$^{15,17}$,Aib$^{16,28}$,Lys$^{34}$,D-Lys$^{38}$]PACAP38.
Figure 5:
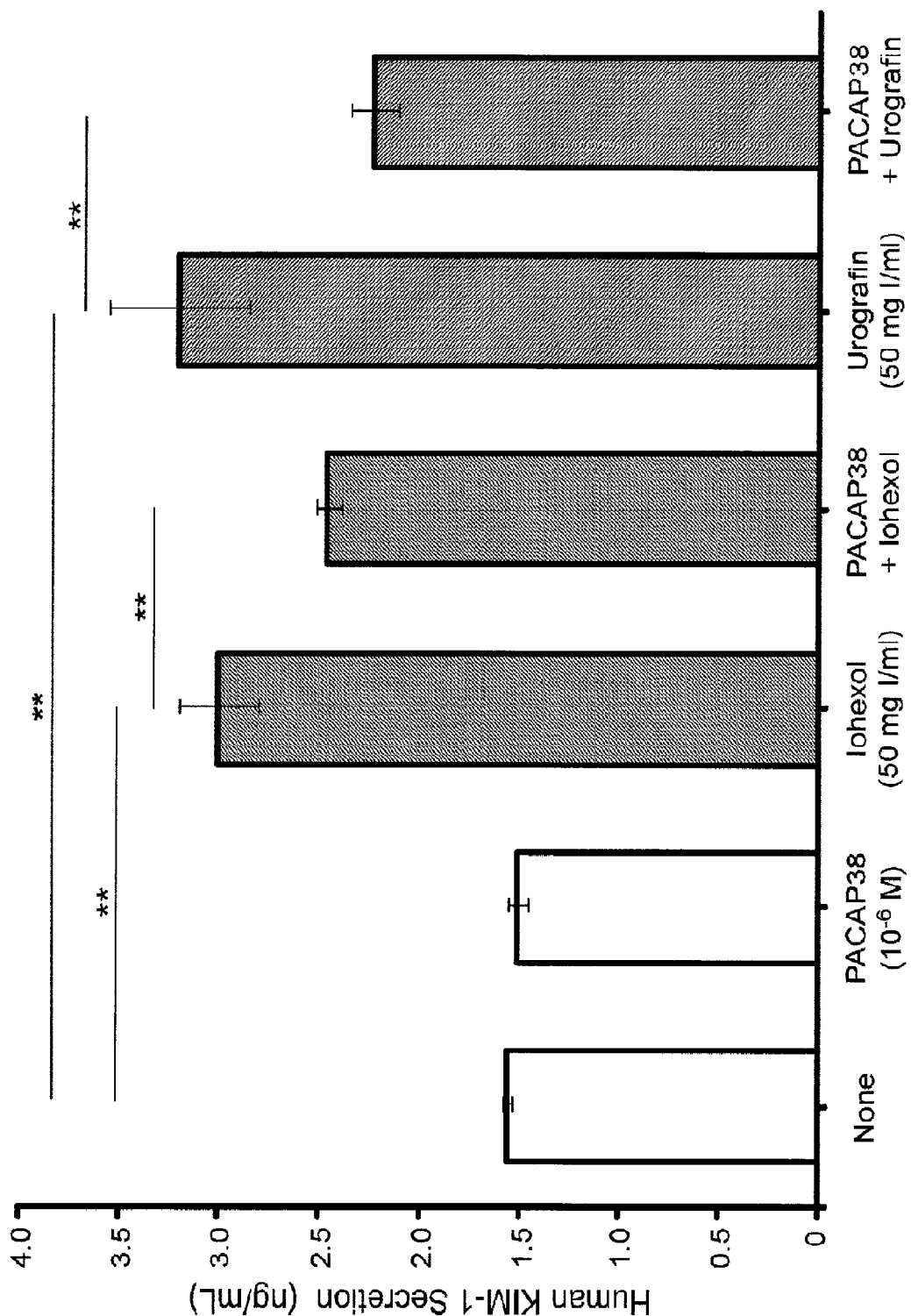
FIG. 5 shows the reversal by PACAP38 of the increase of the secretion of KIM-1 by human renal proximal tubule epithelial cells caused by treatment with Urografin or iohexol. The HK-2 human kidney cells were cultured in Keratinocyte-Serum Free Medium supplemented with recombinant epidermal growth factor and bovine pituitary extract. The effects of $10^{-6}$ M PACAP38 on the excretion of KIM-1 were assessed by determining the concentration of KIM-1 in the culture medium with an enzyme-linked immunosorbent assay. Each value represents the mean plus/minus the standard error of three determinations. $**p<0.01$ and $*p<0.05$ compared to the cells treated only with Urografin.
Figure 6:
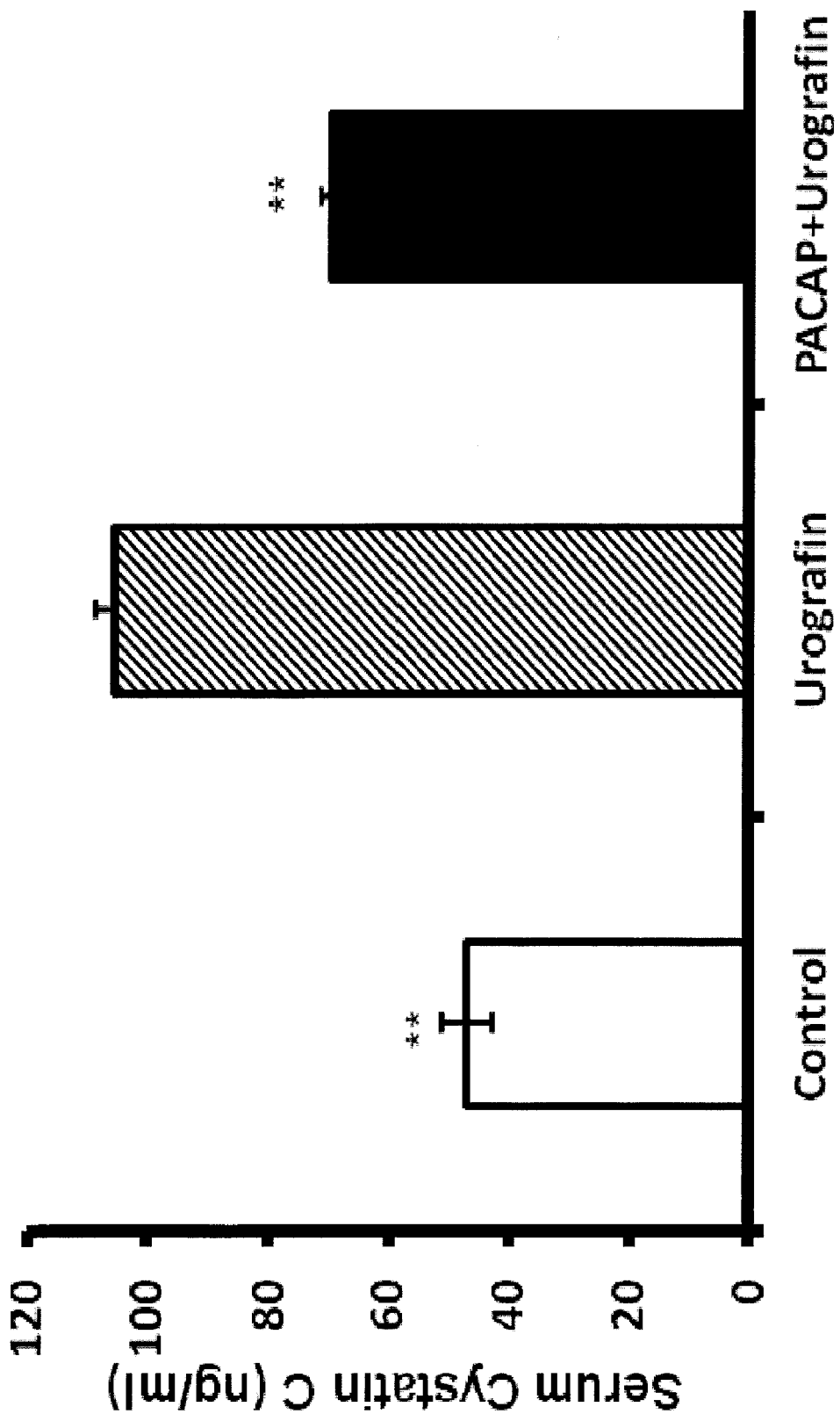
FIG. 6 shows the effects of PACAP38 on serum cystatin C levels in mice treated with Urografin. Male homozygous eNOS-deficient mice were given a single intravenous injection of Urografin at a dose of 1.85 g iodine/kg body weight. The mice were deprived of water for 24 hours before the start of the experiment. Twenty micrograms of PACAP38 were given intraperitoneally 1 hour before the injection of Urografin and an additional dose was given 12 hours later. The control group of mice was injected intravenously with the same volume of saline as for the injections of Urografin and PACAP38 on the same schedule. The mice were euthanized 72 hours after the injection of Urografin. The concentration of cystatin C in serum was determined with an enzyme-linked immunosorbent assay. Each value represents the mean plus/minus the standard error of five or eight determinations. $**p<0.01$ compared to the group treated with Urografin and saline.
Figure 7:
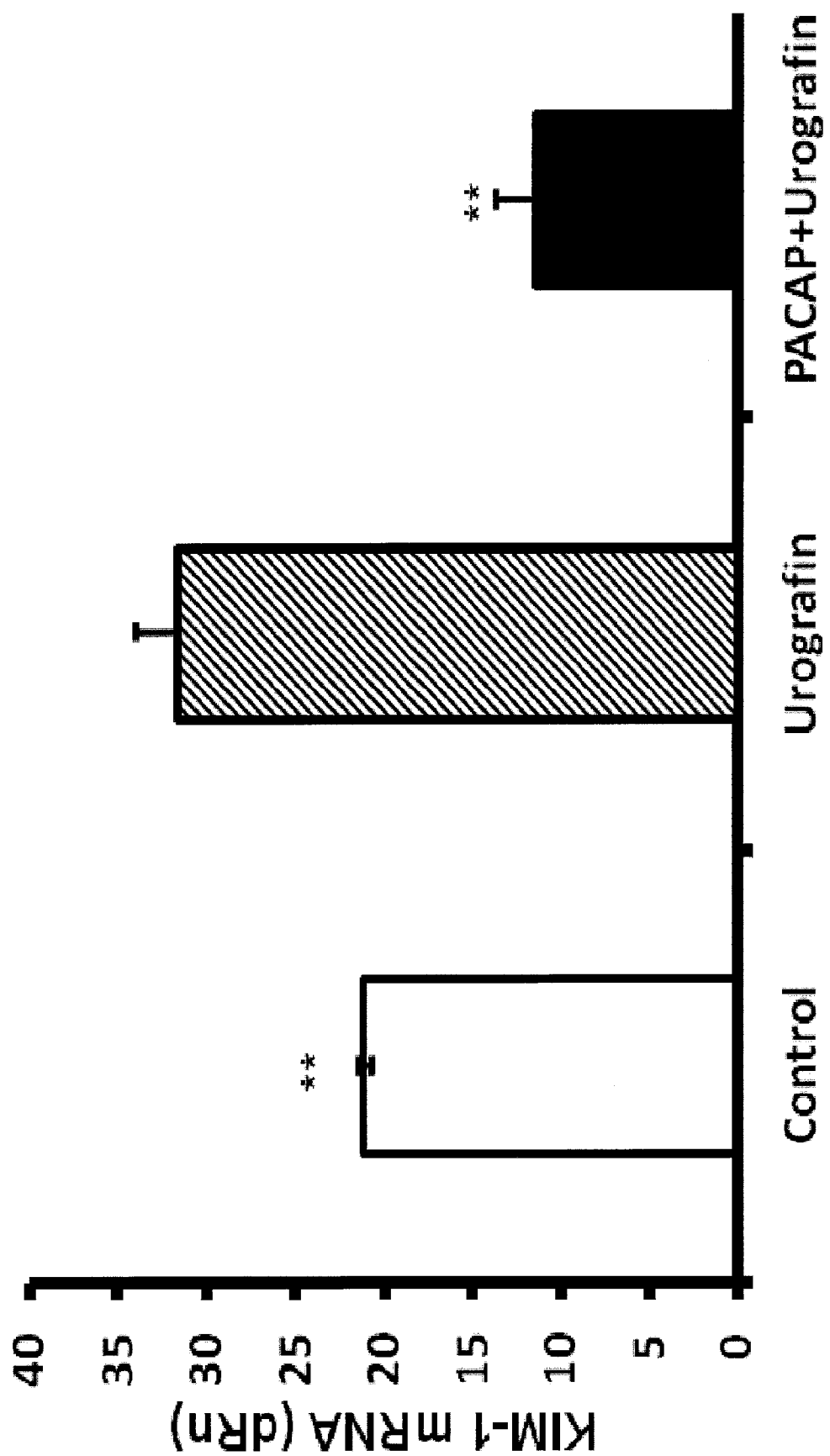
FIG. 7 shows the effects of PACAP38 on the levels of KIM-1 mRNA in the kidneys of mice treated with Urografin. Male homozygous eNOS-deficient mice were given a single intravenous injection of Urografin at a dose of 1.85 g iodine/kg body weight. The mice were deprived of water for 24 hours before the start of the experiment. Twenty micrograms of PACAP38 were given intraperitoneally 1 hour before the injection of Urografin and an additional dose was given 12 hours later. The control mice were injected intravenously with the same volume of saline as for the injections of Urografin and PACAP38 on the same schedule. The mice were euthanized 72 hours after the injection of Urografin. Quantification of mRNA levels for KIM-1 was made by real-time reverse transcriptase polymerase chain reaction analyses. Each value represents the mean plus/minus the standard error of five or eight determinations. $**p<0.01$ compared to the group treated with Urografin and saline.

Treatment of human renal proximal tubule epithelial cells with Urografin resulted in a large significant increase in the activity of lactate dehydrogenase in the culture medium (FIG. 2). The addition of PACAP38 to the medium resulted in a significant dose-dependent reduction in Urografin-induced cell death of the human renal proximal tubule epithelial cells. At the highest dose tested, PACAP38 reduced the cell death caused by Urografin by more than 70%. The addition of VIP to the medium also resulted in a significant dose-dependent reduction in Urografin-induced cell death of the human renal proximal tubule epithelial cells. PACAP was significantly more potent than VIP. In addition, a wide variety of PACAP analogs significantly reduced the Urografin-induced cytotoxicity of human renal proximal tubule epithelial cells (FIG. 3). Treatment of human renal proximal tubule epithelial cells with Urografin also resulted in a large significant increase in the concentration of KIM-1 in the medium (FIG. 5). The addition of PACAP38 to the medium significantly reduced the Urografin-induced secretion of KIM-1 into the medium.

Figure 8:
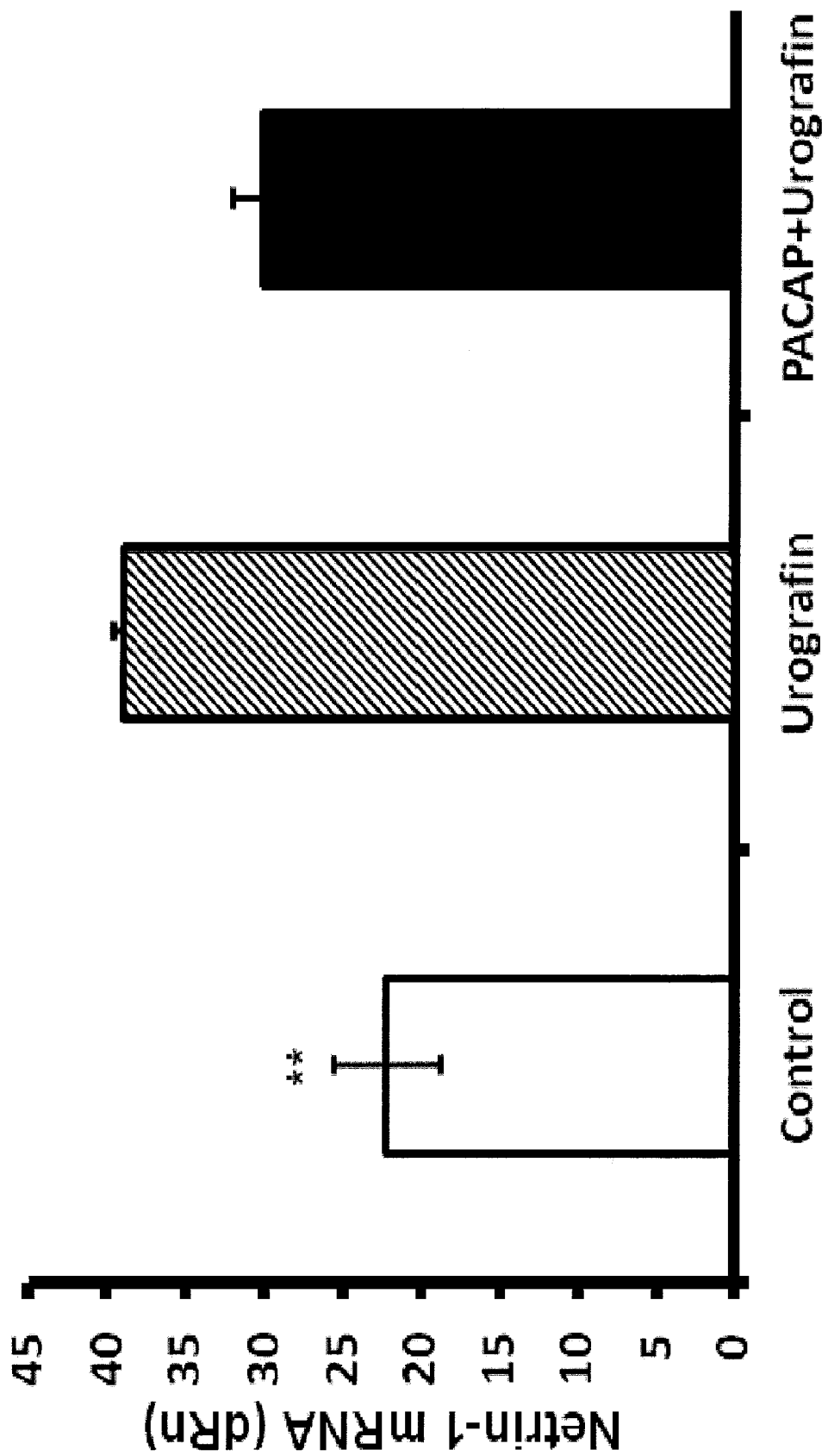
FIG. 8 shows the effects of PACAP38 on the levels of netrin-1 mRNA in the kidneys of mice treated with Urografin. Male homozygous eNOS-deficient mice were given a single intravenous injection of Urografin at a dose of 1.85 g iodine/kg body weight. The mice were deprived of water for 24 hours before the start of the experiment. Twenty micrograms of PACAP38 were given intraperitoneally 1 hour before the injection of Urografin and an additional dose was given 12 hours later. The control mice were injected intravenously with the same volume of saline as for the injections of Urografin and PACAP38 on the same schedule. The mice were euthanized 72 hours after the injection of Urografin. Quantification of mRNA levels for netrin-1 was made by real-time reverse transcriptase polymerase chain reaction analyses. Each value represents the mean plus/minus the standard error of five or eight determinations. $**p<0.01$ compared to the group treated with Urografin and saline.

The cytoprotective effect of PACAP38 against Urografin-induced nephrotoxicity was also seen in the in vivo model. Male homozygous eNOS-deficient mice were given a single intravenous injection of Urografin. Some of these mice were also given 20 μg of PACAP38 intraperitoneally 1 hour before the injection of Urografin and an additional dose 12 hours after the injection of Urografin. The mice treated only with Urografin had significantly increased serum levels of cystatin C (FIG. 6) and creatinine (FIG. 11), and significantly increased kidney levels of KIM-1 mRNA (FIG. 7), Nogo-B1 mRNA (FIG. 12) and netrin-1 mRNA (FIG. 8). Treatment of the Urografin-injected mice with PACAP38 reversed the increases in serum levels of cystatin C and creatinine, and reversed the increases in kidney levels of KIM-1 mRNA, Nogo-B1 mRNA and netrin-1 mRNA (FIGS. 6-8 and 11-12).

These experiments show that PACAP-like compounds protect the kidney against the toxic effects of ionic iodinated radiocontrast media.

Example 2

Reduction of Iohexol-Induced Renal Epithelial Cell Toxicity by PACAP38 and VIP

Figure 4:
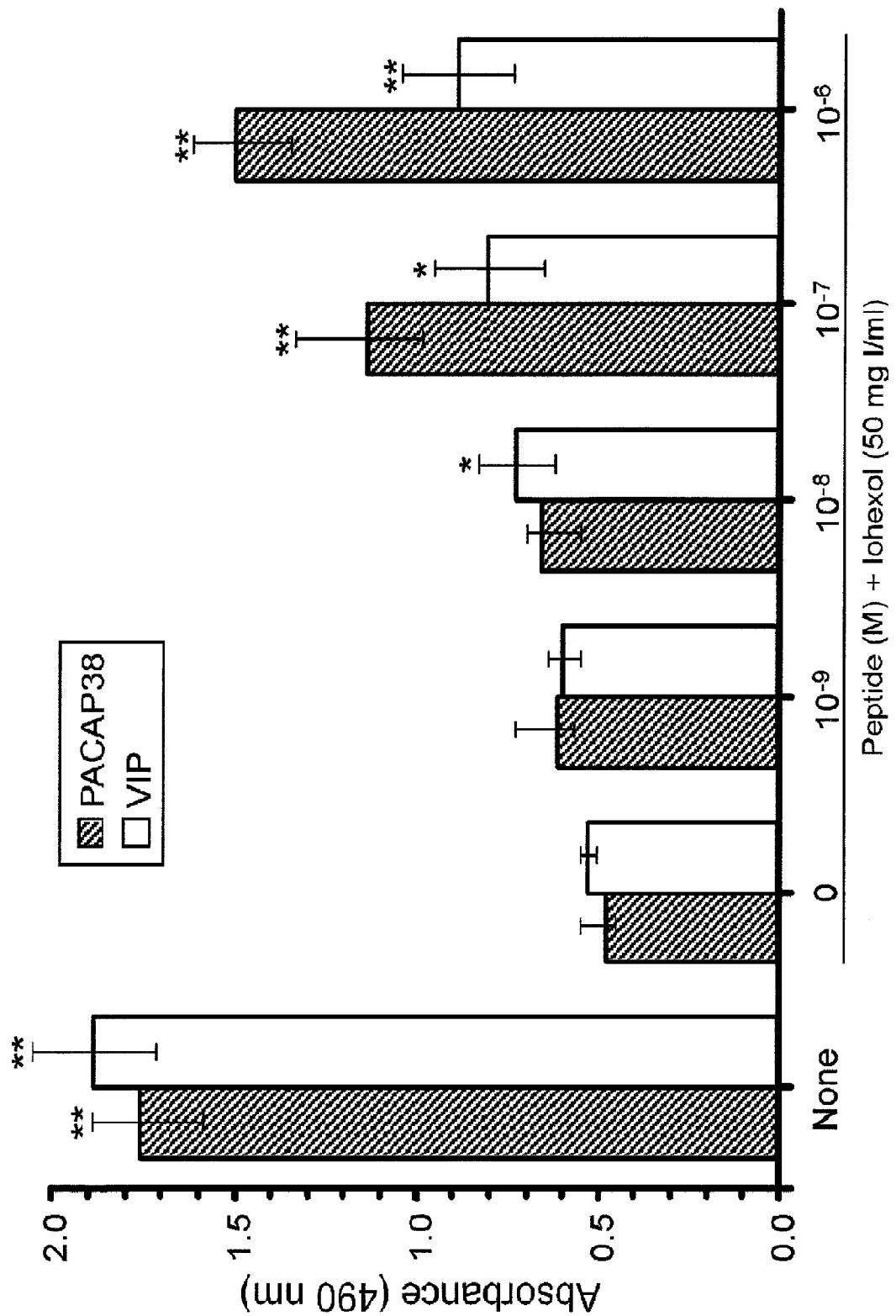
FIG. 4 shows the reversal by PACAP38 or VIP of the inhibition of the proliferation of human renal proximal tubule epithelial cells caused by treatment with iohexol. The HK-2 human kidney cells were cultured in Keratinocyte-Serum Free Medium supplemented with recombinant epidermal growth factor and bovine pituitary extract. The effects of various concentrations of PACAP38 or VIP on the inhibition of cell proliferation were assessed by determining the conversion of 3-(4,5-dimethylthiazol-2-yl)-2,5-diphenyltetrazolium bromide (MTT) to a purple formazan by reductases in intact cells. Each value represents the mean plus/minus the standard error of four determinations. $**p<0.01$ and $*p<0.05$ compared to the cells treated only with iohexol. PACAP38 was significantly more potent than VIP at both $10^{-7}$ M and $10^{-6}$ M.

Treatment of human renal proximal tubule epithelial cells with iohexol resulted in a large significant decrease in the number of viable cells (FIG. 4). The addition of PACAP38 or VIP to the medium resulted in a significant dose-dependent reduction in the loss of viable human renal proximal tubule epithelial cells caused by iohexol. At the highest dose tested, PACAP38 almost completely prevented the loss of viable human renal proximal tubule epithelial cells caused by iohexol. PACAP38 was significantly more potent than VIP as a renoprotectant in this in vitro model. Treatment of human renal proximal tubule epithelial cells with iohexol also resulted in a large significant increase in the concentration of KIM-1 in the medium (FIG. 5). The addition of PACAP38 to the medium significantly reduced the iohexol-induced secretion of KIM-1 into the medium.

These experiments show that PACAP-like compounds protect the kidney against the toxic effects of nonionic iodinated radiocontrast media.

Example 3

Reduction of Urografin-Induced Inflammatory Responses in the Kidney by PACAP38

The toxic side-effects on the kidney of many commonly used therapeutics, such as cisplatin, cyclosporine A and gentamicin, are accompanied by robust inflammatory responses, including the up-regulation of many pro-inflammatory cytokines and chemokines.

Figure 9:
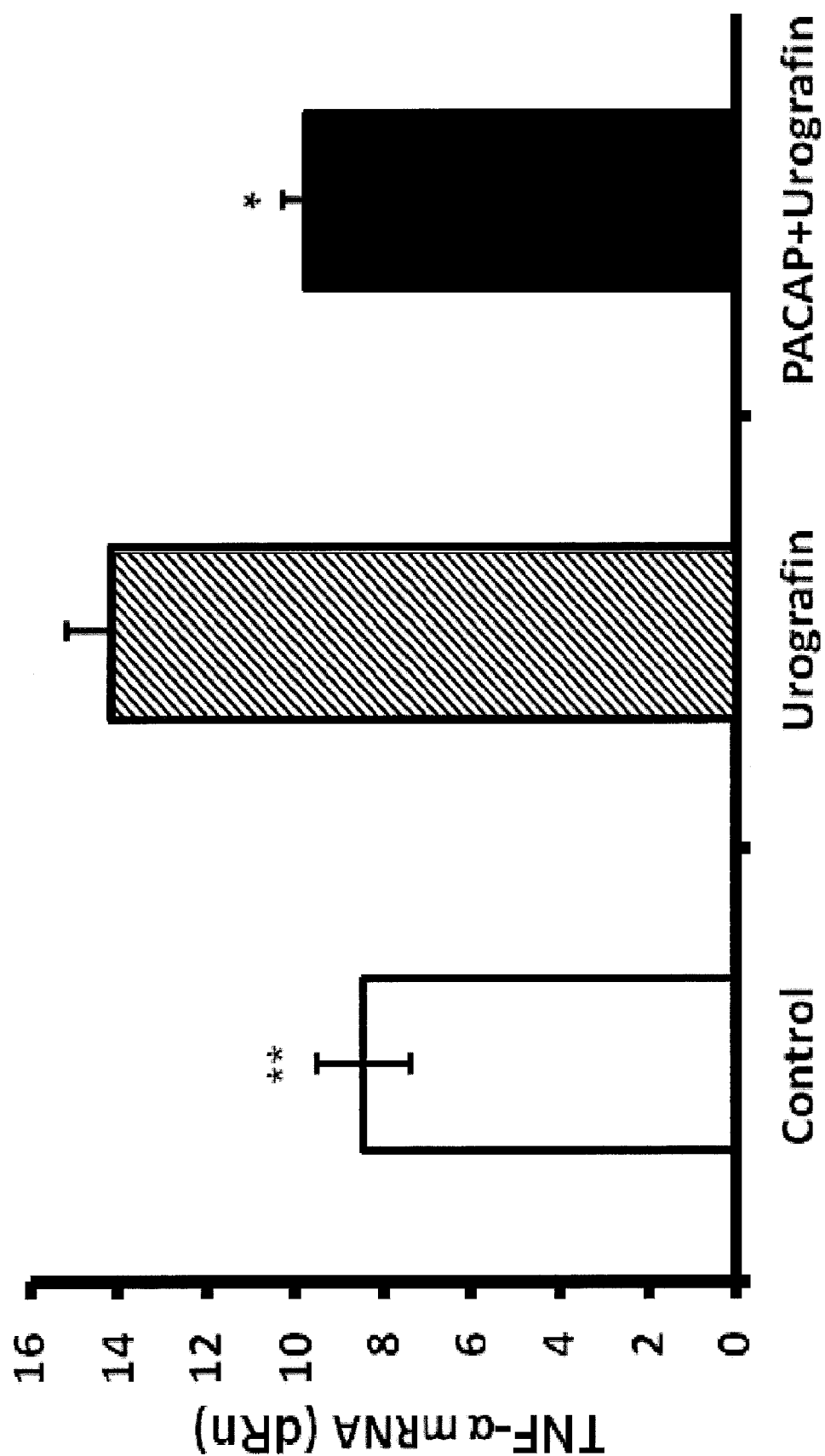
FIG. 9 shows the effects of PACAP38 on the levels of TNF-α mRNA in the kidneys of mice treated with Urografin. Male homozygous eNOS-deficient mice were given a single intravenous injection of Urografin at a dose of 1.85 g iodine/kg body weight. The mice were deprived of water for 24 hours before the start of the experiment. Twenty micrograms of PACAP38 were given intraperitoneally 1 hour before the injection of Urografin and an additional dose was given 12 hours later. The control mice were injected intravenously with the same volume of saline as for the injections of Urografin and PACAP38 on the same schedule. The mice were euthanized 72 hours after the injection of Urografin. Quantification of mRNA levels for TNF-α was made by real-time reverse transcriptase polymerase chain reaction analyses. Each value represents the mean plus/minus the standard error of five or eight determinations. $**p<0.01$ and $*p<0.05$ compared to the group treated with Urografin and saline.
Figure 10:
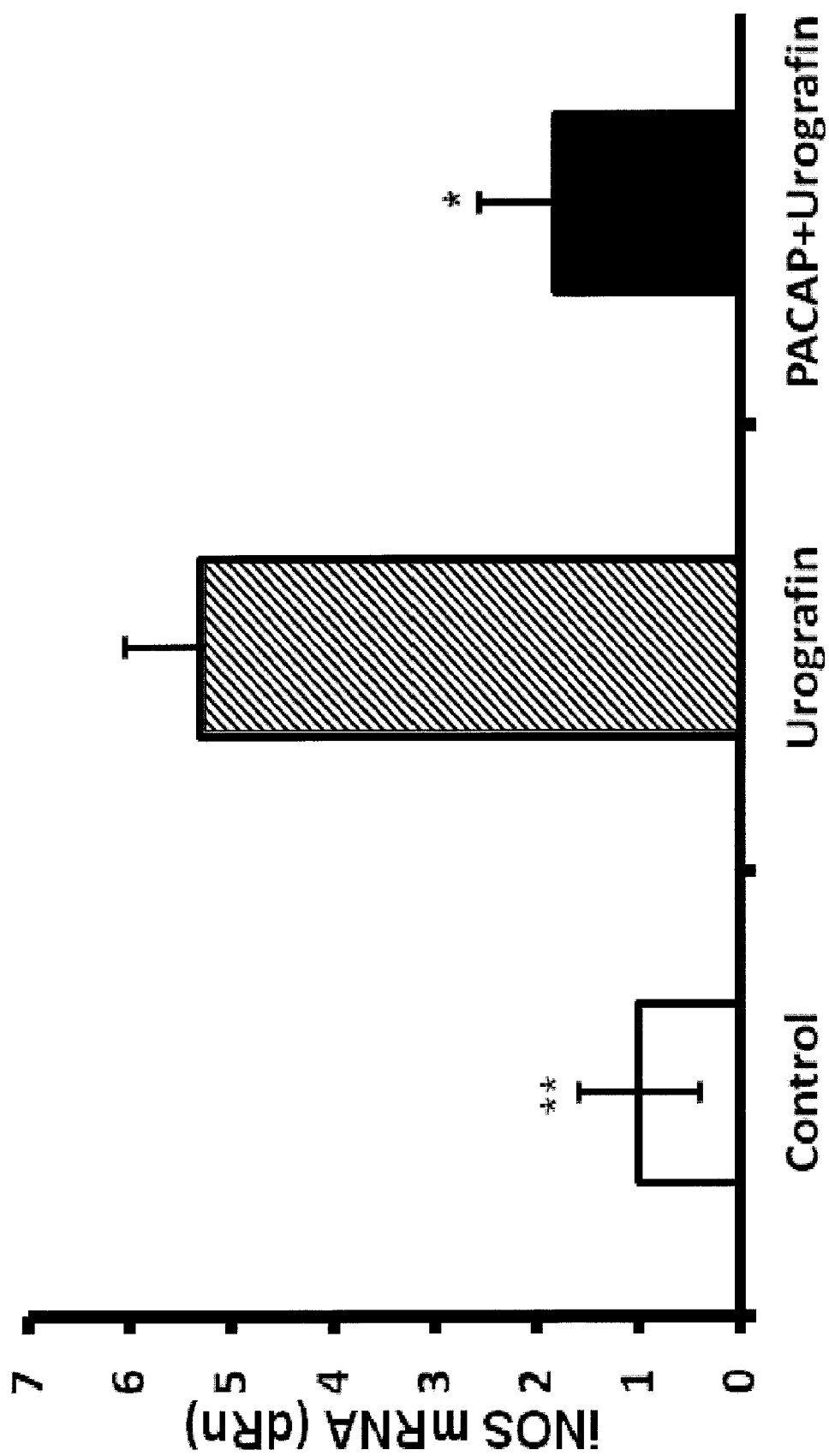
FIG. 10 shows the effects of PACAP38 on the levels of iNOS mRNA in the kidneys of mice treated with Urografin. Male homozygous eNOS-deficient mice were given a single intravenous injection of Urografin at a dose of 1.85 g iodine/kg body weight. The mice were deprived of water for 24 hours before the start of the experiment. Twenty micrograms of PACAP38 were given intraperitoneally 1 hour before the injection of Urografin and an additional dose was given 12 hours later. The control mice were injected intravenously with the same volume of saline as for the injections of Urografin and PACAP38 on the same schedule. The mice were euthanized 72 hours after the injection of Urografin. Quantification of mRNA levels for iNOS was made by real-time reverse transcriptase polymerase chain reaction analyses. Each value represents the mean plus/minus the standard error of five or eight determinations. $**p<0.01$ and $*p<0.05$ compared to the group treated with Urografin and saline.
Figure 11:
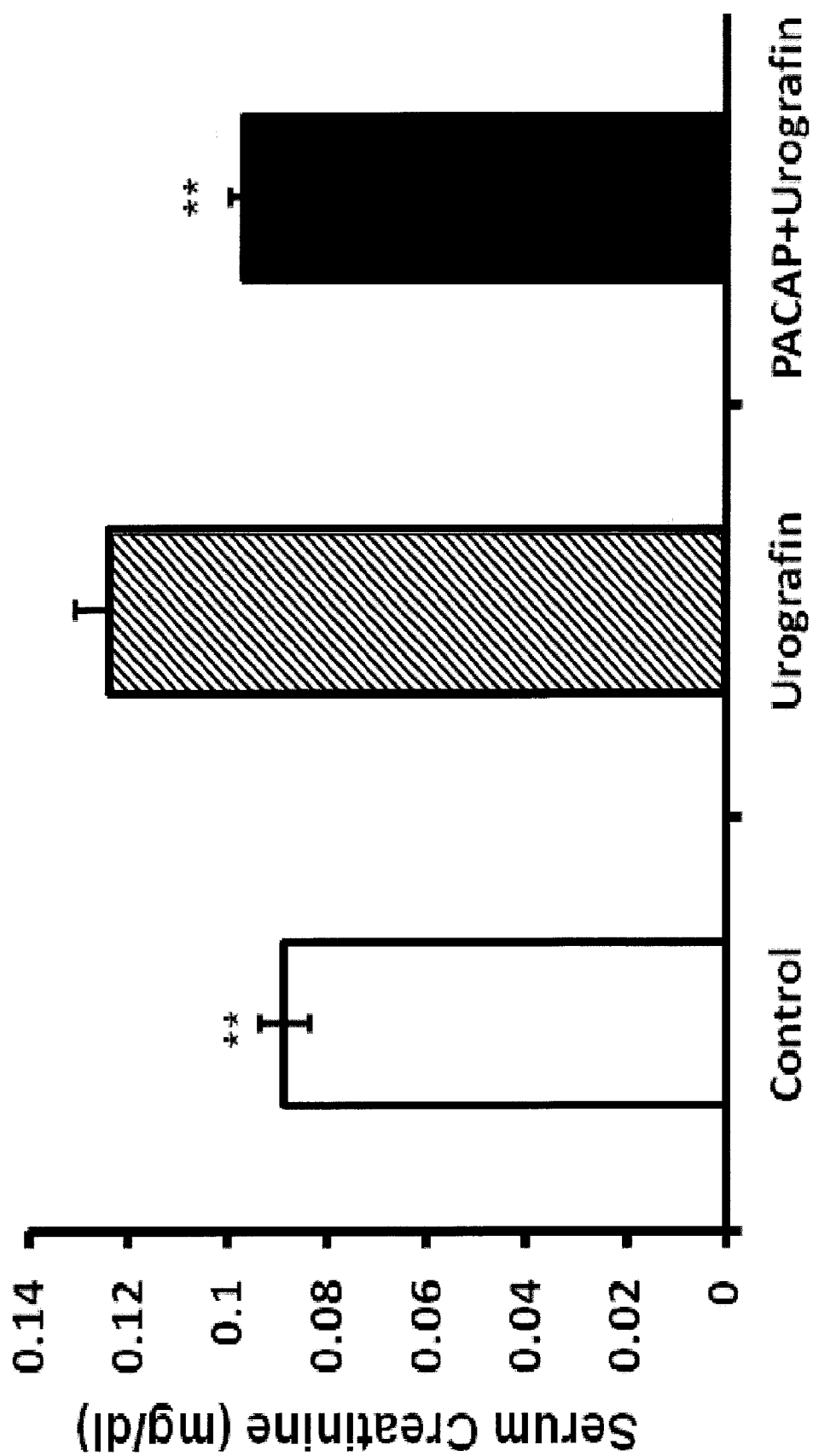
FIG. 11 shows the effects of PACAP38 on serum creatinine levels in mice treated with Urografin. Male homozygous eNOS-deficient mice were given a single intravenous injection of Urografin at a dose of 1.85 g iodine/kg body weight. The mice were deprived of water for 24 hours before the start of the experiment. Twenty micrograms of PACAP38 were given intraperitoneally 1 hour before the injection of Urografin and an additional dose was given 12 hours later. The control group of mice was injected intravenously with the same volume of saline as for the injections of Urografin and PACAP38 on the same schedule. The mice were euthanized 72 hours after the injection of Urografin. The concentration of creatinine in serum was determined by isotope dilution liquid chromatography-mass spectroscopy/mass spectroscopy. Each value represents the mean plus/minus the standard error of five or eight determinations. **$p<0.01$ compared to the group treated with Urografin and saline.
Figure 12:
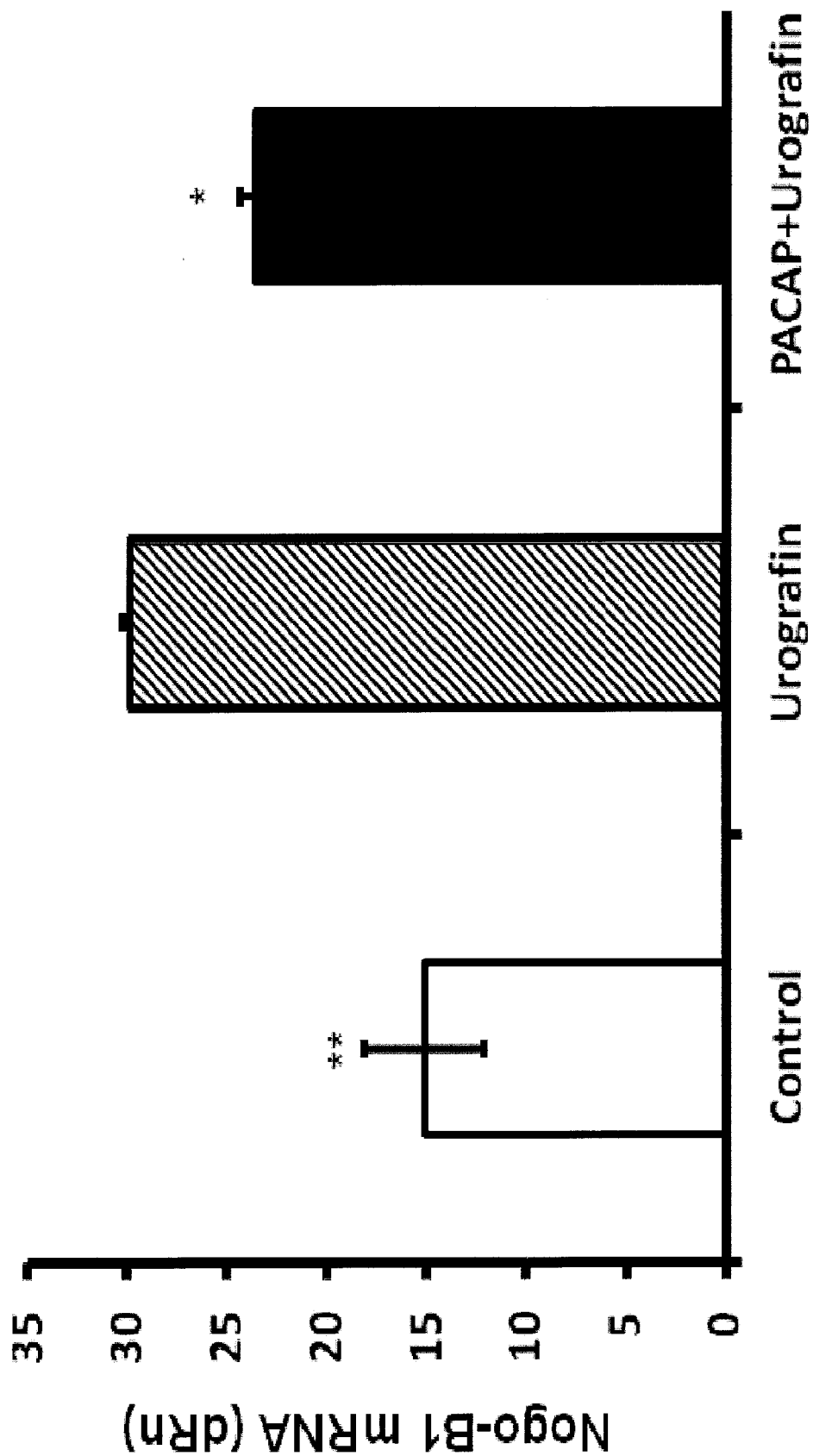
FIG. 12 shows the effects of PACAP38 on the levels of Nogo-B1 mRNA in the kidneys of mice treated with Urografin. Male homozygous eNOS-deficient mice were given a single intravenous injection of Urografin at a dose of 1.85 g iodine/kg body weight. The mice were deprived of water for 24 hours before the start of the experiment. Twenty micrograms of PACAP38 were given intraperitoneally 1 hour before the injection of Urografin and an additional dose was given 12 hours later. The control mice were injected intravenously with the same volume of saline as for the injections of Urografin and PACAP38 on the same schedule. The mice were euthanized 72 hours after the injection of Urografin. Quantification of mRNA levels for Nogo-B1 was made by real-time reverse transcriptase polymerase chain reaction analyses. Each value represents the mean plus/minus the standard error of five or eight determinations. **$p<0.01$ and *$p<0.05$ compared to the group treated with Urografin and saline.
Figure 16:
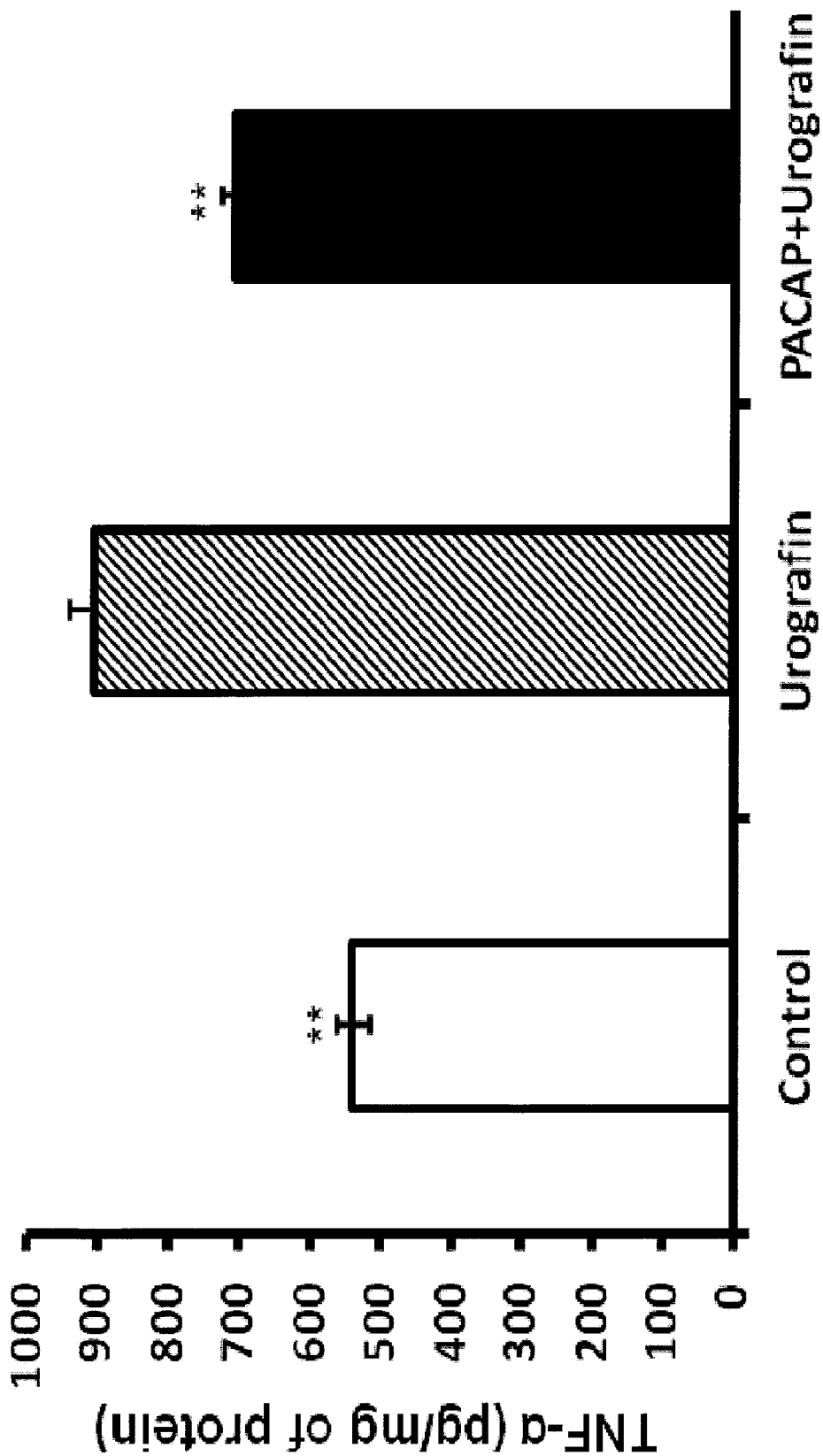
FIG. 16 shows the effects of PACAP38 on the levels of TNF-$\alpha$ in the kidneys of mice treated with Urografin. Male homozygous eNOS-deficient mice were given a single intravenous injection of Urografin at a dose of 1.85 g iodine/kg body weight. The mice were deprived of water for 24 hours before the start of the experiment. Twenty micrograms of PACAP38 were given intraperitoneally 1 hour before the injection of Urografin and an additional dose was given 12 hours later. The control mice were injected intravenously with the same volume of saline as for the injections of Urografin and PACAP38 on the same schedule. The mice were euthanized 72 hours after the injection of Urografin. The concentration of TNF-$\alpha$ in the kidneys was determined with an enzyme-linked immunosorbent assay. Each value represents the mean plus/minus the standard error of five or eight determinations. **$p<0.01$ compared to the group treated with Urografin and saline.
Figure 18:
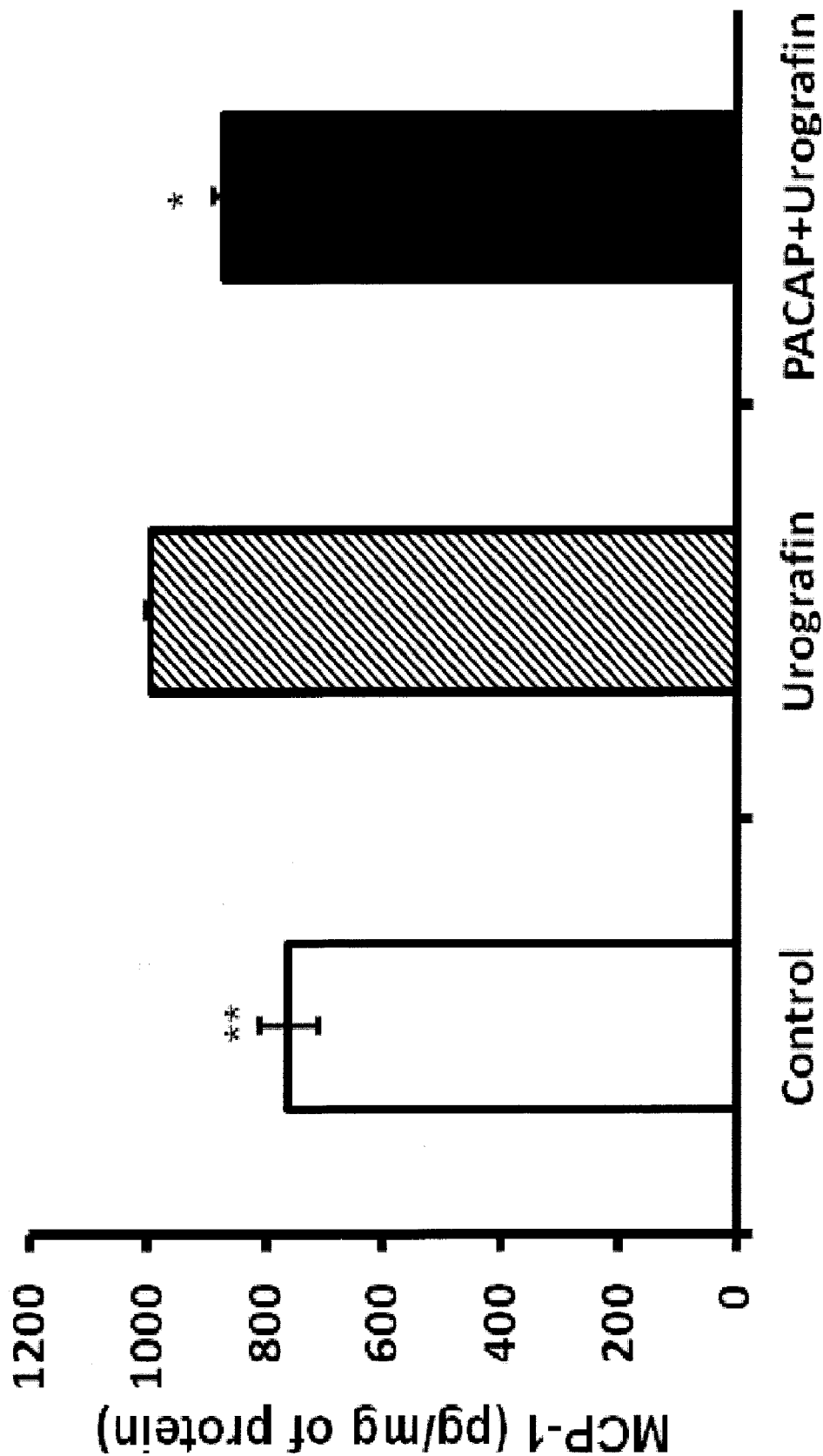
FIG. 18 shows the effects of PACAP38 on the levels of monocyte chemotactic protein-1 (MCP-1) in the kidneys of mice treated with Urografin. Male homozygous eNOS-deficient mice were given a single intravenous injection of Urografin at a dose of 1.85 g iodine/kg body weight. The mice were deprived of water for 24 hours before the start of the experiment. Twenty micrograms of PACAP38 were given intraperitoneally 1 hour before the injection of Urografin and an additional dose was given 12 hours later. The control mice were injected intravenously with the same volume of saline as for the injections of Urografin and PACAP38 on the same schedule. The mice were euthanized 72 hours after the injection of Urografin. The concentration of MCP-1 in the kidneys was determined with an enzyme-linked immunosorbent assay. Each value represents the mean plus/minus the standard error of five or eight determinations. **$p<0.01$ and *$p<0.05$ compared to the group treated with Urografin and saline.
Figure 19:
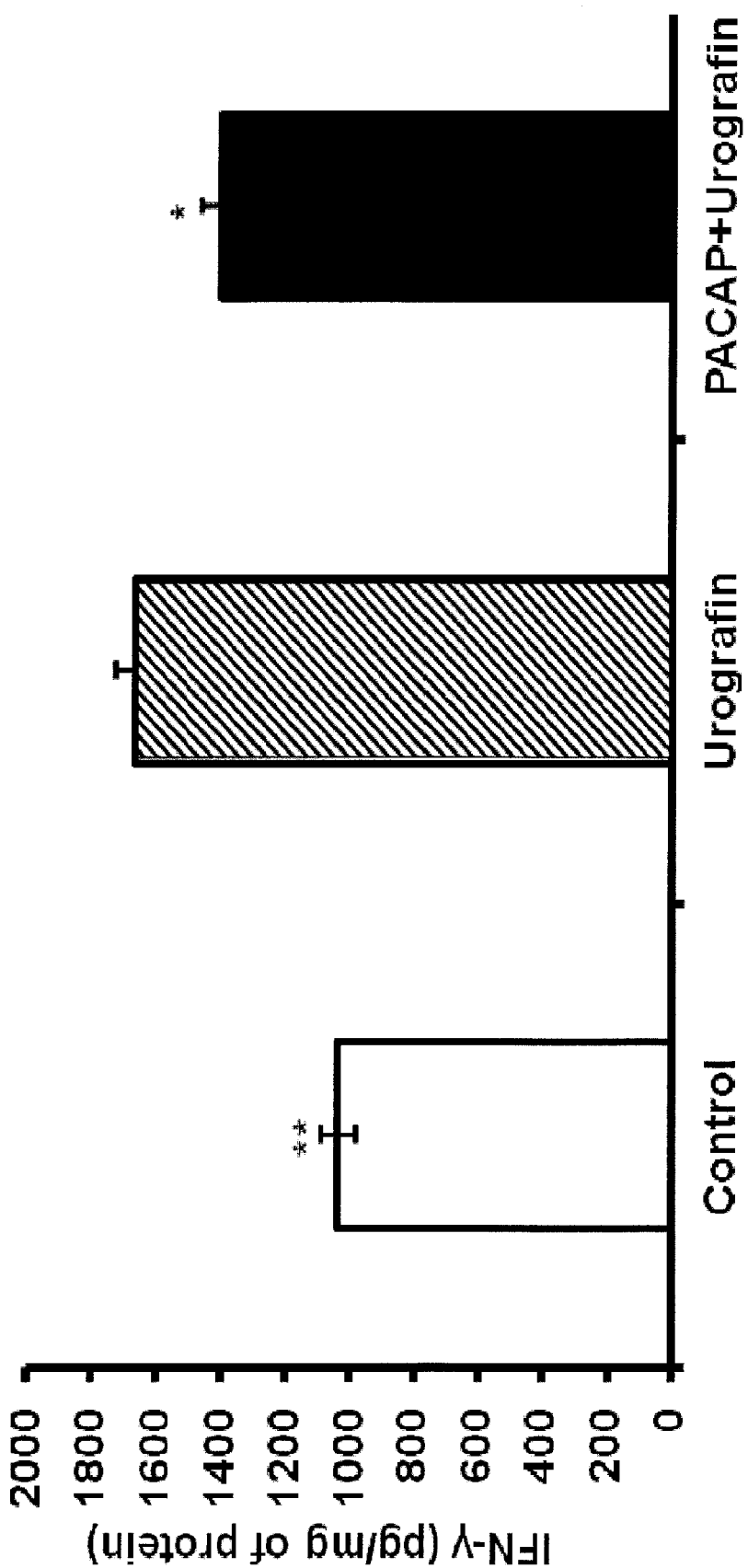
FIG. 19 shows the effects of PACAP38 on the levels of interferon $\gamma$ (IFN-$\gamma$) in the kidneys of mice treated with Urografin. Male homozygous eNOS-deficient mice were given a single intravenous injection of Urografin at a dose of 1.85 g iodine/kg body weight. The mice were deprived of water for 24 hours before the start of the experiment. Twenty micrograms of PACAP38 were given intraperitoneally 1 hour before the injection of Urografin and an additional dose was given 12 hours later. The control mice were injected intravenously with the same volume of saline as for the injections of Urografin and PACAP38 on the same schedule. The mice were euthanized 72 hours after the injection of Urografin. The concentration of IFN-γ in the kidneys was determined with an enzyme-linked immunosorbent assay. Each value represents the mean plus/minus the standard error of five or eight determinations. **p<0.01 and *p<0.05 compared to the group treated with Urografin and saline.

Male homozygous eNOS-deficient mice were given a single intravenous injection of Urografin. Some of these mice were also given 20 μg of PACAP38 were intraperitoneally 1 hour before the injection of Urografin and an additional dose 12 hours after the injection of Urografin. The mice treated only with Urografin had significantly increased kidney levels of TNF-α mRNA (FIG. 9) and iNOS-1 mRNA (FIG. 10). Treatment of Urografin-injected mice with PACAP38 reversed the increases in kidney levels of TNF-α mRNA and iNOS mRNA (FIGS. 9 and 10). The mice treated only with Urografin also had significantly increased kidney levels of TNF-α protein (FIG. 16), MCP-1 (CCL2) protein (FIG. 18) and IFN-γ protein (FIG. 19). Treatment of Urografin-injected mice with PACAP38 reversed the increases in kidney levels of TNF-α protein, MCP-1 protein and IFN-γ protein (FIGS. 16, 18 and 19).

These experiments show that iodinated radiocontrast media induce inflammatory responses in the kidney and that PACAP suppresses the inflammatory responses in the kidney caused by iodinated radiocontrast media.

Example 4

Reduction of Urografin-Induced Fibrotic Responses in the Kidney by PACAP38

The toxic side-effects on the kidney of many commonly used therapeutics, such as cisplatin, cyclosporine A and gentamicin, are accompanied by robust fibrotic responses.

Figure 13:
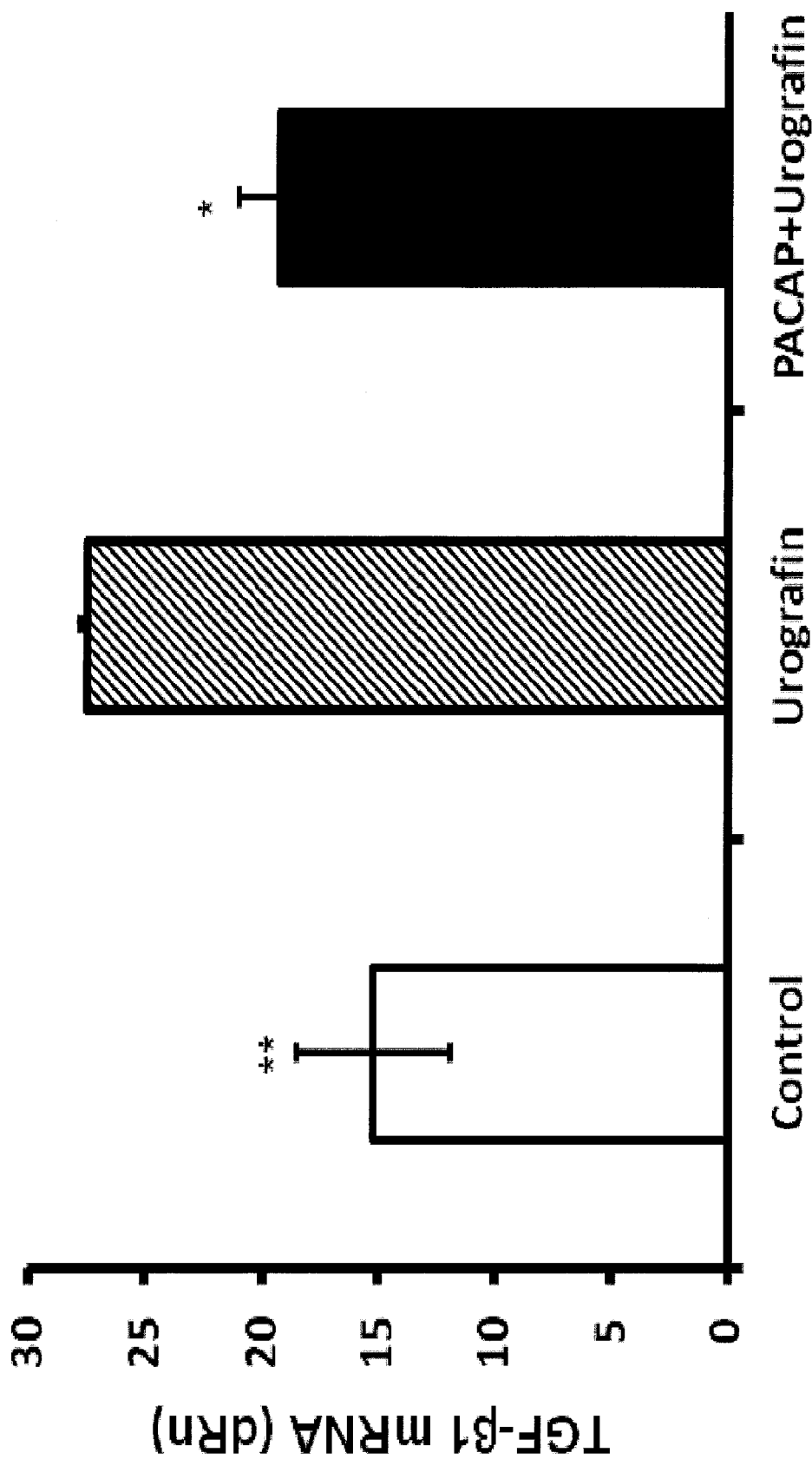
FIG. 13 shows the effects of PACAP38 on the levels of TGF-$\beta$1 mRNA in the kidneys of mice treated with Urografin. Male homozygous eNOS-deficient mice were given a single intravenous injection of Urografin at a dose of 1.85 g iodine/kg body weight. The mice were deprived of water for 24 hours before the start of the experiment. Twenty micrograms of PACAP38 were given intraperitoneally 1 hour before the injection of Urografin and an additional dose was given 12 hours later. The control mice were injected intravenously with the same volume of saline as for the injections of Urografin and PACAP38 on the same schedule. The mice were euthanized 72 hours after the injection of Urografin. Quantification of mRNA levels for TGF-$\beta$1 was made by real-time reverse transcriptase polymerase chain reaction analyses. Each value represents the mean plus/minus the standard error of five or eight determinations. **$p<0.01$ and *$p<0.05$ compared to the group treated with Urografin and saline.
Figure 17:
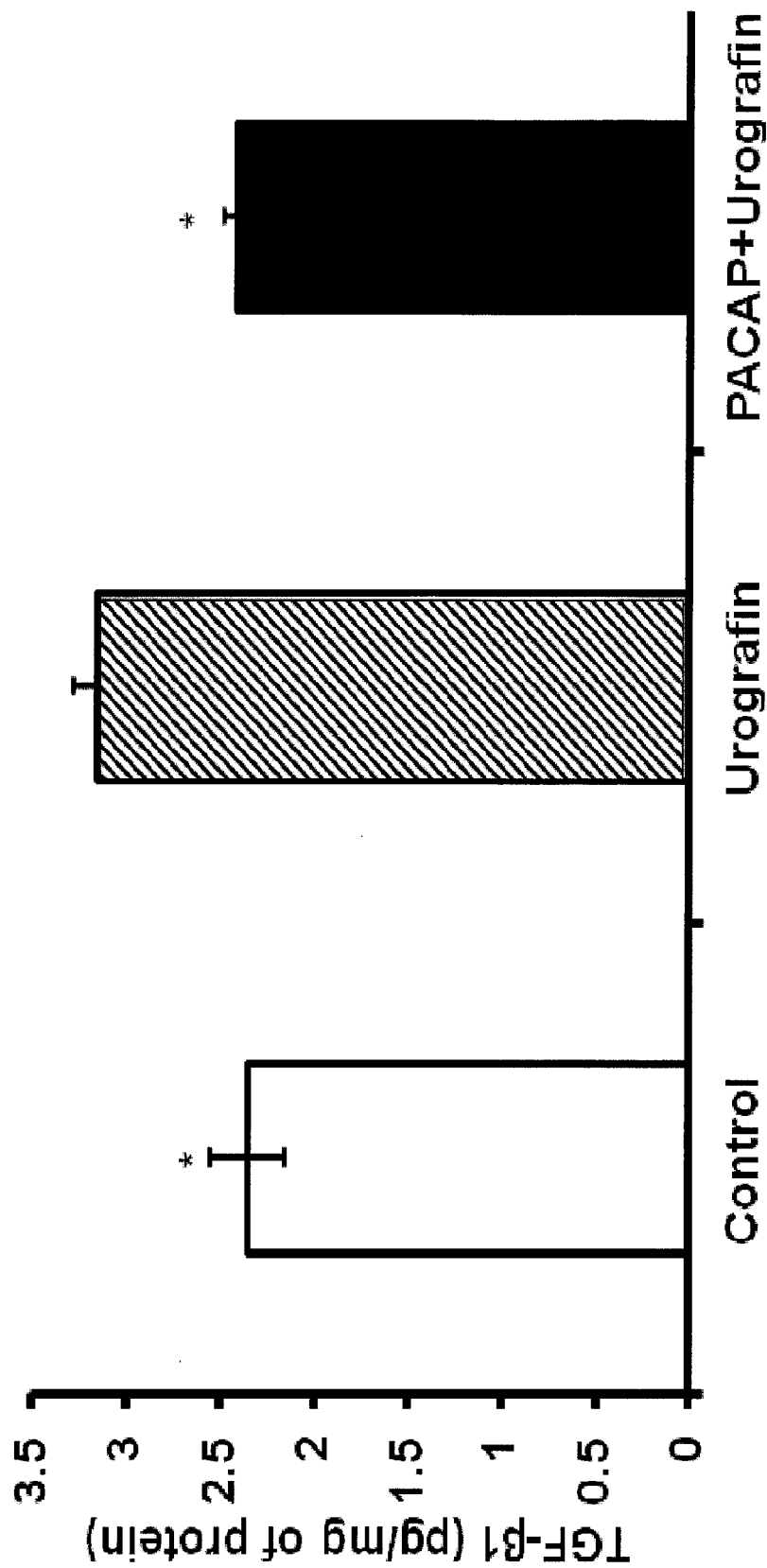
FIG. 17 shows the effects of PACAP38 on the levels of TGF-$\beta$1 in the kidneys of mice treated with Urografin. Male homozygous eNOS-deficient mice were given a single intravenous injection of Urografin at a dose of 1.85 g iodine/kg body weight. The mice were deprived of water for 24 hours before the start of the experiment. Twenty micrograms of PACAP38 were given intraperitoneally 1 hour before the injection of Urografin and an additional dose was given 12 hours later. The control mice were injected intravenously with the same volume of saline as for the injections of Urografin and PACAP38 on the same schedule. The mice were euthanized 72 hours after the injection of Urografin. The concentration of TGF-$\beta$1 in the kidneys was determined with an enzyme-linked immunosorbent assay. Each value represents the mean plus/minus the standard error of five or eight determinations. **$p<0.01$ compared to the group treated with Urografin and saline.

Male homozygous eNOS-deficient mice were given a single intravenous injection of Urografin. Some of these mice were also given 20 μg of PACAP38 were intraperitoneally 1 hour before the injection of Urografin and an additional dose 12 hours after the injection of Urografin. The mice treated only with Urografin had significantly increased kidney levels of TGF-β1 mRNA (FIG. 13) and TGF-β1 protein (FIG. 17). Treatment of the Urografin-injected mice with PACAP38 reversed the increases in kidney levels of TGF-β1 mRNA (FIG. 13) and TGF-β1 protein (FIG. 17).

These experiments show that iodinated radiocontrast media induce fibrotic responses in the kidney and that PACAP suppresses the fibrotic responses in the kidney caused by iodinated radiocontrast media.

Example 5

Reduction of Urografin-Induced Oxidative Stress in the Kidney by PACAP38

The toxic side-effects on the kidney of many commonly used therapeutics, such as cisplatin, cyclosporine A and gentamicin, are also accompanied by oxidative stress. The kidney has the highest levels of Nox-4 of any mammalian organ. Nox-2 is located primarily in intrinsic and infiltrating monocytes.

Figure 14:
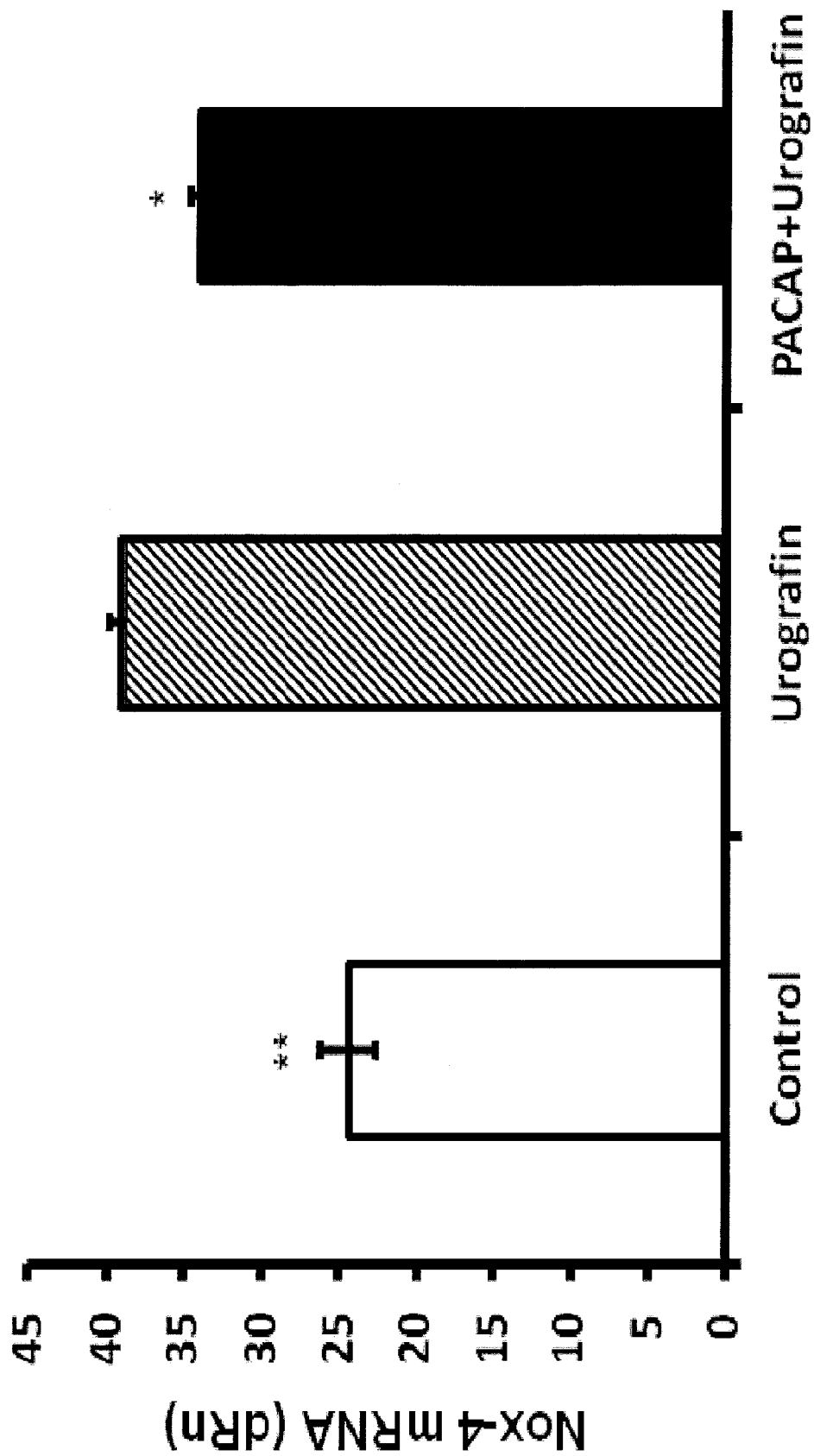
FIG. 14 shows the effects of PACAP38 on the levels of NADPH oxidase (Nox)-4 mRNA in the kidneys of mice treated with Urografin. Male homozygous eNOS-deficient mice were given a single intravenous injection of Urografin at a dose of 1.85 g iodine/kg body weight. The mice were deprived of water for 24 hours before the start of the experiment. Twenty micrograms of PACAP38 were given intraperitoneally 1 hour before the injection of Urografin and an additional dose was given 12 hours later. The control mice were injected intravenously with the same volume of saline as for the injections of Urografin and PACAP38 on the same schedule. The mice were euthanized 72 hours after the injection of Urografin. Quantification of mRNA levels for Nox-4 was made by real-time reverse transcriptase polymerase chain reaction analyses. Each value represents the mean plus/minus the standard error of five or eight determinations. **$p<0.01$ and *$p<0.05$ compared to the group treated with Urografin and saline.
Figure 15:
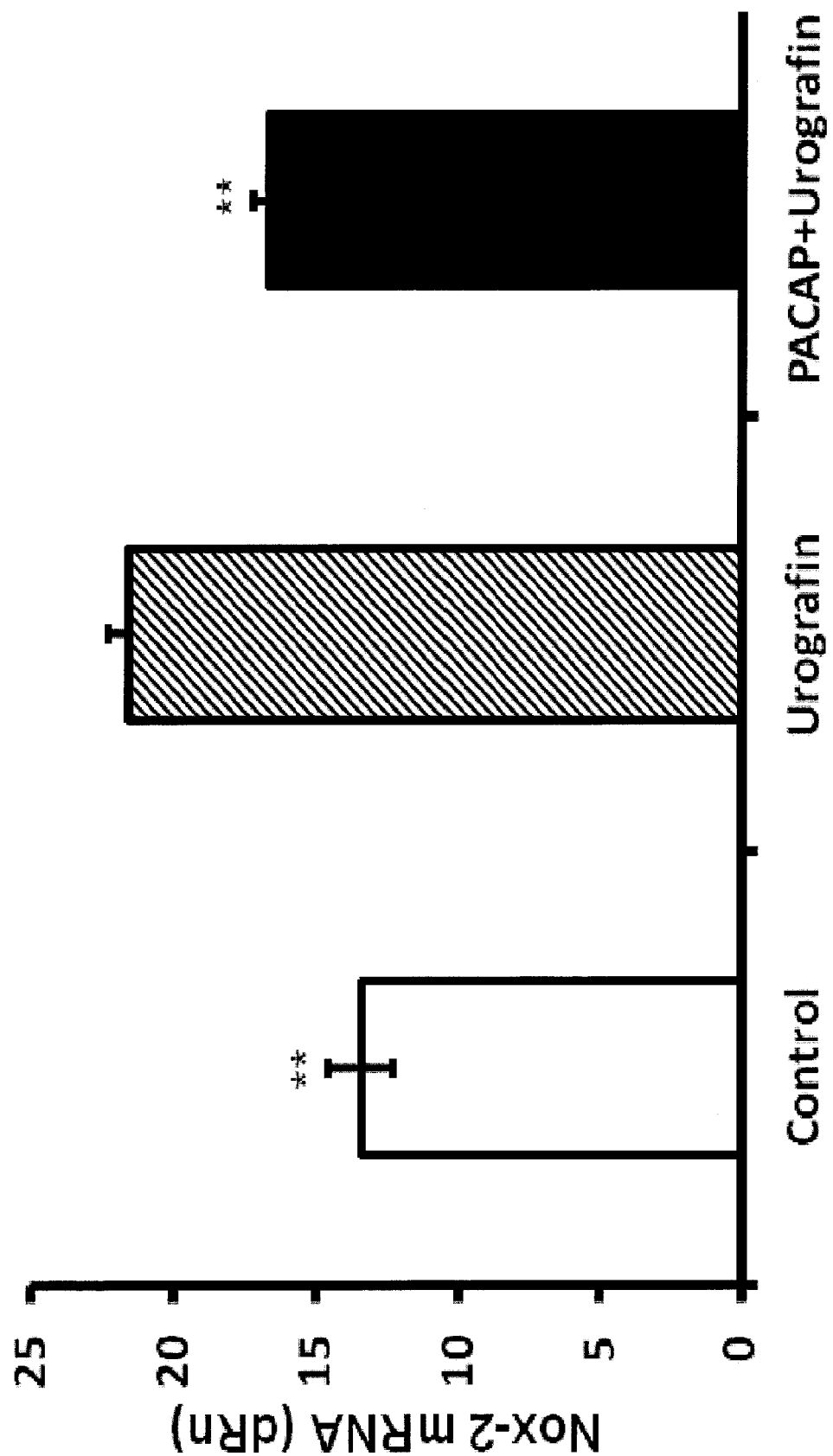
FIG. 15 shows the effects of PACAP38 on the levels of Nox-2 mRNA in the kidneys of mice treated with Urografin. Male homozygous eNOS-deficient mice were given a single intravenous injection of Urografin at a dose of 1.85 g iodine/kg body weight. The mice were deprived of water for 24 hours before the start of the experiment. Twenty micrograms of PACAP38 were given intraperitoneally 1 hour before the injection of Urografin and an additional dose was given 12 hours later. The control mice were injected intravenously with the same volume of saline as for the injections of Urografin and PACAP38 on the same schedule. The mice were euthanized 72 hours after the injection of Urografin. Quantification of mRNA levels for Nox-2 was made by real-time reverse transcriptase polymerase chain reaction analyses. Each value represents the mean plus/minus the standard error of five or eight determinations. **$p<0.01$ and *$p<0.05$ compared to the group treated with Urografin and saline.

Male homozygous eNOS-deficient mice were given a single intravenous injection of Urografin. Some of these mice were also given 20 μg of PACAP38 were intraperitoneally 1 hour before the injection of Urografin and an additional dose 12 hours after the injection of Urografin. The mice treated only with Urografin had significantly increased kidney levels of Nox-4 mRNA (FIG. 14) and Nox-2 mRNA (FIG. 15). Treatment of Urografin-injected mice with PACAP38 reversed the increases in kidney levels of Nox-4 mRNA and Nox-2 mRNA (FIGS. 14 and 15).

These experiments show that iodinated radiocontrast media induce oxidative stress in the kidney and that PACAP suppresses the oxidative stress in the kidney caused by iodinated radiocontrast media.

The above examples (FIGS. 2-19) show that PACAP and PACAP-like compounds potently protect kidney against the toxic side-effects of commonly used ionic and nonionic iodinated radiocontrast media. The above examples also show that the renoprotective effects of PACAP-like compounds are correlated with the immunosuppressive effects of these compounds. Therefore, combination therapy for diagnostic and/or interventional procedures with one or more PACAP-like compounds plus one or more iodinated radiocontrast media will have a better therapeutic index than the same procedures with iodinated radiocontrast media alone.

EQUIVALENTS

Those skilled in the art will recognize, or be able to ascertain using no more than routine experimentation, many equivalents to the specific embodiments of the present invention described herein. Such equivalents are intended to be encompassed by the following claims.

All publications, patents and patent applications mentioned in this specification are herein incorporated by reference into the specification to the same extent as if each individual publication, patent or patent application was specifically indicated to be incorporated herein by reference. In particular, WO 2010/036936, WO 2011/054001, WO 2011/097581, and WO 2006/012394 are incorporated by reference herein in their entirety.

The invention claimed is:

1. A method for treating, managing, preventing, or reducing an injury to a kidney of a mammal resulting from administration of an iodinated radiocontrast medium comprising administering to said mammal in need thereof an effective amount of at least one pituitary adenylate cyclase-activating polypeptide (PACAP)-like compound having at least 90% sequence identity to an amino acid sequence selected from any one of SEQ ID NOs: 1-76, wherein the PACAP-like compound treats, manages, prevents, or reduces said injuries to the kidney.

2. The method of claim 1, wherein said PACAP-like compound is administered at a dose in the range of 1 μg to 1 gram or wherein said administering achieves a concentration of $10^{-14}$ M to $10^{-6}$ of the PACAP-like compound in the blood of the mammal.

3. The method of claim 1, wherein said PACAP-like compound is administered by intravenous infusion, intraperitoneal injection, subcutaneous injection, transcutaneous administration, intramuscular injection, aerosol administration, intranasal administration, or oral administration.

4. The method of claim 1, wherein said method comprises administering said PACAP-like compound one or more times per day, week, month, or year.

5. The method of claim 1, wherein the PACAP-like compound is administered in combination with a cytoprotective agent, a vasodilator, or a vasoconstrictor antagonist.

6. The method of claim 5, wherein the cytoprotective agent is selected from the group consisting of ascorbic acid, vitamin E, mesna, palifermin, erythropoietin, apocynin, diphenylene iodonium, pentoxifylline, etanercept, simvastatin, amifostine, dexrazoxane, and N-acetylcysteine.

7. The method of claim 5, wherein the vasodilator is selected from the group consisting of fenoldopam, atrial natriuretic peptide, theophylline, and aminophylline; or wherein the vasoconstrictor antagonist is SB 209670.

8. The method of claim 1, wherein the PACAP-like compound reduces the severity of an anaphylactic reaction caused by said iodinated radiocontrast medium.

9. The method of claim 1, wherein the mammal is being treated with the iodinated radiocontrast medium in conjunction with a diagnostic and/or interventional procedure.

10. The method of claim 9, wherein the diagnostic and/or interventional procedure is selected from the group consisting of angiography, urography, pyelography, arthrography, cholangiography, diskography, myelography, contrast-enhanced computer tomography, and cerebral ventriculography.

11. The method of claim 10, wherein the angiography is cardiac angiography.

12. The method of 1, wherein said iodinated radiocontrast medium is selected from the group consisting of iobitridol, iodipamide, iodixanol, iohexol, iomeprol, iopamidol, iopentol, iopromide, iotrolan, ioversol, ioxilan, iothalamate, ioxithalamate, ioxaglate, metrizamide, acetrizoate, metrizoate, and diatrizoate.

13. The method of claim 1, wherein said PACAP-like compound is administered to said mammal after administration of said iodinated radiocontrast medium.

14. The method of claim 1, wherein said PACAP-like compound is administered to said mammal before administration of said iodinated radiocontrast medium.

15. The method of claim 1, wherein said PACAP-like compound comprises an amino acid sequence selected from any one of SEQ ID NOs:1-76.

16. The method of claim 1, wherein said mammal is a human, cow, lamb, pig, horse, cat, dog, rat, monkey, rabbit, mouse, or guinea pig.

* * * * *

UNITED STATES PATENT AND TRADEMARK OFFICE
CERTIFICATE OF CORRECTION

PATENT NO. : 9,353,171 B2  
APPLICATION NO. : 14/357393  
DATED : May 31, 2016  
INVENTOR(S) : Vecihi Batuman et al.

It is certified that error appears in the above-identified patent and that said Letters Patent is hereby corrected as shown below:

In the claims,

Column 83, in Claim 2, Line 53, replace "of 1 μg" with --of from 1 μg--

Line 55, replace "$10^{-6}$" with --$10^{-6}$ M--

Column 84, in Claim 12, Line 65, replace "of 1" with --of claim 1--

Signed and Sealed this  
Twenty-sixth Day of July, 2016

Michelle K. Lee  
*Director of the United States Patent and Trademark Office*